(12) United States Patent
Naidu et al.

(10) Patent No.: US 8,039,458 B2
(45) Date of Patent: Oct. 18, 2011

(54) HIV INTEGRASE INHIBITORS

(75) Inventors: B. Narasimhulu Naidu, Durham, CT (US); Yasutsugu Ueda, Clinton, CT (US); John D. Matiskella, Wallingford, CT (US); Michael A. Walker, Durham, CT (US); Jacques Banville, St-Hubert (CA); Francis Beaulieu, Laprairie (CA); Carl Ouellet, Boucherville (CA); Serge Plamondon, Ste-Catherine (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 818 days.

(21) Appl. No.: 11/590,637

(22) Filed: Oct. 31, 2006

(65) Prior Publication Data
US 2007/0111984 A1    May 17, 2007

Related U.S. Application Data

(60) Provisional application No. 60/737,781, filed on Nov. 17, 2005.

(51) Int. Cl.
*A61P 31/18* (2006.01)
*A61K 31/397* (2006.01)
*A61K 31/553* (2006.01)
*C07D 267/02* (2006.01)
*C07D 413/00* (2006.01)

(52) U.S. Cl. ........... 514/210.02; 514/210.21; 514/211.1; 540/524; 540/552

(58) Field of Classification Search ............ 514/210.02, 514/210.21, 211.1; 540/524, 552
See application file for complete search history.

(56) References Cited

U.S. PATENT DOCUMENTS
2006/0046985 A1    3/2006  Crescenzi et al.
2009/0253681 A1*   10/2009 Summa et al. ........... 514/211.09

FOREIGN PATENT DOCUMENTS
EP    1698628 A1        9/2006
WO    WO 2005/061490 A1 7/2005
WO    WO 2005/061501 A2 7/2005
WO    WO 2006/103399 A1 10/2006
WO    WO 2006/121831 A2 11/2006

OTHER PUBLICATIONS

U.S. Appl. No. 11/599,580, filed Nov. 14, 2006, B. Narasimhulu Naidu.
U.S. Appl. No. 60/817,009, filed Jun. 28, 2006, Michael A. Walker, et al.
U.S. Appl. No. 11/511,751, filed Aug. 29, 2006, Jacques Banville, et al.
U.S. Appl. No. 11/138,773, filed May 26, 2005, B. Narasimhulu Naidu, et al.
U.S. Appl. No. 11/138,726, filed May 26, 2005, Jacques Banville, et al.
U.S. Appl. No. 11/126,891, filed May 11, 2005, B. Narasimhulu Naidu, et al.
U.S. Appl. No. 11/288,533, filed Nov. 29, 2005, B. Narasimhulu Naidu, et al.
U.S. Appl. No. 11/110,589, filed Apr. 20, 2005, B. Narasimhulu Naidu.
U.S. Appl. No. 11/273,671, filed Nov. 14, 2005, B. Narasimhulu Naidu.

* cited by examiner

*Primary Examiner* — Brenda Coleman
(74) *Attorney, Agent, or Firm* — James Epperson

(57) ABSTRACT

The invention encompasses a series bicyclic pyrimidinone compounds of Formula I which inhibit HIV integrase and prevent viral integration into human DNA. This action makes the compounds useful for treating HIV infection and AIDS. The invention also encompasses pharmaceutical compositions and methods for treating those infected with HIV.

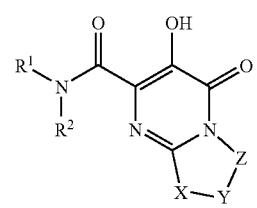

14 Claims, No Drawings

HIV INTEGRASE INHIBITORS

CROSS REFERENCE TO RELATED APPLICATIONS

This application claims the benefit of U.S. provisional application Ser. No. 60/737,781 filed Nov. 17, 2005.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381-390). Clearly, there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase catalyzes insertion of the viral cDNA into the host cell genome, which is a critical step in the viral life cycle. HIV integrase inhibitors belonging to a class of diketo acid compounds prevented viral integration and inhibited HIV-1 replication in cells (Hazuda et al. *Science* 2000, 287, 646). And recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention are compounds of Formula I

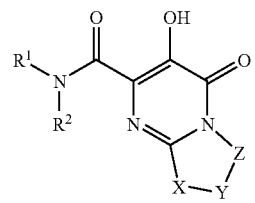

wherein:
$R^1$ is $(Ar^1)$alkyl, $(Ar^1)(CON(R^8)(R^9))$alkyl, $(Ar^1)(CO_2R^{14})$alkyl, $(Ar^1)$hydroxyalkyl, or $(Ar^1)$oxyalkyl;
$R^2$ is hydrogen, alkyl, hydroxy or alkoxy;
$R^3$ is hydrogen, halo, hydroxy, cyano, alkyl, cycloalkyl, $C_{5-7}$cycloalkenyl, haloalkyl, alkoxy, alkylthio, haloalkoxy, $N(R^8)(R^9)$, $NHAr^2$, $N(R^6)SO_2R^7$, $N(R^6)COR^7$, $N(R^6)CO_2R^7$, $OCOR^7$, $OCO_2R^7$, $OCON(R^8)(R^9)$, $OCH_2CO_2R^7$, $OCH_2CON(R^8)(R^9)$, $COR^6$, $CO_2R^6$, $CON(R^8)(R^9)$, $SOR^7$, $S(=N)R^7$, $SO_2R^7$, $SO_2N(R^6)(R^6)$, $PO(OR^6)_2$, $C_{2-4}(R^2)$alkynyl, $R^{13}$, $Ar^2$, or $Ar^3$;
$R^4$ is hydrogen, halo, hydroxy, cyano, alkyl, alkoxy, haloalkyl, haloalkoxy, or $N(R^6)(R^6)$;
$R^4$ is hydrogen, halo, hydroxy, cyano, alkyl, alkoxy, haloalkyl, haloalkoxy, or $N(R^6)(R^6)$;
$R^6$ is hydrogen, alkyl, or cycloalkyl;
$R^7$ is alkyl or cycloalkyl;
$R^8$ is hydrogen, alkyl, hydroxyalkyl, alkoxyalkyl or dialkylaminoalkyl;
$R^9$ is hydrogen, alkyl, hydroxyalkyl, alkoxyalkyl or dialkylaminoalkyl; or
$N(R^8)(R^9)$ taken together is azetidinyl, pyrrolidinyl, $(R^{10})$-piperidinyl, N—$(R^{11})$-piperazinyl, morpholinyl, thiomorpholinyl, or dioxothiazinyl;
$R^{10}$ is hydrogen, alkyl, hydroxy, or hydroxyalkyl;
$R^{11}$ is hydrogen, alkyl, cyclolkyl, $COR^6$, or $CO_2R^6$;
$R^{12}$ is hydrogen, hydroxy, $N(R^6)(R^6)$, $SO_2R^7$, $OSO_2R^7$, or dioxothiazinyl;
$R^{13}$ is azetidinonyl, pyrrolidinonyl, valerolactamyl, caprolactamyl, maleimido, oxazolidinonyl, imidazolidinonyl, triazolonyl, dioxothiazolidinyl or dioxothiazinyl, and is substituted with 0-2 substituents selected from the group consisting of alkyl, hydroxyalkyl, haloalkyl, alkoxyalkyl, and aminoalkyl;
$R^{14}$ is hydrogen or alkyl;
or two $R^{14}$'s taken together are $CH_2CH_2$, $CH_2CH_2CH_2$, $CH_2CH_2CH_2CH_2$, $CH_2CH_2CH_2CH_2CH_2$, $CH_2CH_2CH_2CH_2CH_2CH_2$, $OCH_2CH_2$, $CH_2OCH_2$, $OCH_2CH_2CH_2$, $CH_2OCH_2CH_2$, $OCH_2CH_2CH_2CH_2$, $CH_2OCH_2CH_2CH_2$, $CH_2CH_2OCH_2CH_2$, $OCH_2CH_2CH_2CH_2CH_2$, $CH_2OCH_2CH_2CH_2CH_2$, $CH_2CH_2OCH_2CH_2CH_2$, $N(R^6)CH_2CH_2$, $CH_2N(R^6)CH_2$, $N(R^6)CH_2CH_2CH_2$, $CH_2N(R^6)CH_2CH_2$, $N(R^6)CH_2CH_2CH_2CH_2$, $CH_2N(R^6)CH_2CH_2CH_2$, $CH_2CH_2N(R^6)CH_2CH_2$, $N(R^6)CH_2CH_2CH_2CH_2CH_2$, $CH_2N(R^6)CH_2CH_2CH_2CH_2$, or $CH_2CH_2N(R^6)CH_2CH_2CH_2$, provided that the two $R^{14}$'s are attached to a common carbon atom;

$Ar^1$ is

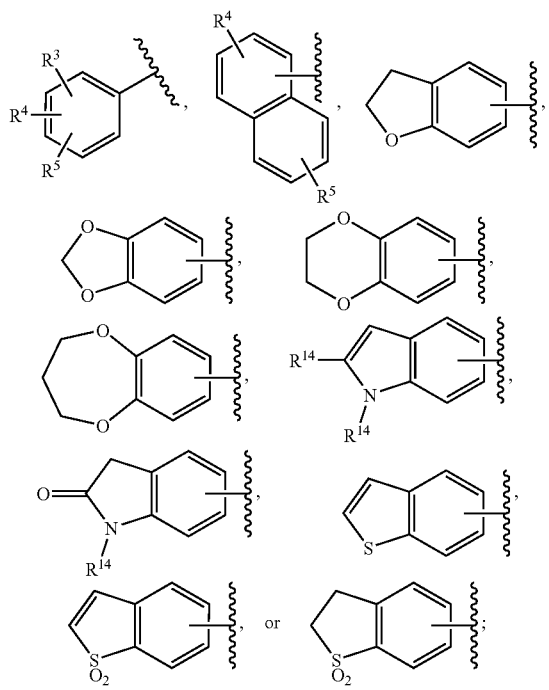

$Ar^2$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, alkyl, alkoxy, $N(R^8)(R^9)$, $CON(R^8)(R^9)$, $CO_2R^6$, $CONHSO_2N(R^6)(R^6)$, $CONHSO_2N(R^6)(phenyl)$, and $CONHSO_2N(R^6)(halophenyl)$;

$Ar^3$ is phenyl substituted with 0-2 substituents selected from the group consisting of halo, cyano, hydroxy, alkyl, alkoxy, alkoxymethyl, haloalkyl, haloalkoxy, $N(R^8)(R^9)$, $CON(R^6)(R^6)$, and $CH_2N(R^8)(R^9)$, or is dioxolanylphenyl; and $X$—$Y$—$Z$ is $C(R^{14})_2C(R^{14})_2OC(R^{14})_2$, $C(R^{14})_2C(R^{14})_2OC(R^{14})_2C(R^{14})_2$, or $C(R^{14})_2C(R^{14})_2OC(R^{14})_2C(R^{14})_2C(R^{14})_2$;

or a pharmaceutically acceptable salt thereof.

Another aspect of the invention are compounds of Formula I

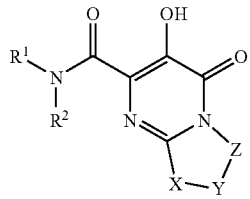

I wherein:

$R^1$ is $(Ar^1)$alkyl, $(Ar^1)(CON(R^8)(R^9))$alkyl, $(Ar^1)(CO_2R^{14})$alkyl, $(Ar^1)$hydroxyalkyl, or $(Ar^1)$oxyalkyl;

$R^2$ is hydrogen, alkyl, hydroxy or alkoxy;

$R^3$ is hydrogen, halo, hydroxy, cyano, alkyl, cycloalkyl, $C_{5-7}$cycloalkenyl, haloalkyl, alkoxy, alkylthio, haloalkoxy, $N(R^8)(R^9)$, $NHAr^2$, $N(R^6)SO_2R^7$, $N(R^6)COR^7$, $N(R^6)CO_2R^7$, $OCOR^7$, $OCO_2R^7$, $OCON(R^8)(R^9)$, $OCH_2CO_2R^7$, $OCH_2CON(R^8)(R^9)$, $COR^6$, $CO_2R^6$, $CON(R^8)(R^9)$, $SOR^7$, $S(=N)R^7$, $SO_2R^7$, $SO_2N(R^6)(R^6)$, $PO(OR^6)_2$, $C_{2-4}(R^{12})$alkynyl, $R^{13}$, $Ar^2$, or $Ar^3$;

$R^4$ is hydrogen, halo, hydroxy, cyano, alkyl, alkoxy, haloalkyl, haloalkoxy, or $N(R^6)(R^6)$;

$R^5$ is hydrogen, halo, hydroxy, cyano, alkyl, alkoxy, haloalkyl, haloalkoxy, or $N(R^6)(R^6)$;

$R^6$ is hydrogen, alkyl, or cycloalkyl;

$R^7$ is alkyl or cycloalkyl;

$R^8$ is hydrogen, alkyl, hydroxyalkyl, alkoxyalkyl or dialkylaminoalkyl;

$R^9$ is hydrogen, alkyl, hydroxyalkyl, alkoxyalkyl or dialkylaminoalkyl; or $N(R^8)(R^9)$ taken together is azetidinyl, pyrrolidinyl, $(R^{10})$-piperidinyl, $N$—$(R^{11})$-piperazinyl, morpholinyl, thiomorpholinyl, or dioxothiazinyl;

$R^{10}$ is hydrogen, alkyl, or hydroxyalkyl;

$R^{11}$ is hydrogen, alkyl, cyclolkyl, $COR^6$, or $CO_2R^6$;

$R^{12}$ is hydrogen, hydroxy, $N(R^6)(R^6)$, $SO_2R^7$, $OSO_2R^7$, or dioxothiazinyl;

$R^{13}$ is azetidinonyl, pyrrolidinonyl, valerolactamyl, caprolactamyl, maleimido, oxazolidonyl, or dioxothiazinyl, and is substituted with 0-1 substituents selected from the group consisting of hydroxymethyl, acetoxymethyl, and aminomethyl;

$R^{14}$ is hydrogen or alkyl;

or two $R^{14}$'s taken together are $CH_2CH_2$, $CH_2CH_2CH_2$, $CH_2CH_2CH_2CH_2$, $CH_2CH_2CH_2CH_2CH_2$, $CH_2CH_2CH_2CH_2CH_2CH_2$, $OCH_2CH_2$, $CH_2OCH_2$, $OCH_2CH_2CH_2$, $CH_2OCH_2CH_2$, $OCH_2CH_2CH_2CH_2$, $CH_2OCH_2CH_2CH_2$, $CH_2CH_2OCH_2CH_2$, $OCH_2CH_2CH_2CH_2CH_2$, $CH_2OCH_2CH_2CH_2CH_2$, $CH_2CH_2OCH_2CH_2CH_2$, $N(R^6)CH_2CH_2$, $CH_2N(R^6)CH_2$, $N(R^6)CH_2CH_2CH_2$, $CH_2N(R^6)CH_2CH_2$, $N(R^6)CH_2CH_2CH_2CH_2$, $CH_2N(R^6)CH_2CH_2CH_2$, $CH_2CH_2N(R^6)CH_2CH_2$, $N(R^6)CH_2CH_2CH_2CH_2CH_2$, $CH_2N(R^6)CH_2CH_2CH_2CH_2$, or $CH_2CH_2N(R^6)CH_2CH_2CH_2$, provided that the two $R^{14}$'s are attached to a common carbon atom;

$Ar^1$ is

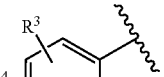

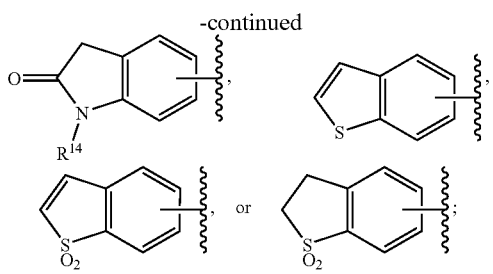

Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, alkyl, alkoxy, N(R⁸)(R⁹), CON(R⁸)(R⁹), CO₂R⁶, CONHSO₂N(R⁶)(R⁶), CONHSO₂N(R⁶)(phenyl), and CONHSO₂N(R⁶)(halophenyl);

Ar³ is phenyl substituted with 0-2 substituents selected from the group consisting of halo, cyano, hydroxy, alkyl, alkoxy, alkoxyalkyl, haloalkyl, haloalkoxy, N(R⁸)(R⁹), CON(R⁶)(R⁶), and CH₂N(R⁸)(R⁹), or is dioxolanylphenyl; and X—Y—Z is C(R¹⁴)₂C(R¹⁴)₂OC(R¹⁴)₂, C(R¹⁴)₂C(R¹⁴)₂OC(R¹⁴)₂C(R¹⁴)₂, or C(R¹⁴)₂C(R¹⁴)₂OC(R¹⁴)₂C(R¹⁴)₂C(R¹⁴)₂; or a pharmaceutically acceptable salt thereof.

Another aspect of the invention is a compound of Formula I where R¹ is (Ar¹)alkyl.

Another aspect of the invention is a compound of Formula I where R¹ is

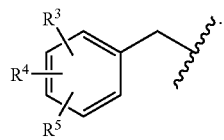

Another aspect of the invention is a compound of Formula I where R¹ is

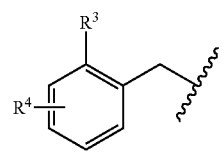

and R³ is other than hydrogen or halo.

Another aspect of the invention is a compound of Formula I where R² is hydrogen.

Another aspect of the invention is a compound of Formula I where R³ is N(R⁸)(R⁹), N(R⁶)COR⁷, OCON(R⁸)(R⁹), CON(R¹)(R⁹), SOR⁷, SO₂R⁷, SO₂N(R⁶)(R⁶), PO(OR⁶)₂, R¹³, or Ar².

Another aspect of the invention is a compound of Formula I where R³ is R¹³.

Another aspect of the invention is a compound of Formula I where R³ is Ar².

Another aspect of the invention is a compound of Formula I where Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl, and is substituted with 0-2 substituents selected from the group consisting of halo and alkyl.

Another aspect of the invention is a compound of Formula I where X—Y—Z is C(R¹⁴)₂CH₂OCH₂, C(R¹⁴)₂CH₂OCH₂CH₂, or C(R¹⁴)₂CH₂OCH₂CH₂CH₂.

Another aspect of the invention is a compound of Formula I where X—Y—Z is C(R¹⁴)₂CH₂OCH₂, C(R¹⁴)₂CH₂OCH₂CH₂, or C(R¹⁴)₂CH₂OCH₂CH₂CH₂, and R¹⁴ is other than hydrogen.

Another aspect of the invention is a compound of Formula I according to one of the following structures.

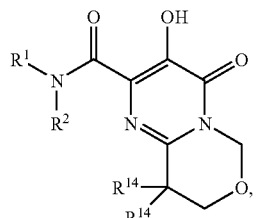

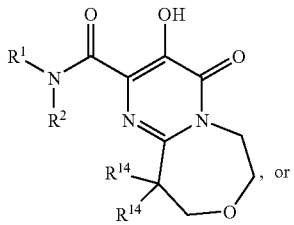

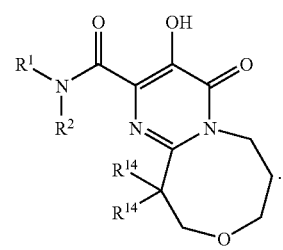

Another aspect of the invention is a compound of Formula I according to one of the following structures.

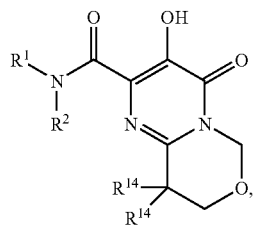

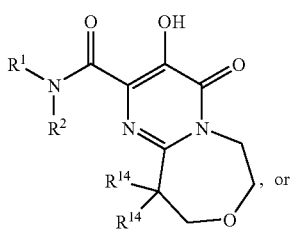

-continued

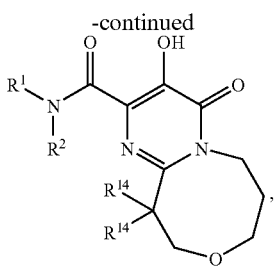

and R[4] is other than hydrogen.

Another aspect of the invention is a compound of Formula I according to one of the following structures.

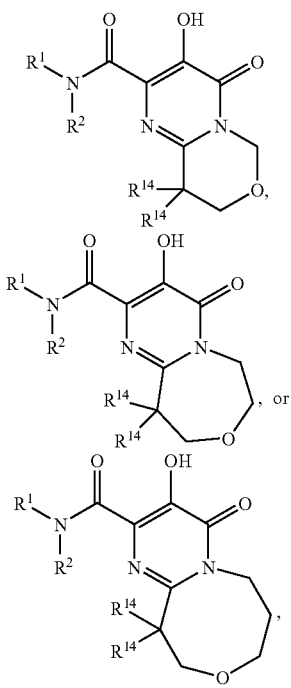

and R[14] is methyl.

Another aspect of the invention is a compound of Formula I according to one of the following structures.

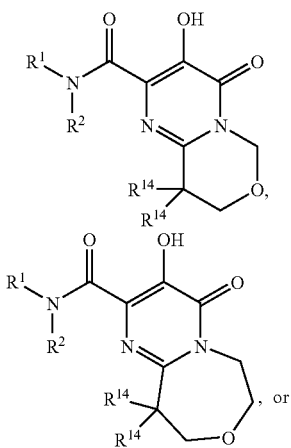

-continued

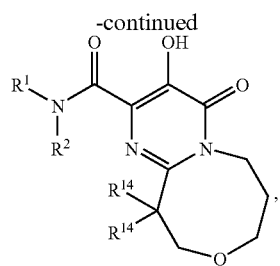

and where the two R[14]'s taken together are $CH_2CH_2$, $CH_2CH_2CH_2$, $CH_2CH_2CH_2CH_2$, $CH_2CH_2CH_2CH_2CH_2$, $CH_2CH_2CH_2CH_2CH_2CH_2$, $CH_2OCH_2CH_2$, $CH_2OCH_2CH_2CH_2$, $CH_2CH_2OCH_2CH_2$, $CH_2OCH_2CH_2CH_2CH_2$, $CH_2CH_2OCH_2CH_2CH_2$, $CH_2CH_2NHCH_2CH_2$, or $CH_2CH_2N(CH_3)CH_2CH_2$.

For a compound of Formula I, any scope of R[1], R[2], R[3], R[4], R[5], R[6], R[7], R[8], R[9], R[10], R[11], R[12], R[13], R[14], Ar[1], Ar[2], Ar[3], or X—Y—Z can be used independently with any scope of any other substituent. Each instance of a variable substituent is independent of any other instance.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

"(Ar[1])oxyalkyl" means Ar[1] is attached at the oxygen.

"Dioxolanyphenyl" means

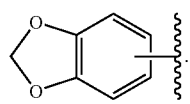

"Dioxothiazolidinyl" means

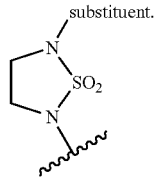

"Dioxothiazinyl" means

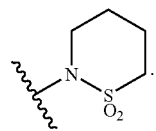

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. An example of enantiomers is shown below. Methods of making and separating stereoisomers are known in the art.

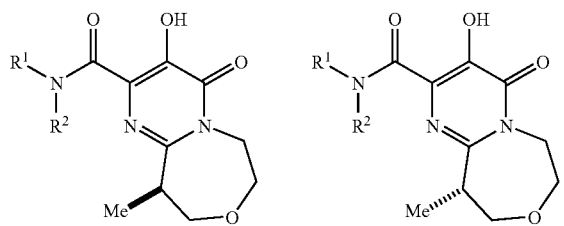

The invention includes all tautomeric forms of the compounds. An example of a tautomeric pair is shown below.

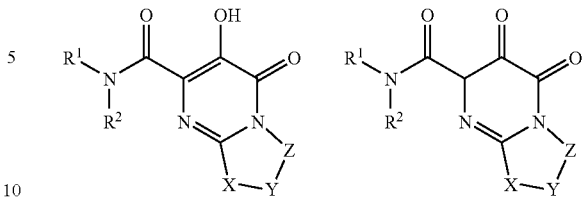

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

Standard amide coupling reagents can be used to effect the formation of the amide bond (see Scheme I). When $R_a$ is a lower alkyl group, $R_a$ can be removed under ester hydrolysis conditions, such as treatment with NaOH, LiOH, or KOH to deliver the corresponding carboxylic acid. Alternatively, $R_a$ can be removed by nucleophilic displacement using NaI. When $R_a$ is benzyl and substituted benzyl, $R_a$ can be removed by hydrogenolysis. Intermediates can be coupled using amide bond forming reagents such as BOP, DCC, EDCI, PyBrop, PyBop benzotriazole-1-yloxy-tris-pyrrolidino-phosphonium hexafluorophosphate), HATU (O-(7-azabenzotriazol-1-yl)-N,N,N',N'-tetramethyluronium hexafluorophosphate) or other reagents (see March, J. Advanced Organic Chemistry, Fourth Edition 1992 John Wiley & Sons, New York). In the Scheme P represents a protecting group, such as benzyl, which can be removed after the coupling reaction.

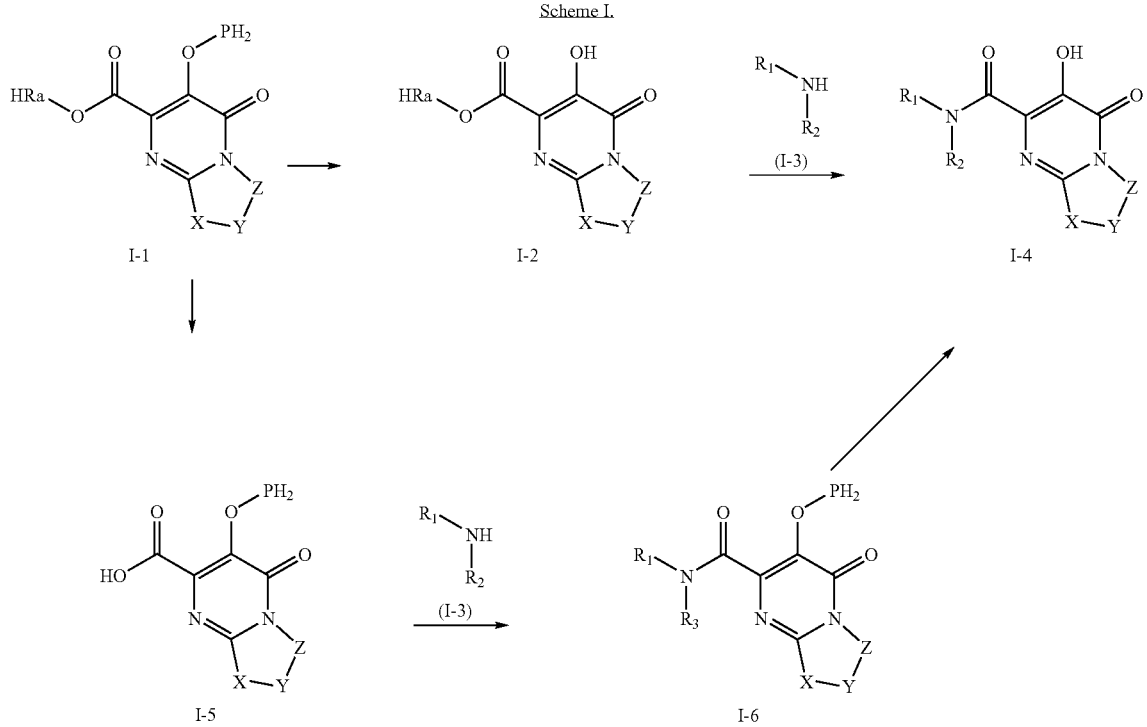

Scheme I.

(P = protecting group)
Ra = alkyl, aryl, benzyl

In Scheme II the syntheses of nitrile intermediates used for the synthesis of the templates are described. In this scheme $L_n$ can be a leaving group such as halide, O-tosyl or O-mesyl and X is a heteroatom such as O, N or S. Deprotonation of the alkyl nitrile, II-1 with an appropriate base, such as lithium diisopropylamide, lithium hexamethyldisilylazide or other bases commonly used in the art, followed by a nucleophilic substitution reaction with electrophiles II-2 or II-5 provides II-3 and II-5 respectively. Intermediate II-6 can be combined with an appropriate nucleophile (II-6), to provide II-3 using reaction conditions known by those in the art. Alternatively nucleophile II-6 can be combined with acrylonitrile to provide an intermediate II-7, which can be further functionalized to provide II-3.

The synthesis of the pyrimidinone templates, shown in Scheme III follows procedures previously disclosed in the art.

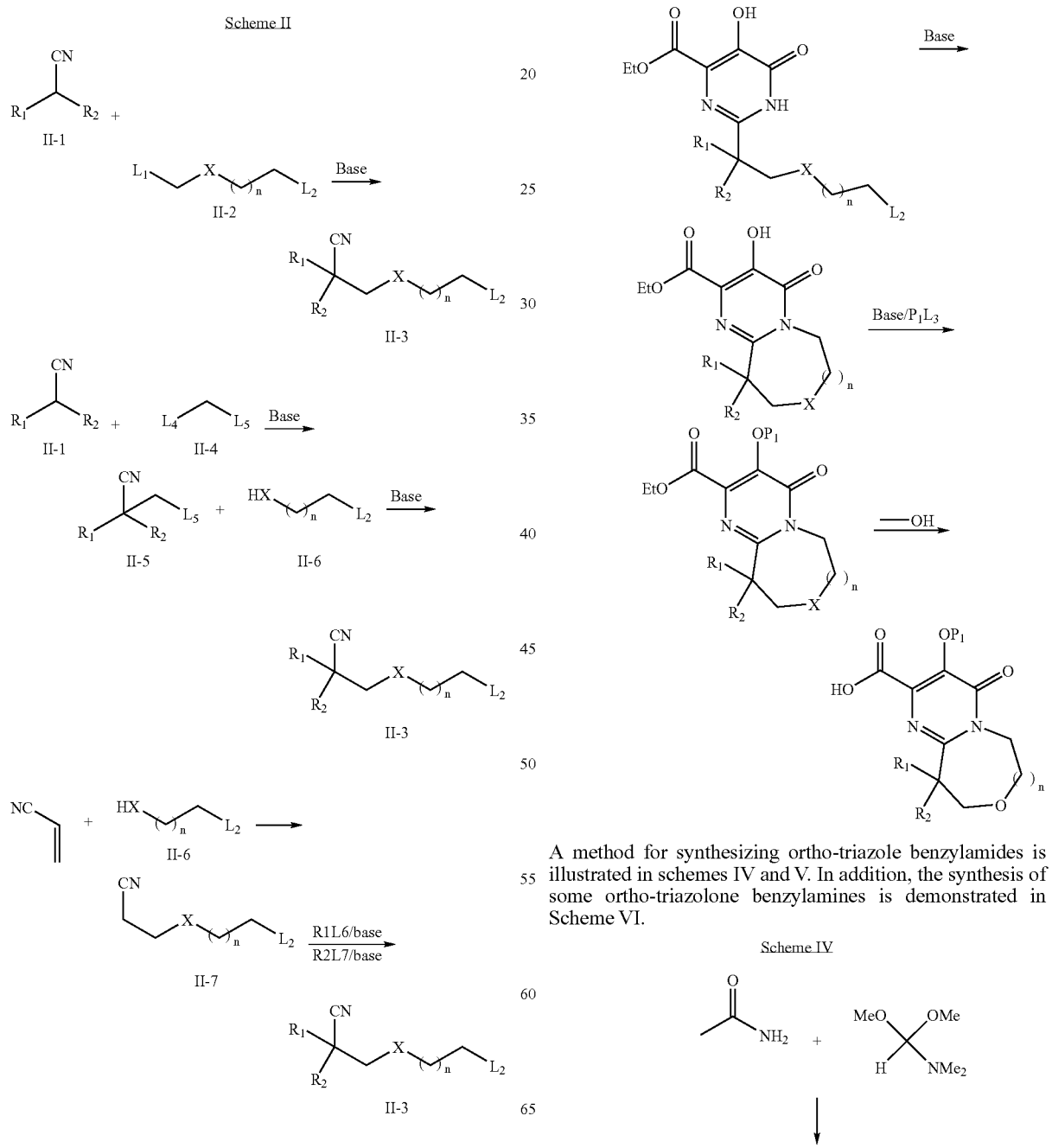

A method for synthesizing ortho-triazole benzylamides is illustrated in schemes IV and V. In addition, the synthesis of some ortho-triazolone benzylamines is demonstrated in Scheme VI.

-continued

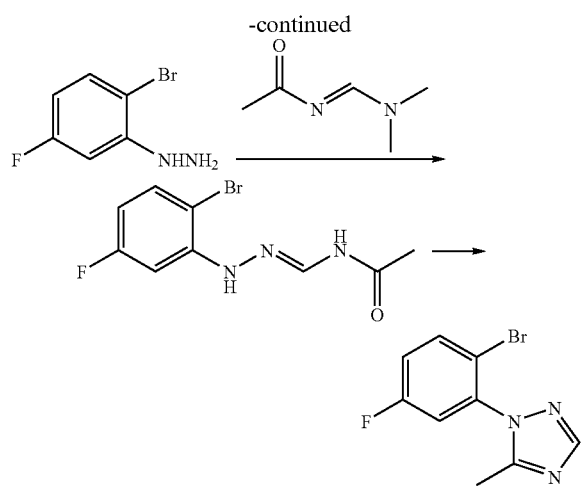

Scheme V

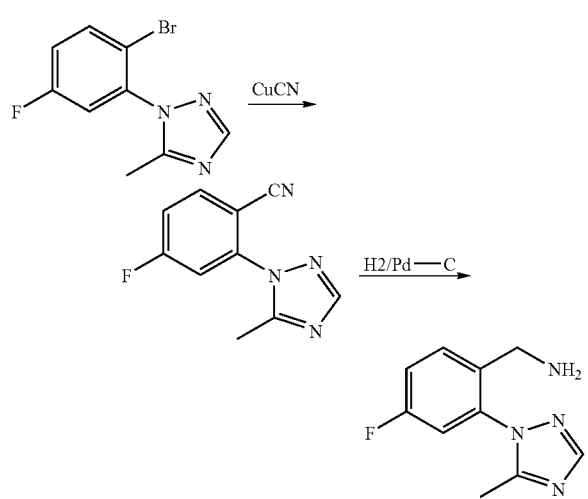

Biological Methods

HIV-Integrase Inhibition Activity. To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol.* 69, 5908-5911 (1995). The sequences of substrate and target DNA were described in *Nucleic Acid Research* 22,1121-1122 (1994).

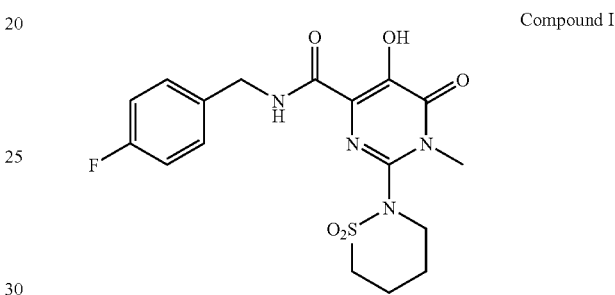

Compound I

HIV-Integrase binding assay. In this assay competitive binding experiments with test compounds and a radiolabeled integrase inhibitor (compound I) are performed against purified integrase. SPA bead/DNA/enzyme complexes were prepared as for the integrase inhibition assay except, to each well, 0.69 μl of integrase enzyme (0.42 mg/μl) was used per 2 μl of LTR DNA-attached scintillation proximity beads (stock 50 mg/ml). Binding reactions were carried out in 96-well white polystyrene assay plates (Corning, #3600). The following was added sequentially to each well: 20 μl of water or 20

Scheme VI

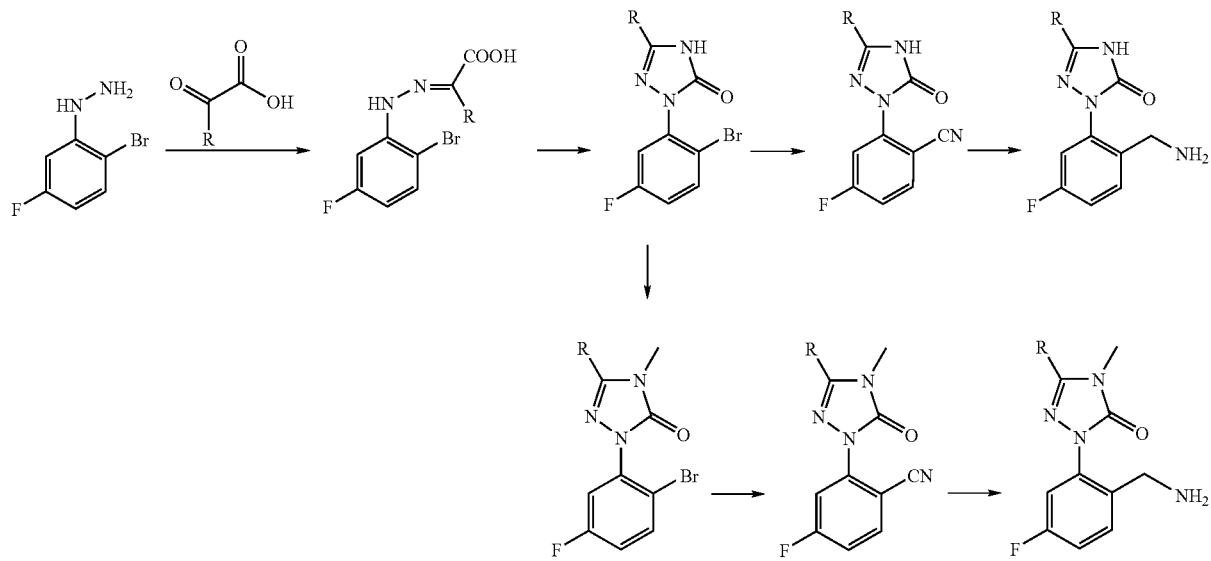

µl of human serum (Cellgro Cat# 35-060-CL), 5 µl of serially diluted compound (in 50% DMSO/50% integrase SPA buffer), 5 µl of [$^3$H]-compound I (6,000 cpm/µl in SPA buffer) and 20 µl of bead/DNA/enzyme complex. The plates were shaken for 2 hours and then allowed to sit at room temperature without shaking overnight. The [$^3$H]-compound I binding was measured using a Topcount scintillation counter. Cheng and Prusoff equations were used to convert the inhibition of compound 1 binding into the corresponding Ki value. Results are shown in the Table 1. Activity equal to A refers to a compound having Ki=0.001 to 0.003 µM while B and C denote compounds having Ki=0.003 to 0.05 µM and Ki≧0.050 µM respectively.

TABLE 1

| Example | in vitro binding |
|---|---|
| 1 | B |
| 2 | B |
| 3 | B |
| 4 | B |
| 5 | B |
| 6 | B |
| 7 | A |
| 8 | A |
| 9 | A |
| 10 | A |
| 11 | B |
| 12 | A |
| 13 | A |
| 14 | A |
| 15 | A |
| 16 | A |
| 17 | B |
| 18 | B |
| 19 | B |
| 20 | C |
| 21 | A |
| 22 | B |
| 23 | A |
| 24 | B |
| 25 | B |
| 26 | B |
| 27 | B |
| 28 | B |
| 29 | |
| 30 | |
| 31 | B |
| 32 | B |
| 33 | B |
| 34 | A |
| 35 | B |
| 36 | B |
| 37 | B |
| 38 | B |
| 39 | B |
| 40 | B |
| 41 | B |
| 42 | A |

Inhibition of HIV replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration (EC$_{50}$) was calculated by using the exponential form of the median effect equation where (Fa)=1/[1+(ED$_{50}$/drug conc.)$^m$] (Johnson V A, Byington R T. Infectivity Assay. In *Techniques in HIV Research*. ed. Aldovini A, Walker B D. 71-76. New York: Stockton Press. 1990). The anti-viral activity of compounds was evaluation under three serum conditions, 10% FBS, 15 mg/ml human serum albumin/10% FBS or 40% human serum/5% FBS, and the results from at least 2 experiments were used to calculate the EC$_{50}$ values. Results are shown in the Table 2. Activity equal to A refers to a compound having EC$_{50}$=0.001 to 0.010 µM while B and C denote compounds with EC$_{50}$=0.010 to 0.050 µM and EC$_{50}$>0.05 µM respectively.

TABLE 2

| Example | antiviral actitively |
|---|---|
| 1 | B |
| 2 | A |
| 3 | A |
| 4 | A |
| 5 | B |
| 6 | A |
| 7 | B |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | C |
| 21 | A |
| 22 | A |
| 23 | A |
| 24 | A |
| 25 | C |
| 26 | B |
| 27 | A |
| 28 | A |
| 29 | |
| 30 | |
| 31 | C |
| 32 | B |
| 33 | A |
| 34 | A |
| 35 | A |
| 36 | A |
| 37 | B |
| 38 | A |
| 39 | A |
| 40 | A |
| 41 | B |
| 42 | A |

See US 20050250256109 and US 20050267105 for some other compounds demonstrating HIV integrase activity.

Pharmaceutical Composition and Methods of Use

The compounds of this invention inhibit HIV integrase. HIV integrase inhibitors belonging to a class of diketo acid compounds prevented viral integration and inhibited HIV-1 replication cells (Hazuda et al. *Science* 2000, 287, 646). Recently, HIV integrase inhibitors have been accepted into clinical trials for treating AIDS and HIV infection (*Neamati Expert. Opin. Ther. Patents* 2002, 12, 709, Pais and Burke *Drugs Fut.* 2002, 27, 1101).

Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "AC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. *Some examples of dosages are* 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 4 lists some agents useful in treating AIDS and HIV infection which are suitable for this invention.

TABLE 4

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combinationwith AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |

TABLE 4-continued

| DRUG NAME | MANUFACTURER | INDICATION |
|---|---|---|
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptase inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |

IMMUNOMODULATORS

| DRUG NAME | MANUFACTURER | INDICATION |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

TABLE 4-continued

| DRUG NAME | MANUFACTURER | INDICATION |
|---|---|---|
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

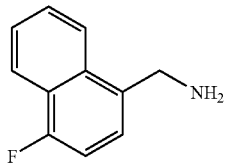

Intermediate 1

(4-Fluoronaphthalen-1-yl)methanamine hydrochloride. A solution of 1-cyano-4-fluoronapthalene (1.05 g, 6.12 mmol) and 1.5 mL of HCl (aq.) in absolute ethanol (50 mL) was stirred under a hydrogen atmosphere (balloon) with 10% palladium on carbon (0.20 g) for 16 hours. The catalyst was removed by filtration through Celite®, and the filtrate concentrated under vacuum. The resulting solid was triturated with ether and collected by filtration to give the title compound (0.575 g, 44% yield) as an off white solid.

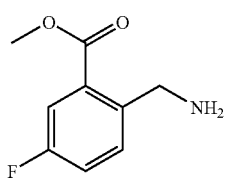

Intermediate 2

Methyl 2-(aminomethyl)-5-fluorobenzoate trifluoroacetic acid salt. Methyl 2-((tert-butoxycarbonyl)methyl)-5-fluorobenzoate, prepared according to literature methods, was treated with trifluoroacetic acid to provide the title compound. Yield 100%; $^1$H NMR (300 MHz, DMSO-d6) δ ppm: 3.89 (3H, s) 4.32 (2H, q, J=5.61 Hz) 7.51-7.71 (2H, m) 7.78 (1H, dd, J=9.33, 2.38 Hz) 8.13 (2H, brs); LC/MS m/z 184 (M+H).

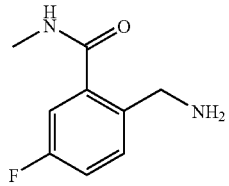

Intermediate 3

2-Aminomethyl-5-fluoro-N-methyl-benzamide trifluoroacetic acid salt. To a solution of tert-butyl 4-fluoro-2-(methylcarbamoyl)benzylcarbamate (7.70 g, 27.3 mmol), prepared from 2-bromo-5-fluorobenzoic acid using literature methods in CH$_2$Cl$_2$ (100 mL) was added CF$_3$CO$_2$H (25 mL) and the mixture stirred at room temperature for 15 min. This was concentrated in vacuo and the residue triturated with diethyl ether to obtain 8.0 g (Yield 99%) of the title compound as a white powder. $^1$H NMR (300 MHz, D$_2$O) δ ppm: 2.93 (3H, s) 4.20 (2H, s) 7.35 (1H, dt, J=8.5, 3 Hz) 7.42 (1H, dd, J=9.0, 2.7 Hz) 7.57 (1H, dd, J=8.4, 5.5 Hz); LC/MS m/z 183 (M+H).

Intermediate 4

2-(Aminomethyl)-N-cyclopropyl-5-fluorobenzamide trifluoroacetic acid salt. A solution of tert-butyl 2-(cyclopropylcarbamoyl)-4-fluorobenzylcarbamate (130 mg, 0.42 mmol), prepared according to literature methods, in CH$_2$Cl$_2$ (5 mL) was stirred with trifluoroacetic acid (3 mL) at room temperature for 10 min, then concentrated in vacuo to give 140 mg (Yield 100%) of the title compound as a foam: $^1$H NMR (DMSO-d$_6$, 300 MHz) δ ppm: 0.62 (2H, m, CH$_2$), 0.73 (2H, m, CH$_2$), 2.86 (1H, m, CH), 4.02-4.07 (2H, ABq, NCH$_2$), 7.46 (2H, m, Ar—Hs), 7.58 (1H, m, Ar—H), 8.11 (3H, br, NH3), 8.81 (1H, d, J=4.4 Hz, NH); LC/MS m/z 209 (M+H).

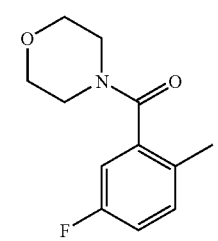

Intermediate 5

(5-Fluoro-2-methylphenyl)(morpholino)methanone. To a solution of morpholine (870 mg, 10 mmol) and triethylamine (1.1 g, 10.8 mmol) in CH$_2$Cl$_2$ (15 mL) was added a solution of 5-fluoro-2-methylbenzoyl chloride (1.72 g, 10 mmol) in CH$_2$Cl$_2$ (5 mL), dropwise, and the mixture stirred for 15 min. The mixture was then washed with water, and the organic fraction dried (MgSO$_4$), filtered, and concentrated to obtain 2.19 g (Yield 98%) of the title compound as a solid: $^1$H NMR (500 MHz, CDCl$_3$) δ ppm: 2.27 (3H, s) 3.24 (2H, d, J=4 Hz) 3.58 (2H, s) 3.79 (4H, dd, J=18, 3.8 Hz) 6.88 (1H, dd, J=8.2, 2.8 Hz) 6.92-7.05 (1H, m) 7.18 (1H, dd, J=8.4, 5.3 Hz).

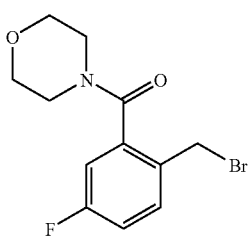

Intermediate 6

(2-(Bromomethyl)-5-fluorophenyl)(morpholino)methanone. A mixture of 5-fluoro-2-methylphenyl)(morpholino)methanone (2.1 g, 9.5 mmol) and N-bromosuccinimide (2.0 g, 11 mmol) in CCl$_4$ (30 mL) was heated at reflux. To this mixture was added benzoylperoxide (242 mg, 1 mmol) and the mixture heated at reflux for 2 hrs. After cooling, the insoluble materials were filtered and the filtrate purified by column chromatography (SiO$_2$, 0-10% ether in CH$_2$Cl$_2$) to give 1.1 g (Yield 38%) of the title compound as a clear oil: $^1$H NMR (300 MHz, CDCl$_3$) δ ppm: 3.31 (2H, t, J=4.94 Hz) 3.55-4.02 (6H, m) 4.56 (2H, dd, J=128.81, 9.51 Hz) 6.89 (1H, dd, J=8.23, 2.74 Hz) 6.96-7.12 (1H, m) 7.33-7.49 (1H, m); LC/MS m/z 302 (M+H).

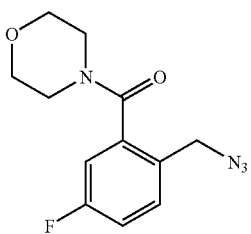

Intermediate 7

(2-(Azidomethyl)-5-fluorophenyl)(morpholino)methanone. To a solution of 2-(bromomethyl)-5-fluorophenyl)(morpholino)methanone (1.0 g, 3.32 mmol) in dimethylformamide (10 mL) was added sodium azide (230 mg, 3.5 mmol) and the mixture stirred under a nitrogen atmosphere for 1 h. The solvent was evaporated in vacuo, and the residue dissolved in CH$_2$Cl$_2$, then washed with water. The organic phase was dried (Na$_2$SO$_4$), filtered, concentrated, and the residue purified by column chromatography (SiO$_2$, CH$_2$Cl$_2$) to provide 770 mg (Yield 88%) of the title compound as an oil: $^1$H NMR (300 MHz, CDCl$_3$) δ ppm: 3.27 (2H, s) 3.51-3.65 (2H, m) 3.66-3.97 (4H, m) 4.38 (2H, brs) 6.92 (1H, dd, J=8.2, 2.7 Hz) 7.07 (1H, dt, J=8.5, 3 Hz) 7.34 (1H, dd, J=8.4, 5.5 Hz); LC/MS m/z 265 (M+H).

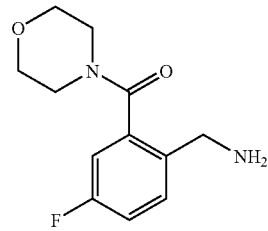

Intermediate 8

(2-(Aminomethyl)-5-fluorophenyl)(morpholino)methanone hydrochloride. To a solution of 2-(azidomethyl)-5-fluorophenyl)(morpholino)methanone (770 mg, 2.92 mmol,) in ethanol (20 mL) was added 4N HCl (1 mL) and 10% Pd—C (100 mg), and the mixture hydrogenated at 1 atm of H$_2$ for 3 hrs. The catalyst was removed by filtration and the filtrate concentrated. The residue was purified by C18 reverse phase silica gel column chromatography (YMC ODS, 0-5% CH$_3$CN/H$_2$O) to obtain 350 mg (Yield 44%) of the title compound, (2-(aminomethyl)-5-fluorophenyl)(morpholino)-methanone hydrochloride as a white powder: $^1$H NMR (300 MHz, DMSO-d6) δ ppm: 3.0-4.0 (8H, m), 3.78 (2H, t, J=5 Hz), 7.32 (1H, dd, J=8.8, 2.6 Hz), 7.35-7.44 (1H, t, J=8.5, 3 Hz), 7.75 (1H, dd, J=8.8, 5.5 Hz); LC/MS m/z 239 (M+H).

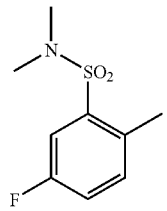

Intermediate 9

5-Fluoro-2,N,N-trimethyl-benzenesulfonamide. To a solution of 5-fluoro-2-methyl-benzenesulfonyl chloride (4.18 g, 20 mmol) in tetrahydrofuran (25 mL) was added, dropwise, a solution of dimethylamine in tetrahydrofuran (2M, 25 mL, 50 mmol) over 15 min. and the mixture stirred for 5 min. The insoluble materials were filtered and the filtrate concentrated. The residue was purified by column chromatography (SiO$_2$, 5% ether in CH$_2$Cl$_2$) to provide 4.3 g (Yield 90%) of the title compound as a clear oil: $^1$H NMR (500 MHz, CDCl$_3$) δ ppm: 2.57 (3H, s) 2.82 (3H, s) 2.82 (3H, s) 7.12-7.18 (1H, m) 7.28 (1H, dd, J=8.2, 5.5 Hz) 7.59 (1H, dd, J=8.2, 2.1 Hz); LC/MC m/z 218 (M+H).

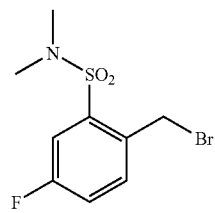

Intermediate 10

2-Bromomethyl-5-fluoro-N,N-dimethyl-benzenesulfonamide. Under nitrogen, a mixture of 5-fluoro-2,N,N-trimethyl-benzenesulfonamide (435 mg, 2.0 mmol) and N-bromosuccinimide (391 mg, 2.2 mmol) in CCl$_4$ (20 mL) was stirred at 80-90° C. for 5 min. To this mixture was added 2,2'-azobisisobutyronitrile (AIBN, 100 mg) and stirring continued at 80-90° C. for 30 min. After cooling, the insoluble precipitates were filtered and the filtrate concentrated and purified by column chromatography (SiO$_2$, CH$_2$Cl$_2$) to provide 440 mg (Yield 74%) of the title compound; $^1$H NMR (500 MHz, CDCl$_3$) δ ppm: 2.87 (6H, s) 4.86 (2H, s) 7.28 (1H, dd, J=8.55, 2.75 Hz) 7.61-7.65 (2H, m); LC/MC m/z 296/298 (M+H).

Intermediate 11

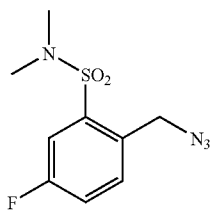

2-Azidomethyl-5-fluoro-N,N-dimethyl-benzenesulfonamide. A mixture of 2-bromomethyl-5-fluoro-N,N-dimethyl-benzenesulfonamide (880 mg, 2.97 mmol) and sodium azide (200 mg, 3 mmol) in dimethylformamide (4 mL) was stirred at 55-60° C. for 30 min after which the solvent was removed in vacuo. The residue was partitioned between CH$_2$Cl$_2$ and water, and the organic fraction was washed with water, dried (Na$_2$SO$_4$), filtered and concentrated to provide 670 mg (Yield 87%) of the title compound as a yellow oil; $^1$H NMR (500 MHz, CDCl$_3$) δ ppm: 2.84 (6H, s) 4.78 (2H, s) 7.29-7.34 (1H, m) 7.59-7.64 (2H, m).

Intermediate 12

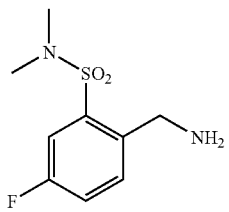

2-(Aminomethyl)-5-fluoro-N,N-dimethylbenzenesulfonamide. To a solution of 2-azidomethyl-5-fluoro-N,N-dimethyl-benzenesulfonamide (660 mg, 2.6 mmol) in tetrahydrofuran (10 mL) and water (2 mL) was added triphenylphosphine (740 mg, 2.8 mmol), and the mixture stirred under nitrogen for 1 hr. The tetrahydrofuran was evaporated in vacuo and a mixture of the residue and 6N HCl (3 mL) in MeOH (5 mL) was heated at 80° C. for 20 hrs. This was washed with CH$_2$Cl$_2$, and the aqueous phase made basic with dilute NH$_4$OH then extracted with CH$_2$Cl$_2$. The organic extract was dried (Na$_2$SO$_4$), filtered and concentrated to provide 210 mg (0.91 mmol, Yield 35%) of the title compound; $^1$H NMR (500 MHz, CDCl$_3$) δ ppm: 2.84 (6H, s) 4.10 (2H, s) 7.23-7.29 (1H, m) 7.53-7.60 (2H, m); LC/MS m/z 233 (M+H).

Intermediate 13

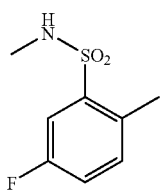

5-Fluoro-2,N-dimethyl-benzenesulfonamide. To a solution of 5-fluoro-2-methyl-benzenesulfonyl chloride (4.18 g, 20 mmol) in acetone (20 mL) was added a 40% aqueous solution of methylamine (4.5 mL, 60 mmol) under nitrogen and the mixture stirred for 5 min. Acetone was removed in vacuo and the aqueous residue extracted with CH$_2$Cl$_2$. The CH$_2$Cl$_2$ extract was dried (Na$_2$SO$_4$), filtered, concentrated and the residue purified by column chromatography (SiO$_2$, 10% ether in CH$_2$Cl$_2$) to provide 3.9 g (19.2 mmol, Yield 96%) of the title compound as a white solid; $^1$H NMR (500 MHz, CDCl$_3$) δ ppm: 2.59 (3H, s), 2.67 (3H, d, J=5.5 Hz), 4.41 (1H, brs), 7.13-7.20 (1H, m), 7.29 (1H, dd, J=8.2, 5.5 Hz), 7.69 (1H, J=8.6, 2.1 Hz); LC/MS m/z 204 (M+H).

Intermediate 14

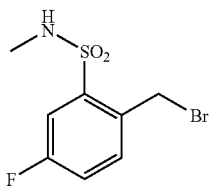

2-Bromomethyl-5-fluoro-N-methyl-benzenesulfonamide. $^1$H NMR (500 MHz, CDCl$_3$) δ ppm: 2.64 (3H, d, J=5.19 Hz) 4.91 (1H, d, J=3.66 Hz) 4.98 (2H, s) 7.26-7.30 (1H, m) 7.54 (1H, dd, J=8.6, 5.2 Hz) 7.73 (1H, dd, J=8.4, 2.6 Hz); LC/MS m/z 282/284.

Intermediate 15

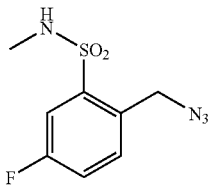

2-Azidomethyl-5-fluoro-N-methyl-benzenesulfonamide. $^1$H NMR (500 MHz, CDCl$_3$) δ ppm: 2.65 (3H, d, J=5.19 Hz) 4.81 (2H, s) 4.86 (1H, d, J=4.6 Hz) 7.27-7.33 (1H, m) 7.49 (1H, dd, J=8.2, 5.2 Hz) 7.76 (1H, dd, J=8.2, 2.8 Hz).

Intermediate 16

2-(Aminomethyl)-5-fluoro-N-methylbenzenesulfonamide hydrochloride. To a solution of 2-azidomethyl-5-fluoro-N-methyl-benzenesulfonamide (560 mg, 2.3 mmol) in ethanol (10 mL) was added 6N HCl (1 mL) and 10% Pd—C (100 mg) and the mixture hydrogenated with 1 atm of H$_2$ for 14 hrs. The catalyst was removed by filtration through Celite® and the filtrate concentrated in vacuo to provide 630 mg (Yield >100%) of the title compound. $^1$H NMR (500 MHz, DMSO-D6) δ ppm: 4.36 (2H, d, J=5.2 Hz) 7.63-7.70 (2H, m) 7.77-7.83 (1H, m) 8.11 (1H, d, J=4.9 Hz) 8.41 (3H, s); LC/MS m/z 219 (M+H).

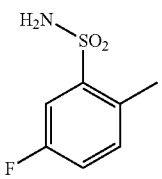

Intermediate 17

5-Fluoro-2-methyl-benzenesulfonamide. To a solution of 5-fluoro-2-methyl-benzenesulfonyl chloride (4.18 g, 20 mmol) in acetone (20 mL) was added, dropwise, concentrated NH$_4$OH (3 mL) and the resulting mixture stirred for 5 min. Acetone was removed in vacuo and the precipitates were filtered, washed thoroughly with water and dried in vacuo to provide 3.7 g (Yield 98%) of the title compound as a white solid; $^1$H NMR (500 MHz, DMSO-D6) δ ppm: 2.55 (3H, s) 7.33-7.40 (1H, m) 7.40-7.46 (1H, m) 7.54 (2H, s) 7.59 (1H, dd, J=9.2, 2.7 Hz); LC/MS m/z 190 (M+H).

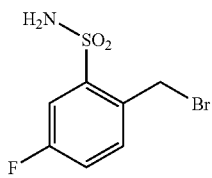

Intermediate 18

2-Bromomethyl-5-fluoro-benzenesulfonamide. $^1$H NMR (500 MHz, CDCl$_3$) δ ppm: 5.01 (2H, s) 5.16 (2H, brs) 7.25-7.31 (1H, m) 7.53 (1H, dd, J=8.5, 5.2 Hz) 7.80 (1H, dd, J=8.5, 2.7 Hz). LC/MS m/z 268/270 (M+H).

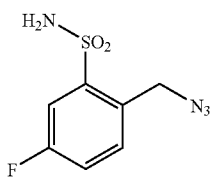

Intermediate 19

2-Azidomethyl-5-fluoro-N-methyl-benzenesulfonamide. $^1$H NMR (300 MHz, CDCl$_3$) δ ppm: 4.82 (2H, s) 5.18 (2H, s) 7.27 (1H, m) 7.45 (1H, dd, J=8.4, 5.5 Hz) 7.79 (1H, dd, J=8.4, 2.6 Hz). LC/MS m/z 253 (M+Na).

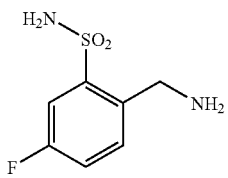

Intermediate 20

2-(Aminomethyl)-5-fluorobenzenesulfonamide hydrochloride. $^1$H NMR (500 MHz, DMSO-D6) δ ppm: 4.05 (2H, s) 5.05 (3H, br) 7.44 (1H, dt, J=8.5, 3 Hz) 7.58 (1H, dd, J=9.2, 2.7 Hz) 7.66 (1H, dd, J=8.5, 5.5 Hz). LC/MS m/z 205 (M+H).

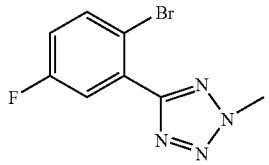

Intermediate 21

5-(2-Bromo-5-fluoro-phenyl)-2-methyl-2H-tetrazole: A mixture of 5-(2-bromo-5-fluoro-phenyl)-1H-tetrazole (1.0 g, 4.12 mmol; Butt Park Ltd.), methyl iodide (1.12 g, 10 mmol) and potassium carbonate (1.5 g) in DMF (5 mL) was stirred at room temperature for 16 hrs, and the mixture concentrated in vacuo. The resulting residue was purified by column chromatography (SiO$_2$, CH$_2$Cl$_2$) to provide 650 mg (2.53 mmol, yield 61%) of the title compound as a white powder (fast-moving 2-Me isomer): TLC, Rf 0.7 (CH$_2$Cl$_2$); $^1$H NMR (500 MHz, CDCl$_3$) δ 4.45 (3H, s) 7.03-7.11 (1H, m) 7.63 (1H, dd, J=8.9, 3.1 Hz) 7.69 (1H, dd, J=8.9, 5.5 Hz); $^{13}$C NMR (126 MHz, CDCl$_3$) δ 39.86 (s) 116.28 (s) 118.66 (d, J=22 Hz) 118.76 (d, J=25 Hz) 130.13 (d, J=8.6 Hz) 135.73 (d, J=8.6 Hz) 161.74 (d, J=247.6 Hz) 163.53 (s); LC/MS m/z 257/259.

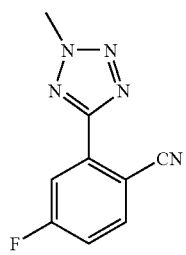

Intermediate 22

4-Fluoro-2-(2-methyl-2H-tetrazol-5-yl)-benzonitrile. A mixture of 5-(2-bromo-5-fluoro-phenyl)-2-methyl-2H-tetrazole (650 mg, 2.53 mmol) and CuCN (224 mg, 2.5 mmol) in dimethylformamide (4 mL) was placed in a sealed tube and heated at 100-110° C. for 20 hrs. After cooling, the insoluble material was filtered, and the filtrate concentrated in vacuo. The residue was dissolved in CH$_2$Cl$_2$, washed with aq. 4N HCl and dil. NH$_4$OH, then dried (MgSO$_4$), filtered, and concentrated. The residual solid was purified by column chromatography (SiO$_2$, CH$_2$Cl$_2$) to obtain 375 mg (Yield 73%) of the title compound as an off-white solid; $^1$H NMR (500 MHz, CDCl$_3$) δ ppm: 4.48 (3H, s) 7.29 (1H, dd, J=7.6, 2.8 Hz) 7.85 (1H, dd, J=8.6, 5.2 Hz) 8.00 (1H, dd, J=9.0, 2.6 Hz); LC/MS m/z 204.

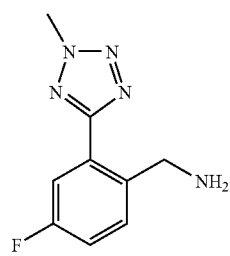

Intermediate 23

(4-Fluoro-2-(2-methyl-2H-tetrazol-5-yl)phenyl)methanamine hydrochloride. A solution of 4-fluoro-2-(2-methyl-2H-tetrazol-5-yl)-benzonitrile, (330 mg, 1.62 mmol) in ethanol (15 mL) was mixed with 6N HCl (1 mL) and 10% Pd—C (200 mg) under nitrogen. The mixture was then stirred under hydrogen (1 atm) for 3 hrs. After removing the catalyst, the filtrate was concentrated in vacuo to provide 360 mg (Yield 91%) of the title compound as an off-white solid; $^1$H NMR (500 MHz, DMSO-D6) δ ppm: 4.42 (2H, d, J=2.75 Hz) 4.49 (3H, s) 7.48-7.56 (1H, m) 7.78 (1 H, dd, J=8.7, 5.7 Hz) 7.86 (1H, dd, J=9.8, 2.8 Hz) 8.45 (3H, s); LC/MS m/z 208.

Intermediate 24

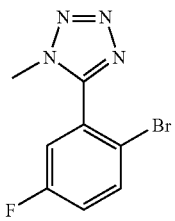

5-(2-Bromo-5-fluoro-phenyl)-1-methyl-2H-tetrazole. A mixture of 5-(2-bromo-5-fluoro-phenyl)-1H-tetrazole (1.0 g, 4.12 mmol), iodomethane (1.12 g, 10 mmol) and potassium carbonate (1.5 g) in dimethylformamide (5 mL) was stirred at room temperature for 16 hrs, then concentrated in vacuo. The residue was purified by column chromatography (SiO$_2$, CH$_2$Cl$_2$) to provide 350 mg (Yield 33%) of the title compound as white crystals. $^1$H NMR (500 MHz, CDCl$_3$) δ ppm: 4.00 (3H, s) 7.18-7.25 (2H, m) 7.72 (1H, dd, J=8.4, 5.0 Hz); $^{13}$C NMR (126 MHz, CDCl$_3$) δ ppm: 34.59, 117.73, 119.58, 120.43, 127.57, 135.11, 153.43, 161.69. LC/MS m/z 257/259.

Intermediate 25

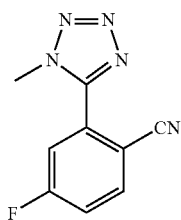

4-Fluoro-2-(1-methyl-2H-tetrazol-5-yl)-benzonitrile. $^1$H NMR (300 MHz, CDCl$_3$) δ ppm: 4.13 (3H, s) 7.38-7.49 (2H, m) 7.86-7.97 (1H, m); LC/MS m/z 204 (M+H).

Intermediate 26

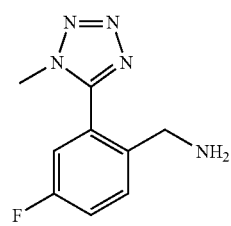

(4-Fluoro-2-(1-methyl-2H-tetrazol-5-yl)phenyl)methanamine hydrochloride. $^1$H NMR (500 MHz, DMSO-D6) δ ppm: 4.05 (2H, s) 4.09 (3H, s) 7.58-7.67 (1H, m) 7.77 (1H, dd, J=9.3, 2.6 Hz) 7.87 (1H, dd, J=8.7, 5.7 Hz) 8.38 (3H, s); LC/MS m/z 208.

Intermediate 27

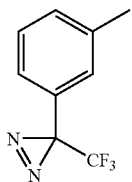

3-m-Tolyl-3-trifluoromethyl-3H-diazirine. To a cold stirring solution of 3-m-tolyl-3-trifluoromethyl-diaziridine (2.0 g, 10 mmol. prepared using the methods described in Doucet-Personeni C. et al., *J. Med. Chem.*, 2001, 44, 3203 and Nassal, M. *Liebigs Ann. Chem.* 1983, 1510-1523 or in Stromgaard, K et al., *J. Med. Chem.*, 2002, 45, 4038-46) in ethanol (20 mL) was added triethylamine (1.5 g, 15 mmol). To this was added tert-butyl hypochlorite (3.25 g, 30 mmol), and the mixture stirred for 5 min. This mixture was poured into 10% aqueous sodium sulfite (100 mL), and extracted with ether. The ether extract was washed with brine, dried (MgSO$_4$), filtered and concentrated. The residue was purified by column chromatography (SiO$_2$, pentane) to provide 1.6 g (Yield 80%) of the title compound. $^1$H NMR (300 MHz, CDCl$_3$) δ ppm: 2.33 (3H, s) 6.90-7.03 (2H, m) 7.15-7.31 (2H, m).

Intermediate 28

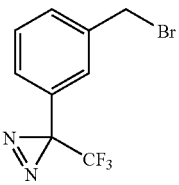

3-(3-Bromomethyl-phenyl)-3-trifluoromethyl-3H-diazirine. To a solution of 3-m-tolyl-3-trifluoromethyl-3H-diazirine (200 mg, 1 mmol) in CCl$_4$ (4 mL) was added N-bromosuccinimide (200 mg, 1.1 mmol, re-crystallized from water), and the stirred mixture heated at 85° C. To this was added AIBN (50 mg) and the mixture heated at reflux for an additional 2.5 hrs. After cooling, the mixture was purified by column chromatography (SiO$_2$, pentane) to provide 150 mg (Yield 54%) of the title compound as a clear oil. $^1$H NMR (300 MHz, CDCl$_3$) δ ppm: 4.42 (2H, s) 7.10-7.17 (2H, m) 7.31-7.45 (2H, m).

Intermediate 29

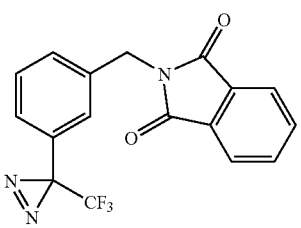

2-[3-(3-Trifluoromethyl-diaziridin-3-yl)-benzyl]-isoindole-1,3-dione. A mixture of 3-(3-bromomethyl-phenyl)-3-trifluoromethyl-3H-diazirine, (140 mg, 0.5 mmol) and potassium phthalimide (95 mg, 0.5 mmol) in dimethylformamide (1.5 mL) was stirred at room temperature for 3 hrs. Dimethylformamide was removed in vacuo. The residue was extracted with CH$_2$Cl$_2$, washed with water, then dried (Na₂SO₄), filtered, and concentrated. The resulting residue was purified by column chromatography (SiO₂, 1:1 CH₂Cl₂/pentane) to provide 140 mg (Yield 82%) of the title compound as a solid; $^1$H NMR (300 MHz, CDCl₃) δ ppm: 4.80 (2H, s) 7.09-7.21 (2H, m) 7.32 (1H, t, J=7.9 Hz) 7.41-7.49 (2H, m) 7.66-7.71 (2H, m) 7.81-7.85 (2H, m); LC/MS m/z 346 (M+H).

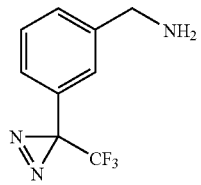

Intermediate 30

(3-(3-(Trifluoromethyl)diaziridin-3-yl)phenyl)methanamine. A stirred solution of 2-[3-(3-trifluoromethyl-diaziridin-3-yl)-benzyl]-isoindole-1,3-dione, (150 mg, 0.43 mmol) in ethanol (2 mL) was treated with hydrazine hydrate (0.4 mL) at room temperature and the solution stirred for 3.5 hrs. After removing ethanol in vacuo, the residue was partitioned between CH₂Cl₂ and water. The aqueous phase was acidified with dilute HCl, and washed with CH₂Cl₂. The aqueous phase was basified with dilute NaOH, and extracted with CH₂Cl₂. The organic extract was dried (MgSO₄), filtered, and concentrated to obtain 50 mg (Yield 54%) of (3-(3-(trifluoromethyl)diaziridin-3-yl)phenyl)methanamine and (3-(3-(trifluoromethyl)-3H-diazirin-3-yl)phenyl)methanamine as a 1:1 mixture; $^1$H NMR (300 MHz, CDCl₃) δ ppm: 3.85 (2H, s) 3.88 (2H, s) 7.08 (2H, s) 7.31-7.40 (4H, m) 7.43-7.50 (1H, m, J=6.2 Hz) 7.54 (1H, s); LC/MS m/z 216 (M+H for diazirine) and 218 (M+H for diaziridine).

Intermediates 31-32

4-Fluoro-2-(1H-1,2,4-triazol-1-yl)benzonitrile and 4-(1H-1,2,4-triazol-1-yl)-2-fluorobenzonitrile. To a solution of 2,4-difluorobenzonitrile (10 g, 72 mmol) dissolved in tetrahydrofuran (20 mL), and dimethylformamide (40 mL) was added the sodium salt of 1,2,4-triazole (6.3 g, 70 mmol) and the mixture was stirred at 90° C. for 3 h, filtered and concentrated. The residue was adsorbed onto Silica gel and purified by flash chromatography eluting with 0%-10%-30% ethylacetate/hexanes to give 4-fluoro-2-(1H-1,2,4-triazol-1-yl)benzonitrile as colorless needles (2.46 g, 18%) and 4-(1H-1,2,4-triazol-1-yl)-2-fluorobenzonitril as a white solid (0.746 g, 6%).

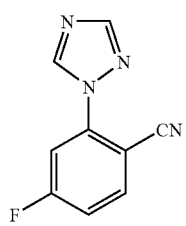

Intermediate 31

4-Fluoro-2-(1H-1,2,4-triazol-1-yl)benzonitrile. Colorless needles (2.46 g, 18% yield) $^1$H NMR (500 MHz, CDCl₃) δ 8.89 (1H, s), 8.19 (1H, s), 7.85 (1H, dd, J=8.7, 5.6 Hz), 7.60 (1H, dd, J=8.8, 2.4 Hz), 7.28-7.24 (1H, m). LCMS (M+H) calcd for C₉H₆N₄F: 189.05; found: 189.13.

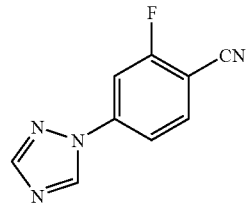

Intermediate 32

4-(1H-1,2,4-Triazol-1-yl)-2-fluorobenzonitrile. White solid (0.746 g, 6% yield) $^1$H NMR (500 MHz, CDCl₃) δ 8.66 (1H, s), 8.15 (1H, s), 7.79 (1H, dd, J=8.5, 6.7 Hz), 7.69 (1H, dd, J=9.5, 1.8 Hz), 7.65-7.63 (1H, m). LCMS (M+H) calcd for C₉H₆N₄F: 189.05; found: 189.13.

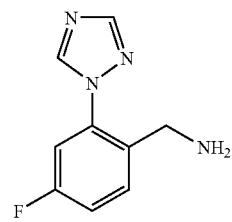

Intermediate 33

(4-Fluoro-2-(1H-1,2,4-triazol-1-yl)phenyl)methanamine hydrochloride). 4-Fluoro-2-(1H-1,2,4-triazol-1-yl)benzonitrile, (2.46 g, 13.13 mmol) was dissolved in hot ethanol (150 mL). To this was added 1N HCl (15 mL) followed by 10% Pd—C (200 mg). The mixture was treated with H₂ at 55 psi for 4 h in a Parr shaker then filtered over Celite® and the solvent removed under reduced pressure. The resulting residue was partitioned between ethyl acetate and water. The aqueous phase was separated and lyophilized to afford the title compound as a white powder (2.96 g, 99% yield). $^1$H NMR (500 MHz, CD₃OD) δ ppm: 9.51 (1H, s), 8.63 (1H, s), 7.85 (1H, dd, J=8.5, 5.8 Hz), 7.68 (1H, dd, J=8.8, 2.4 Hz), 7.49 (1H, td, J=8.3, 2.4 Hz), 4.20 (2H, s). LCMS (M+H) calcd for C₉H₁₀N₄F: 193.08; found: 193.16.

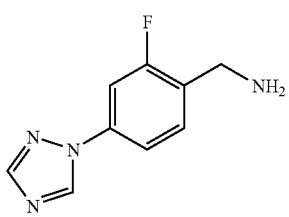

Intermediate 34

(2-Fluoro-4-(1H-1,2,4-triazol-1-yl)phenyl)methanamine hydrochloride. This compound was prepared (79% yield) following the procedure for (4-fluoro-2-(1H-1,2,4-triazol-1-yl)phenyl)methanamine hydrochloride using (2-fluoro-4-(1H-1,2,4-triazol-1-yl)benzonitrile. $^1$H NMR (500 MHz, CD₃OD) δ: 9.25 (1H, s), 8.46 (1H, s), 7.80 (1H, dd, J=8.6, 5.8 Hz), 7.64 (1H, dd, J=8.8, 2.4 Hz), 7.44 (1H, td, J=8.3, 2.6 Hz), 4.17 (2H, s). LCMS (M+H) calcd for C₉H₁₀N₄F: 193.08; found: 193.16.

Intermediate 35

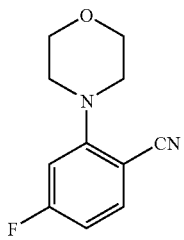

4-Fluoro-2-morpholinobenzonitrile. $^1$H NMR (500 MHz, CDCl$_3$) δ ppm: 7.55 (1H, dd, J=8.5, 6.4 Hz), 6.71 (1H, td, J=8.1, 2.3 Hz), 6.67 (1H, dd, J=11.0, 2.4 Hz), 3.88 (4H, t, J=4.6 Hz), 3.22 (4H, t, J=4.6 Hz). LCMS (M+H) calcd for C$_{11}$H$_{12}$N$_2$OF: 207.09; found: 207.19.

Intermediate 36

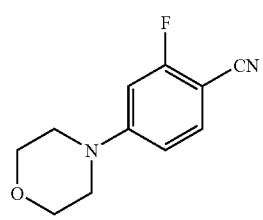

4-Morpholino-2-fluorobenzonitrile. $^1$H NMR (500 MHz, CDCl$_3$) δ ppm: 7.42 (1H, dd, J=8.8, 7.6 Hz), 6.63 (1H, dd, J=8.8, 2.4 Hz), 6.56 (1H, dd, J=12.8, 2.4 Hz), 3.84 (4H, t, J=4.9 Hz), 3.28 (4H, t, J=4.9 Hz). LCMS (M+H) calcd for C$_{11}$H$_{12}$N$_2$OF: 207.09; found: 207.19.

Intermediate 37

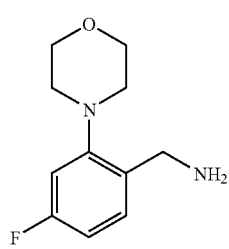

(4-Fluoro-2-morpholinophenyl)methanamine hydrochloride. $^1$H NMR (500 MHz, CDCl$_3$) δ ppm: 7.54 (1H, t, J=7.3 Hz), 7.20 (1H, dd, J=10.5, 2.0 Hz), 7.05-7.02 (1H, m), 4.28 (2H, s), 3.93 (4H, bs), 3.03 (4H, bs). LCMS (M+H) calcd for C$_{11}$H$_{16}$N$_2$OF: 211.12; found: 211.23.

Intermediate 38

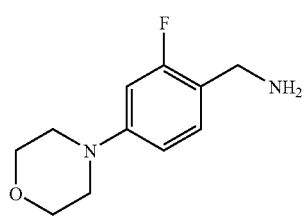

(2-Fluoro-4-morpholinophenyl)methanamine hydrochloride. $^1$H NMR (500 MHz, CD$_3$OD) δ ppm: 7.73 (1H, t, J=8.2 Hz), 7.62 (1H, d, J=7.6 Hz), 7.58 (1H, d, J=8.2 Hz), 4.26 (2H, s), 4.11 (4H, t, J=4.4 Hz), 3.65 (4H, t, J=4.4 Hz). LCMS (M+H) calcd for C$_{11}$H$_{16}$N$_2$OF: 211.12; found: 211.23.

Intermediate 39

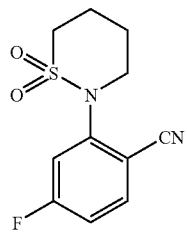

4-Fluoro-2-(1,1-dioxo-1λ$^6$-[1,2]thiazinan-2-yl)benzonitrile. To a mixture of 2,4-difluorobenzonitrile (10.0 g, 72 mmol) and 1,1-dioxo-1λ6-[1,2]thiazin-2-ane (8.84 g, 65.4 mmol) in 1:1 tetrahydrofuran/dimethylformamide (40 mL) was added potassium carbonate (9.0 g, 65.4 mmol). The mixture was stirred at 90° C. for 18 h then filtered and concentrated. The residue was purified by flash chromatography (SiO$_2$) eluting with 10%-50% ethyl acetate/hexanes followed by recrystallization from hot ethyl acetate/hexane to give the title compound as white needles (0.537 g, 3% yield). $^1$H NMR (500 MHz, CD$_3$OD) δ ppm: 7.70 (1H, dd, J=8.8, 5.8 Hz), 7.30 (1H, dd, J=8.8, 2.4 Hz), 7.15-7.12 (1H, m), 3.27 (2H, t, J=5.3 Hz), 3.33 (2H, t, J=6.1 Hz), 2.40-2.35 (2H, m), 2.05-2.01 (2H, m). LCMS (M+H) calcd for C$_{11}$H$_{16}$N$_2$OF: 255.06; found: 255.19.

Intermediate 40

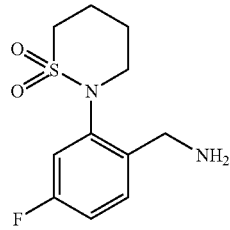

(4-Fluoro-2-(1,1-dioxo-1λ$^6$-[1,2]thiazinan-2-yl)phenyl)methanamine hydrochloride. 4-Fluoro-2-(1,1-dioxo-1λ$^6$-[1,2]thiazinan-2-yl)benzonitrile (1.37 g, 5.4 mmol) was dissolved in ethanol (120 mL). To this was added 1N HCl (20 mL) and a catalytic amount of 10% Pd—C. The mixture was shaken under hydrogen at 55 psi for 4 h then filtered through Celite® and concentrated to give the title compound as white solid (1.58 g, 100% yield). $^1$H-NMR (300 MHz, CD$_3$OD) δ ppm: 7.61 (1H, dd, J=8.4, 6.2 Hz), 7.38 (1H, dd, J=9.3, 2.7 Hz), 7.28 (1H, td, J=8.2, 2.7 Hz), 7.26 (2H, dd, J=21.4, 13.7 Hz), 3.93-3.84 (1H, m), 3.50-3.41 (3H, m), 2.40-2.31 (2H, m), 2.04-1.96 (2H, m). LCMS [M+H]$^+$ calcd for C$_{11}$H$_{16}$N$_2$O$_6$FS: 259.087; found: 259.24.

Intermediates 41-42

To a solution of 1H-1,2,3-triazole (3.5 g, 50.7 mmol) in tetrahydrofuran (10 mL) and dimethylformamide (20 mL) was added, portionwise, NaH (1.3 g, 51 mmol, 95%). The mixture was stirred at room temp for 30 min. 2,4-Difluorobenzonitrile (7.6 g, 55 mmol) was added and the mixture stirred at 85° C. for 3 h. The white mixture was concentrated and purified by flash chromatography eluting with 0% to 10% ethyl acetate/hexanes to give intermediates 41 and 42.

Intermediate 41

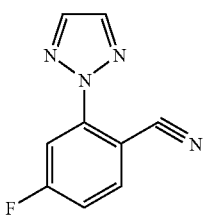

4-Fluoro-2-1,2,3-triazol-2-yl-benzonitrile. White needles (0.34 g, 3% yield). 1H-NMR (300 MHz, CDCl$_3$) δ ppm: 7.92 (2H, s), 7.88-7.79 (2H, m), 7.19-7.12 (1H, m). LCMS [M+H]$^+$ calcd for C$_9$H$_6$N$_4$F: 189.05; found: 189.12.

Intermediate 42

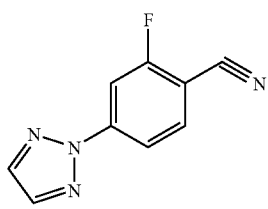

2-Fluoro-4-1,2,3-triazol-2-yl-benzonitrile. White solid (0.097 g, 1% yield). $^1$H-NMR (300 MHz, CDCl$_3$) δ ppm: 8.03-7.95 (2H, m), 7.86 (2H, s), 7.74-7.69 (1H, m).

Intermediate 43

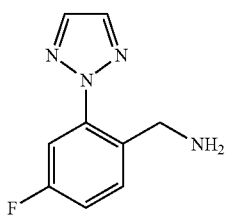

4-Fluoro-2-1,2,3-triazol-2-yl-benzylamine hydrochloride. 4-Fluoro-2-1,2,3-triazol-2-yl-benzonitrile, (0.34 g, 1.8 mmol) was dissolved in ethanol (50 mL). 1N HCl (10 mL) was added along with a catalytic amount of 10%-Pd—C. The mixture was shaken under H$_2$ at 55 psi for 4 h after which it was filtered through Celite® and concentrated to give the title compound as the corresponding HCl salt. Yellow solid (0.402 g, 98% yield). $^1$H-NMR (500 MHz, CD$_3$OD) δ ppm: 8.13 (2H, s), 7.87 (1H, dd, J=4.9, 2.6 Hz), 7.73 (1H, dd, J=4.9, 2.6 Hz), 7.34 (1H, td, J=8.2, 2.7 Hz), 4.35 (2H, s). LCMS [M+H]$^+$ calcd for C$_9$H$_{10}$N$_4$F: 193.08; found: 193.16.

Intermediate 44

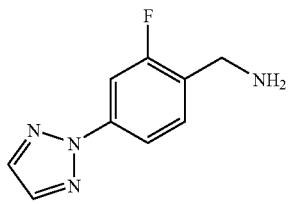

(2-Fluoro-4-(2H-1,2,3-triazol-2-yl)phenyl)methanamine. $^1$H-NMR (300 MHz, CD$_3$OD) δ ppm: 8.05-7.96 (2H, m), 8.00 (2H, s), 7.68 (1H, t, J=8.2 Hz), 4.26 (2H, s). LCMS [M+H]$^+$ calcd for C$_9$H$_{10}$N$_4$F: 193.08; found: 193.14.

Intermediates 45-48

A solution of 2,4-difluorobenzonitrile (7.07 g, 50.8 mmol) and 3-methyl-1H-1,2,4-triazole (4.22 g, 50.8 mmol) in N,N-dimethylformamide (45 ml) was treated with powdered anhydrous potassium carbonate (10 g) and the resulting mixture stirred at 22° C. for 18 h. The solid was then filtered and the filtrate concentrated in vacuo. The residue was diluted with ethyl acetate, washed with water and brine, then dried over anhydrous magnesium sulfate and concentrated. The resulting mixture was purified by a combination of chromatography on silica gel (elution gradient of ethyl acetate in hexane) and reversed phase silica gel to yield intermediates 45-48.

Intermediate 45

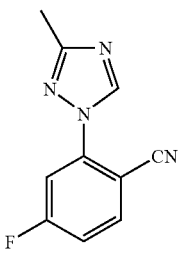

4Fluoro-2-(3-methyl-1H-1,2,4-triazol-1-yl)benzonitrile. White crystals (ethyl acetate-hexane); mp 117-118° C. $^1$HNMR 400 MHz (CDCl$_3$) δ ppm: 2.54 (3H, s, CH$_3$), 7.24 (1H, m, CH), 7.62 (1H, dd, J=2.5 Hz and J=9.1 Hz, CH), 7.84 (1H, dd, J=5.6 Hz and J=8.6 Hz, CH), 8.82 (1H, s, CH). Anal. Calcd for C$_{10}$H$_7$FN$_4$: C 59.40, H 3.49, N 27.71; Found: C 59.25, H 3.32, N 27.81.

Intermediate 46

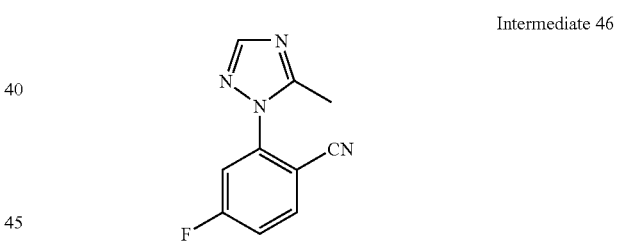

4-Fluoro-2-(5-methyl-1H-1,2,4-triazol-1-yl)benzonitrile. White crystals (ethyl acetate-hexane); mp 120-121° C. $^1$HNMR 400 MHz (CDCl$_3$) δ ppm: 2.56 (3H, s, CH$_3$), 7.30 (1H, dd, J=2.5 Hz and J=8.1 Hz, CH), 7.39 (1H, m, CH), 7.91 (1H, dd, J=5.5 Hz and J=8.6 Hz, CH), 8.06 (1H, s, CH). Anal. Calcd for C$_{10}$H$_7$FN$_4$: C 59.40, H 3.49, N 27.71; Found: C 59.35, H 3.70, N 27.77.

Intermediate 47

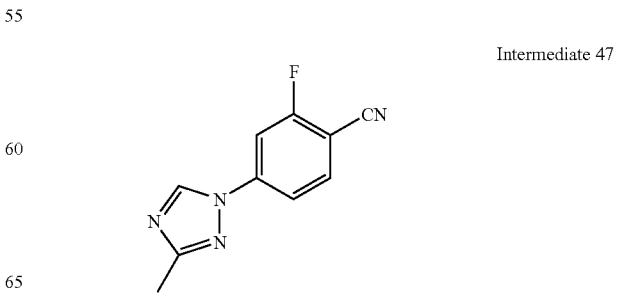

2-Fluoro-4-(3-methyl-1H-1,2,4-triazol-1-yl)benzonitrile. White crystals (ethyl acetate-hexane); mp 133-134° C. ¹HNMR 400 MHz (CDCl₃) δ ppm: 2.52 (3H, s, CH₃), 7.61 (1H, dd, J=2 Hz and J=9.1 Hz, CH), 7.67 (1H, dd, J=2 Hz and J=9.6 Hz, CH), 7.79 (1H, dd, J=6.5 Hz and J=8.6 Hz, CH), 8.56 (1H, s, CH). Anal. Calcd for C₁₀H₇FN₄: C 59.40, H 3.49, N 27.71; Found: C 59.42, H 3.24, N 28.41.

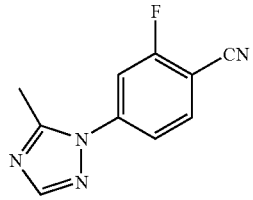

Intermediate 48

2-Fluoro-4-(5-methyl-1H-1,2,4-triazol-1-yl)benzonitrile. White crystals (ethyl acetate-hexane); mp 89-90° C., ¹HNMR 400 MHz (CDCl₃) δ ppm: 2.69 (3H, s, CH₃), 7.49-7.55 (2H, m, 2×CH), 7.83 (1H, dd, J=6.8 Hz and J=8.8 Hz, CH), 8.00 (1H, s, CH). Anal. Calcd for C₁₀H₇FN₄: C 59.40, H 3.49, N 27.71; Found: C 59.17, H 3.22, N 28.01.

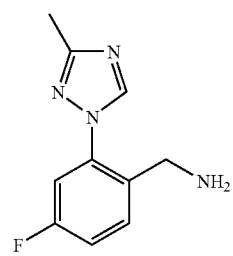

Intermediate 49

(4-Fluoro-2-(3-methyl-1H-1,2,4-triazol-1-yl)phenyl) methanamine hydrochloride salt. Hydrogenation of 4-fluoro-2-(3-methyl-1H-1,2,4-triazol-1-yl)benzonitrile (0.680 g, 3.36 mmol) gave 0.720 g (88% yield) of the title hydrochloride salt as a white solid. ¹HNMR 400 MHz (DMSO-d₆) δ ppm: 2.40 (3H, s, CH₃), 4.02 (2H, m, NCH₂), 7.50 (1H, m, CH), 7.62 (1H, dd, J=2.8 Hz and J=9.3 Hz, CH), 7.84 (1H, dd, J=6.1 Hz and J=9.1 Hz, CH), 9.00 (1H, s, CH). HRMS (ESI⁺) calculated for C₁₀H₁₂FN₄ [M+H⁺]: 207.1046; found: 207.1047.

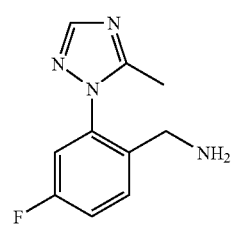

Intermediate 50

(4-Fluoro-2-(5-methyl-1H-1,2,4-triazol-1-yl)phenyl) methanamine hydrochloride salt. Hydrogenation of 4-fluoro-2-(5-methyl-1H-1,2,4-triazol-1-yl)benzonitrile, (0.244 g, 1.20 mmol) gave 0.290 g (100% yield) of the title hydrochloride salt as a white solid. ¹HNMR 400 MHz (DMSO-d6) δ ppm: 2.42 (3H, s, CH₃), 3.78 (2H, m, NCH₂), 7.58 (1H, m, CH), 7.67 (1H, dd, J=2.8 Hz and J=9.3 Hz, CH), 7.90 (1H, dd, J=6.0 Hz and J=8.6 Hz, CH), 8.22 (1H, s, CH). HRMS (ESI⁺) calculated for C₁₀H₁₂FN₄ [M+H⁺]: 207.1046; found: 207.1041.

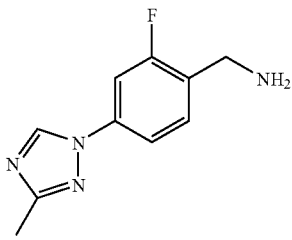

Intermediate 51

(2-Fluoro-4-(3-methyl-1H-1,2,4-triazol-1-yl)phenyl) methanamine hydrochloride salt. Hydrogenation of 2-fluoro-4-(3-methyl-1H-1,2,4-triazol-1-yl)benzonitrile, (0.220 g, 1.09 mmol) gave 0.260 g (98% yield) of the title hydrochloride salt as a white solid. ¹HNMR 400 MHz (DMSO-d₆) δ ppm: 2.38 (3H, s, CH₃), 4.09 (2H, m, NCH₂), 7.75-7.8 (2H, m, 2 xCH), 7.83 (1H, dd, J=2 Hz and J=9 Hz, CH), 9.29 (1H, s, CH). MS (ESI⁺) m/e 207 [M+H⁺].

An alternative procedure for the preparation of intermediate 50 is provided below.

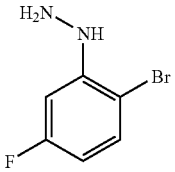

Intermediate 52

(2-Bromo-5-fluoro-phenyl)-hydrazine. To a suspension of (2-bromo-5-fluoro-phenyl)-hydrazine hydrochloride (41 g, 0.17 mol; prepared from 2-bromo-5-fluoroaniline by the method described in U.S. Pat. No. 3,959,309 (1976) p-23, and p-48) in water (300 mL) and CH₂Cl₂ (200 mL) was added 1N—NaOH (200 mL) until the solution was basic. The CH₂Cl₂ layer was separated and the aqueous portion was further extracted with CH₂Cl₂ (150 mL). The combined organic extracts were dried (MgSO₄), filtered, and concentrated to obtain 33 g (0.16 mol) of the title compound as an off-white powder: HPLC: 0.89 min (AP 97% at 220 nm); ¹H NMR (CDCl₃, 500 MHz) δ ppm 3.62 (2H, s, NH₂), 5.75 (1H, s, NH), 6.37 (1H, m, 5-CH), 6.87 (1H, dd, J=11, 3 Hz, 3-CH), 7.31 (1H, dd, J=8.6, 5.8 Hz, 6-CH); ¹³C NMR (CDCl₃, 125.8 Hz) δ ppm 100.0 (d, J=29 Hz, 3-CH), 101.4 (d, J=2.9 Hz, 1-C), 106.1 (d, J=23 Hz, 5-CH), 133.1 (d, J=9.6 Hz, 6-CH), 149.1 (d, J=10.6 Hz, 2-C), 163.5 (d, J=244 Hz, 4-CF); LC/MS m/z 205/207 (M+H).

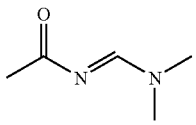

Intermediate 53

N-((dimethylamino)methylene)acetamide. To a suspension of acetamide (11.8 g, 200 mmol; Aldrich) in 1,4-dioxane (100 mL, 2 M, Sure Seal; Aldrich) was added dimethylformamide dimethyl acetal (37 mL, or 33.3 g, 0.28 mol; Aldrich or Alfa) and the mixture was placed in a water bath heated at 45-50° C. under slightly reduced pressure (~150 mmHg, rotary evaporator) to remove methanol (bp 65° C.) formed during the reaction. After near complete disappearance of acetamide (2-3 h, monitored by $^1$H NMR), the mixture was concentrated in vacuo at <40° C. to obtain 22.4 g (196 mmol, 98% yield) of the title compound as a clear colorless to an amber colored oil which crystallized on standing or in the freezer to provide soft-looking white crystals: HPLC RT 0.25 min (AP 100%); LC/MS m/z 115 (M+H); $^1$H NMR (CDCl$_3$, 500 MHz) δ ppm 2.19 (3H, s, 1-CH$_3$), 3.07 (3H, s, 4- or 5-NCH$_3$), 3.12 (3H, s, 4- or 5-NCH$_3$), 8.39 (1H, s, 3-CH); $^{13}$C NMR (CDCl$_3$, 125.8 MHz) δ ppm 27.1 (1-CH$_3$), 35.2 (4- or 5-NCH$_3$), 41.3 (4- or 5-NCH$_3$), 160.0 (3-CH), 184.8 (2-C=O); LRMS (ESI) m/z 115 (M+H).

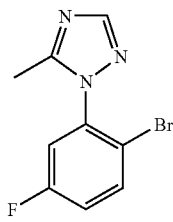

Intermediate 54

1-(2-Bromo-5-fluorophenyl)-5-methyl-1H-1,2,4-triazole. A procedure similar to that described in *J. Org. Chem.*, 1979, 44, 4160 was followed. To a solution of (2-bromo-5-fluorophenyl)-hydrazine (28 g, 136 mmol) in acetic acid (125 mL) was added a solution of N-((dimethylamino)methylene)acetamide (16.3 g, 143 mmol) in acetic acid (35 mL), and the mixture was stirred in an oil bath heated at 90° C. under nitrogen for 30 min. After cooling, the mixture was concentrated in vacuo to remove acetic acid, and the residue was partitioned between CH$_2$Cl$_2$ and an aqueous solution of K$_2$CO$_3$. The organic layer was separated, dried (Mg$_2$SO$_4$), filtered, and concentrated in vacuo to provide 35 g of an oil containing some solid impurities. This was re-dissolved in Et$_2$O and filtered to remove the insoluble by-products (~2 g). The filtrate was concentrated and the residue was purified by column chromatography (SiO$_2$, 1-2% MeOH/CH$_2$Cl$_2$) to obtain 8.8 g (34.4 mmol, 25% yield) of the title compound as an off-white crystalline solid after trituration with ether:: TLC: Rf 0.25 (10% EtOAc—CH$_2$Cl$_2$); Rf 0.45 (10% MeOH—CH$_2$Cl$_2$); HPLC: 1.68 min (AP 100% at 254 nm); LC/MS m/z 256/258 (M+H); $^1$H NMR (CDCl$_3$, 300 MHz) δ ppm 2.39 (3H, s, 9-Me), 7.13-7.18 (2H, m, 3,5-CH), 7.67-7.72 (1H, m, 6-CH), 8.00 (1H, s, 8-CH).

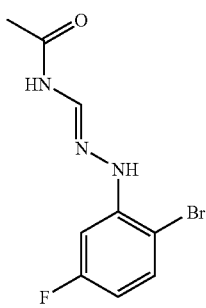

Intermediate 55

(E)-N-((2-(2-bromo-5-fluorophenyl)hydrazono)methyl) acetamide. To a solution of (2-bromo-5-fluoro-phenyl)-hydrazine hydrochloride (1.21 g, 5 mmol) in pyridine (3 mL) was added a solution of N-((dimethylamino)methylene)acetamide (600 mg, 5.26 mmol) in pyridine (2 mL) and the mixture stirred at room temperature under nitrogen for 1 h. The precipitate formed was collected, washed with CH$_2$Cl$_2$ and then with ether to obtain 1.15 g (3.16 mmol, 63% yield) of the title compound which was contaminated with 1 mole of dimethylamine hydrochloride as a white crystalline powder: HPLC: 2.22 min (AP 84% at 220 nm); LC/MS m/z 274/276 (M+H); $^1$H NMR (DMSO-d6, 500 MHz) δ ppm 2.00 (3H, s, 9-Me), 2.51 (6H, s, 2 N—CH$_3$), 6.45 (1H, dt, J=8.5, 3 Hz, 5-CH), 6.89 (1H, dd, J=12, 3 Hz, 3-CH), 7.43 (1H, dd, J=8.5, 6 Hz, 6-CH), 8.68 (1H, d, J=9.5 Hz, 7-CH), 8.88 (2H, br.s, NH$_2^+$), 9.24 (1H, s, 7-NH), 10.54 (1H, d, J=9.5 Hz, 2-NH); No signals from the rotational isomer were observed; $^{13}$C NMR (CDCl$_3$, 125.8 Hz) δppm 22.6 (9-CH$_3$), 33.9 (2 NCH$_3$), 99.6 (d, J=28 Hz, 3-CH), 99.7 (1-C), 105.0 (d, J=24 Hz, 5-CH), 133.5 (d, J=10.6 Hz, 6-CH), 137.1 (7-CH), 144.9 (d, J=11.6 Hz, 2-C), 162.4 (d, J=244 Hz, 4-CF), 168.5 (8-C=O). No signals from the rotational isomer were observed; Anal. calcd for C$_9$H$_9$BrFN$_3$O.Me$_2$NH.HCl.1/2H$_2$O: C36.24, H4.99, N15.37, found C35.88, H4.87, N15.23. An analytical sample of the title compound without contamination of dimethylamine hydrochloride was obtained by column purification (SiO$_2$, 10-15% EtOAc—CH$_2$Cl$_2$): TLC Rf 0.55 (20% EtOAc—CH$_2$Cl$_2$); HPLC: 2.17 min (AP 88% at 220 nm); LC/MS m/z 274/276 (M+H); $^1$H NMR (DMSO-d6, 500 MHz) δ ppm 1.99 (3H, s, 9-Me), 6.45 (1H, dt, J=8.5, 3 Hz, 5-CH), 6.88 (1H, dd, J=12, 3 Hz, 3-CH), 7.43 (1H, dd, J=9, 6 Hz, 6-CH), 8.69 (1H, d, J=9.5 Hz, 7-CH), 9.23 (1H, s, 7-NH), 10.52 (1H, d, J=9.5 Hz, 2-NH); About 16% of rotational isomer was also observed as a set of minor peaks: $^1$H NMR (DMSO-d6, 500 MHz) δ ppm 2.11 (3H, s, 9'-Me), 6.58 (1H, dt, J=8.5, 3 Hz, 5'-CH), 7.10 (1H, dd, J=11.6, 3 Hz, 3'-CH), 7.29 (1H, d, J=2.4 Hz, 7'-CH), 7.50 (1H, dd, J=8.7, 6 Hz, 6'-CH), 8.35 (1H, s, 2'-NH), 10.70 (1H, s, 7'-NH); $^{13}$C NMR (DMSO-d6, 125.8 Hz) δppm 22.6 (9-CH$_3$), 99.7 (d, J=29 Hz, 3-CH), 99.8 (d, J=3 Hz, 1-C), 105.0 (d, J=24 Hz, 5-CH), 133.6 (d, J=10.6 Hz, 6-CH), 137.1 (7-CH), 144.9 (d, J=11.6 Hz, 2-C), 162.5 (d, J=241 Hz, 4-CF), 168.5 (8-C=O); $^{13}$C NMR (DMSO-d6, 125.8 Hz) δ ppm 22.9 (9'-CH$_3$), 100.7 (d, J=3 Hz, 1'-C), 101.6 (d, J=29 Hz, 3'-CH), 106.8 (d, J=24 Hz, 5'-CH), 133.6 (d, J=9.6 Hz, 6'-CH), 162.4 (d, J=242 Hz, 4'-CF), 168.6 (8'-C=O); HRMS (ESI) calcd for C$_9$H$_{10}$BrFN$_3$O (M+H) 273.9991, found 274.0004 (δ+4.6 ppm); Anal. calcd for C$_9$H$_9$BrFN$_3$O: C39.43, H3.31, N29.15, found C39.67, H2.99, N29.09.

Alternatively, to a mixture of (2-bromo-5-fluoro-phenyl)-hydrazine hydrochloride (5.9 g, 28.8 mmol) and N-((dimethylamino)methylene)acetamide (3.30 g, 28.8 mmol) in THF (30 mL) was added 5 drops of HOAc, and the mixture stirred at room temperature under nitrogen for 15 min. The mixture was concentrated in vacuo, and the residue suspended in a mixture of ether (50 mL) and hexanes (50 mL) and the resulting precipitate collected and air-dried to provide 5.7 g of the title compound as an off-white powder. A second crop gave an additional 0.3 g.

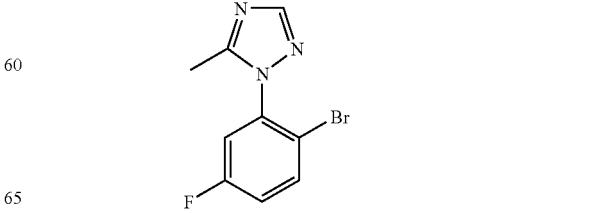

Intermediate 54

1-(2-bromo-5-fluorophenyl)-5-methyl-1H-1,2,4-triazole. A solution of 1-(2-bromo-5-fluoro-phenyl)-2-(N-acetylformamidinyl)hydrazine (987 mg, 2.71 mmol; containing one mole of Me₂NH.HCl and 0.5 mol of water) and pyridine hydrochloride (208 mg, 1.8 mmol; Aldrich) in pyridine (4 mL) was heated in an oil bath at 90° C. under nitrogen for 23 h. The mixture was concentrated in vacuo, and the residue partitioned between CH₂Cl₂ and water, filtering off any insoluble materials. The organic extract was washed with 1N HCl, then with brine, dried (Na₂SO₄), filtered and concentrated in vacuo to obtain 480 mg of a light brown oil which was purified by column chromatography (SiO₂, 2% MeOH/CH₂Cl₂) to provide 232 mg (0.91 mmol, 33% yield) of the title compound as an amber colored oil.

Alternatively, a solution of 1-(2-bromo-5-fluoro-phenyl)-2-(N-acetylformamidinyl)hydrazine (6.00 g, 21.9 mmol; obtained by HOAc method) and pyridine hydrochloride (1.27 mg, 11 mmol; Aldrich) in pyridine (60 mL) was heated in an oil bath at 90°-100° C. under nitrogen for 23 h. The mixture was concentrated in vacuo, and the residue partitioned between CH₂Cl₂ and 1N HCl. The organic extract was washed with brine, dried (MgSO₄), filtered and concentrated in vacuo to obtain 6.0 g of an oily solid which was dissolved in diethyl ether (40 mL) and filtered to remove insoluble material. After removal of the solvent, the residue was crystallized from Et₂O-hexanes to provide 2.21 g (8.63 mmol, 39% yield) of the title compound as a white crystalline solid. The mother liquor can be purified by column chromatography (SiO₂, 2% MeOH/CH₂Cl₂), followed by crystallization from Et₂O-hexanes to give additional amount of the title compound 7.

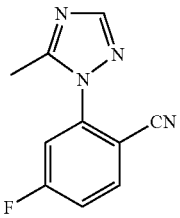

Intermediate 46

4-Fluoro-2-(5-methyl-1H-1,2,4-triazol-1-yl)benzonitrile. To a solution of 1-(2-bromo-5-fluorophenyl)-5-methyl-1H-1,2,4-triazole (4.1 g, 16 mmol) in N-methylpyrrolidone (NMP, 30 mL) was added copper (I) cyanide, CuCN (1.72 g, 19.2 mmol; Aldrich) and the mixture was stirred in an oil bath heated at 140-150° C. under a nitrogen atmosphere for 3 h. After cooling, the solvent was removed in vacuo and the residue mixed with CH₂Cl₂ (50 mL), water (50 mL), and conc-NH₄OH (50 mL). The mixture was stirred for 30 min, and the insoluble material was filtered through Celite®. The aqueous filtrate was extracted again with CH₂Cl₂. The combined CH₂Cl₂ filtrate and extracts were washed again with dilute NH₄OH, dried (MgSO₄), filtered and concentrated to a dark solid which was triturated with diethyl ether to give 1.6 g of the title compound as an off-white solid. An additional amount (750 mg) of the title compound was obtained from the mother liquor by column chromatography (SiO₂, 5% Et₂O—CH₂Cl₂) followed by trituration with Et₂O. Total yield, 2.35 g (11.6 mmol, 73% yield); HPLC: 1.29 min (AP 99% at 254 nm); LC/MS m/z 203 (M+H); ¹H NMR (CDCl₃, 500 MHz) δ ppm 2.50 (3H, s, 10-Me), 7.25 (1H, dd, J=8, 2.5 Hz, 3-CH), 7.30-7.36 (1H, m, 5-CH), 7.85 (1H, dd, J=8.8, 5.5 Hz, 6-CH), 8.00 (1H, s, 9-CH); ¹³C NMR (CDCl₃, 125.8 Hz) δ ppm 12.7 (10-Me), 107.2 (d, J=Hz, 1-C), 114.6 (7-CN), 116.2, (d, J=25 Hz, 3-CH), 117.9 (d, J=23 Hz, 5-CH), 136.1 (d, J=10 Hz, 6-CH), 141.5 (d, J=1 1 Hz, 2-C), 152.3 (9-CH), 153.9 (8-C), 164.9 (d, J=261 Hz, 4-CF).

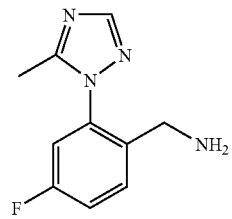

Intermediate 50

(4-Fluoro-2-(5-methyl-1H-1,2,4-triazol-1-yl)phenyl) methanamine hydrochloride. A solution of 4-fluoro-2-(5-methyl-1H-1,2,4-triazol-1-yl)benzonitrile (2.9 g, 14 mmol) in EtOH (100 mL) was mixed with 1N—HCl (15 mL) and 10% Pd—C (0.7 g, Aldrich). This mixture was hydrogenated in a Parr shaker at 45-55 psi of hydrogen for 20 h. The catalyst was filtered over Celite®, and washed with EtOH. The filtrate was concentrated, and the residue triturated with EtOH-Et₂O to obtain 3.17 g (13 mmol, 91% yield) of the title compound as an off-white powder: HPLC 0.47 min (AP 100% at 254 nm); LC/MS m/z 207 (M+H); ¹H NMR (DMSO-d6, 300 MHz) δ ppm 2.40 (3H, s, CH₃), 3.77 (2H, d, J=5.5 Hz, NCH₂), 7.52-7.62 (1H, m), 7.66 (1H, dd, J=9.2, 2.6 Hz), 7.87 (1H, t, J=7 Hz), 8.14 (1H, s), 8.47 (3H, brs, NH₃⁺).

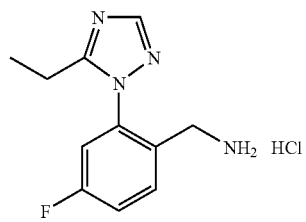

Intermediate 56

(2-(5-Ethyl-1H-1,2,4-triazol-1-yl)-4-fluorophenyl)methanamine hydrochloride ¹H NMR (300 MHz, DMSO-D6) δ ppm 1.21 (t, J=7.50 Hz, 3H) 2.69 (q, J=7.50 Hz, 2H) 3.64-3.81 (m, J=5.49 Hz, 2H) 7.42-7.71 (m, 2H) 7.75-7.91 (m, J=5.86 Hz, 1H) 8.17 (s, 1H) 8.31 (s, 3H)); LC/MS m/z 221 (M+H).

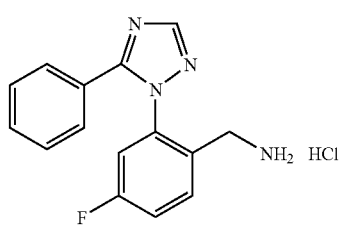

Intermediate 57

(4-Fluoro-2-(5-phenyl-1H-1,2,4-triazol-1-yl)phenyl) methanamine hydrochloride. ¹H NMR (300 MHz, DMSO-D6) δ ppm 3.84 (s, 2H) 7.24-7.64 (m, 4H) 7.79-7.94 (m, 2H) 7.87 (m, 1H) 8.39 (s, 1H) 8.48 (bs, 3H)); LC/MS m/z 269 (M+H).

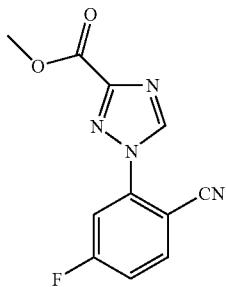

Intermediate 58

1-(2-Cyano-5-fluoro-phenyl)-1H-1,2,4-triazole-3-carboxylic acid methyl ester. To a solution of methyl 1H-1,2,4-triazole-3-carboxylate (27 g, 215 mmol) in dimethylformamide (170 mL) was added sodium hydride (5.53 g, 95%, 217 mmol) and the mixture was stirred for 30 min. Added to this was 2,4-difluorobenzylnitrile (30 g, 217 mmol) and the resulting mixture stirred at room temp for 60 h. The mixture was diluted with water and filtered to remove solids. The solution was extracted with ethyl acetate and the organic layer was washed with water (3X's) and brine, then dried ($Na_2SO_4$) and concentrated. The resulting residue was purified by flash chromatography ($SiO_2$) eluting with 30% tetrahydrofuran/20% $CH_2Cl_2$/50% hexane to give the title compound as white needles (5.34 g, 10% yield). $^1$H-NMR (300 MHz, $CDCl_3$) δ ppm: 8.92 (1H, s), 7.85 (1H, dd, J=8.8, 5.5 Hz), 7.67 (1H, dd, J=8.8, 2,6 Hz), 7.34-7.27 (1H, m), 40.3 (3H, s). LCMS [M+H]$^+$ calcd for $C_{11}H_8N_4FO_2$: 247.06; found: 247.11.

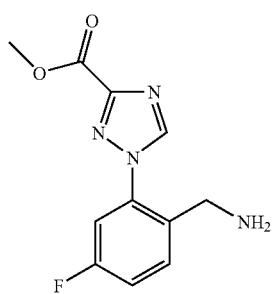

Intermediate 59

Methyl 1-(2-(aminomethyl)-5-fluorophenyl)-1H-1,2,4-triazole-3-carboxylate. The title compound can be prepared from intermediate 58, 1-(2-cyano-5-fluoro-phenyl)-1H-1,2,4-triazole-3-carboxylic acid methyl ester $^1$H-NMR (300 MHz, $CD_3OD$) δ ppm: 9.15 (1H, s), 7.80 (1H, dd, J=8.8, 5.9 Hz), 7.71 (1H, dd, J=8.8, 2.6 Hz), 7.46 (1H, td J=8.2, 2.6 Hz), 4.19 (2H, s), 4.03 (3H, s). LCMS [M+H]$^+$ calcd for $C_{11}H_{12}N_4O_2$: 251.09; found: 251.17.

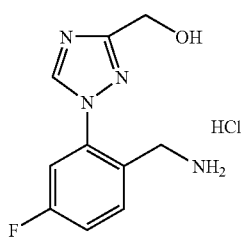

Intermediate 60

(1-(2-(Aminomethyl)-5-fluorophenyl)-1H-1,2,4-triazol-3-yl)methanol hydrochloride. 1-(2-cyano-5-fluoro-phenyl)-1H-1,2,4-triazole-3-carboxylic acid methyl ester (3.3 g, 13.4 mmol) was dissolved in 40 mL THF and treated with 26.8 mL of 1M LAH in THF dropwise. After 1 hr, 5 mL of saturated (aq.) $Na_2SO_4$ was cautiously added and the mixture was stirred overnight to decompose excess reagent. The suspension was filtered thru Celite® and the filtrate concentrated. The residue was dissolved in 50 mL abs ethanol and treated with 3 mL 6N HCl and concentrated. Trituration with $Et_2O$/$CH_3CN$ gave a total of 3.4 g (80%) of the alcohol hydrochloride as an amorphous solid. $^1$H NMR (300 MHz, DMSO-D6) δ ppm 4.00 (d, J=5.49 Hz, 2H) 4.56 (s, 2H) 7.40-7.90 (m, 3H) 8.54 (bs, 3H) 9.03 (s, 1H); LC/MS m/z 223 (M+H).

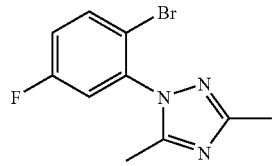

Intermediate 61

1-(2-Bromo-5-fluorophenyl)-3,5-dimethyl-1H-1,2,4-triazole. A mixture of 1-(2-bromo-5-fluoro-phenyl)-/hydrazine hydrochloride. (24.15 g, 100 mmol) and diacetamide (10.1 g, 100 mmol; Aldrich) in anhydrous pyridine (100 mL) was stirred in an oil bath heated at 125-130° C. under nitrogen for 2 h. After cooling the mixture was concentrated in vacuo to dryness, and the residue diluted with EtOAc (100 mL) was washed with water (50 mL), and then with brine (30 mL), dried ($Na_2SO_4$), filtered and concentrated to obtain 24.2 g (90.3 mmol, yield 90%) of the title compound as a light brown oil: HPLC 1.59 min (AP 94% at 220 nm); LC/MS m/z 270/272 (M+H); $^1$H NMR ($CDCl_3$, 500 MHz) δ ppm 2.30 (3H, s, 9-Me), 2.39 (3H, s, 10-Me), 7.10-7.15 (2H, m, 3,5-CH), 7.67 (1H, dd, J=8.5, 5.5 Hz, 6-H); $^{13}$C NMR ($CDCl_3$, 125.8 Hz) δppm 12.4 (9-$CH_3$), 13.8 (10-Me), 116.5 (d, J=4 Hz, 1-C), 117.2, (d, J=24 Hz, 3-CH), 118.9 (d, J=22 Hz, 5-CH), 134.7 (d, J=8.5 Hz, 6-CH), 137.8 (d, J=10 Hz, 2-C), 153.9 (7-C), 160.9 (8-C), 161.8 (d, J=251 Hz, 4-CF); HRMS (ESI) calcd for $C_{10}H_{10}BrFN_3$ (M+H) 270.0042, found 270.0048 (δ+2.2 ppm). This triazole was also prepared in 62% yield from 1-(2-bromo-5-fluoro-phenyl)-hydrazine hydrochloride and 2,4,6-trimethyl-s-triazine by refluxing them in EtOH.

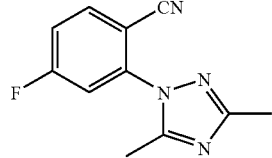

Intermediate 62

4-Fluoro-2-(5-methyl-1H-1,2,4-triazol-1-yl)benzonitrile. The title compound was prepared in 64% yield as a tan crystalline powder (HPLC: 1.31 min, AP 95% at 220 nm) from 1-(2-bromo-5-fluorophenyl)-3,5-dimethyl-1H-1,2,4-triazole and CuCN in DMF at 125-130° C. for 7 h by the method used for the preparation of 4-fluoro-2-pyrazol-1-yl-benzonitrile. An analytical sample was obtained by column purification ($SiO_2$, 20% EtOAc/$CH_2Cl_2$), followed by trituration with $Et_2O$. LC/MS m/z 217 (M+H). $^1$H NMR ($CDCl_3$, 500 MHz) δ ppm 2.45 (3H, s, 11-Me), 2.49 (3H, s, 10-Me), 7.25 (1H, dd, J=8.5, 2.5 Hz, 3-CH), 7.31 (1H, dt, J=8.5, 2.5 Hz, 5-CH), 7.87 (1H, dd, J=8.7, 5.6 Hz, 6-CH). $^{13}$C NMR (CDCl$_3$, 125.8 Hz) δ ppm 12.7 (10-Me), 13.8 (11-Me), 107.1 (d, J=3.8 Hz, 1-C), 114.8 (7-CN), 116.2, (d, J=25 Hz, 3-CH), 117.6 (d, J=22 Hz, 5-CH), 136.0 (d, J=10 Hz, 6-CH), 141.6 (d, J=10 Hz, 2-C), 153.9 (8-C), 161.0 (9-C), 165.0 (d, J=260 Hz, 4-CF). HRMS (ESI) calcd for C$_{11}$H$_{10}$FN$_4$ (M+H) 217.0889, found 271.0879 (δ-4.8 ppm). Anal. calcd for C$_{11}$H$_9$FN$_4$: C61.10, H4.19, N25.91; found C60.78, H3.93, N26.05.

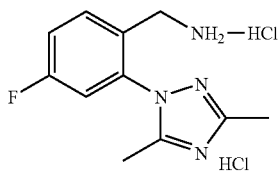

Intermediate 63

4-Fluoro-2-(5-methyl-1H-1,2,4-triazol-1-yl)benzylamine di-hydrochloride. The title compound was prepared in quantitative yield as a white powder (HPLC: 0.52 min, AP 84% at 220 nm) from 4-fluoro-2-(5-methyl-1H-1,2,4-triazol-1-yl)benzonitrile by the hydrogenation method used for the preparation of 4-fluoro-2-pyrazol-1-yl-benzylamine hydrochloride. An analytical sample was obtained by reverse phase C-18 column purification (2 mM HCl—H$_2$O) LC/MS m/z 221 (M+H). $^1$H NMR (CD$_3$OD, 500 MHz) δ ppm 2.67 (3H, s, 11-Me), 2.77 (3H, s, 10-Me), 4.16 (2H, s, 7-CH$_2$), 7.61 (1H, dt, J=8.5, 2.5 Hz, 5-CH), 7.67 (1H, dd, J=8.5, 2.4 Hz, 3-CH), 7.93 (1H, dd, J=8.8, 5.7 Hz, 6-CH). $^{13}$H NMR (CD$_3$OD, 125.8 MHz) δ ppm 10.5, 10.7 (10,11-Me), 38.2 (7-CH$_2$), 115.1, (d, J=26 Hz, 3-CH), 119.3 (d, J=21 Hz, 5-CH), 126.9 (d, J=3.8 Hz, 1-C), 134.5 (d, J=9.6 Hz, 6-CH), 135.3 (d, J=10.6 Hz, 2-C), 154.1, 154.4 (8,9-C), 163.1 (d, J=251 Hz, 4-CF). HRMS (ESI) calcd for C$_{11}$H$_{14}$FN$_4$ (M+H) 221.1202, found 221.1204 (6-0.7 ppm); UV (MeOH) λ max 232 nm (ε 8.74×10$^3$); Anal calcd for C$_{11}$H$_{13}$FN$_4$.2.2HCl.0.6H$_2$O: C42.47, H5.25, N18.01, C125.07, H$_2$O3.48; found: 42.95, H4.80, N18.41, C124.56, H$_2$O3.00 (KF).

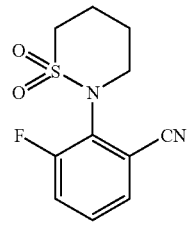

Intermediate 64

4-Fluoro-2-imidazol-1-yl-benzonitrile. To a solution of imidazole (4.45 g, 65.4 mmol) in tetrahydrofuran (30 mL) and dimethylformamide (10 mL) was added potassium carbonate (9.95 g, 72 mmol) and the mixture was stirred for 30 min at room temp. To this was added 2,4-difluorobenzonitrile (10.0 g, 72 mmol) and the mixture stirred at 90° C. for 3 h then at room temp for 2 days. The mixture was filtered and concentrated and the residue was purified by flash chromatography (SiO$_2$) eluting with 20% to 70% ethyl acetate/hexane to give the title compound as white needles (1.1 g, 9% yield). $^1$H-NMR (500 MHz, CDCl$_3$) δ ppm: 7.94 (1H, s), 7.84 (1H, dd, J=8.7, 5.6 Hz), 7.37 (1H, t, J=8.7, 5.6 Hz), 7.37 (1H, t, J=1.4 Hz), 7.29 (1H, t, J=1.1 Hz), 7.27-7.21 (2H, m). LCMS [M+H]$^+$ calcd for C$_{10}$H$_7$N$_3$F: 188.058; found: 188.12.

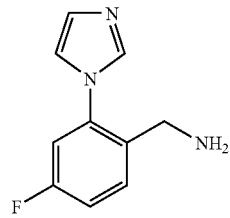

Intermediate 65

(4-Fluoro-2-(1H-imidazo-1-yl)phenyl)methanamine) hydrochloride. The title compound can be prepared from 4-fluoro-2-imidazol-1-yl-benzonitrile. Yellow solid, $^1$H-NMR (500 MHz, CD$_3$OD) δ ppm: 9.39 (1H, s), 7.98 (1H, d, J=1.5 Hz), 7.92-7.89 (2H, m), 7.63-7.59 (2H, m), 4.11 (2H, s). LCMS [M+H]$^+$ calcd for C$_{10}$H$_{11}$N$_3$F: 192.09; found: 192.15.

Intermediate 66

3-Fluoro-2-(1,1-dioxo-1λ6-[1,2]thiazinan-2-yl)benzonitrile. To a solution of 1,1-dioxo-1λ6-[1,2]thiazin-2-ane (1.90 g, 14.4 mmol) dissolved in tetrahydrofuran (8 mL) and dimethylformamide (2 mL) was added sodium hydride (0.36 g, 95%, 14.4 mmol) and the mixture stirred for 20 min. To this was added 2,3-difluorobenzonitrile (2.0 g, 14.4 mmol) and the mixture stirred at 90° C. for 2 h. The mixture was partitioned between ethyl acetate and water. The organic phase was washed with water and brine then concentrated. The solid residue was triturated with 1:1 ethyl acetate/hexane to give the title compound as a pale brown solid (0.47 g, 13% yield). $^1$H-NMR (500 MHz, CDCl$_3$) δ ppm: 7.47-7.45 (1H, m), 7.32-7.36 (2H, m), 4.08-4.02 (1H, m), 3.57 (1H, td, J=13.0, 3,7 Hz), 3.40-3.34 (1H, m), 3.32-3.27 (1H, m), 2.44-2.32 (2HF, m), 2.04-1.97 (2H, m), 1.90-1.84 (1H, m). LCMS [M+H]$^+$ calcd for C$_{11}$H$_{12}$N$_2$FO$_2$S: 255.28; found: 255.13.

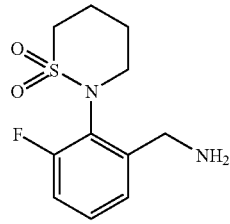

Intermediate 67

3-Fluoro-2-(1,1-dioxo-1λ6-[1,2]thiazinan-2-yl)benzylamine hydrochloride. The title compound can be prepared from 3-fluoro-2-(1,1-dioxo-1λ6-[1,2]thiazinan-2-yl)benzonitrile. White solid, $^1$H-NMR (500 MHz, CD$_3$OD) δ ppm: 7.56-7.52 (1H, m), 7.40-7.34 (1H, m), 4.31 (2H, s), 3.98-3.93 (1H, m), 3.68-3.64 (1H, m), 3.42-4.39 (2H, m), 2.42-2.37 (2H, m), 2.03-1.92 (2H, m). LCMS [M+H]$^+$ calcd for C$_{11}$H$_{16}$N$_2$O$_2$FS: 259.09; found: 259.18.

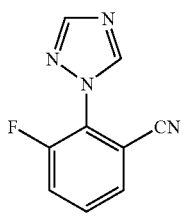

Intermediate 68

3-Fluoro-2-1,2,4-triazol-1-yl-benzonitrile. A mixture of 2,3-difluorobenzylnitrile (2.27 g, 16.3 mmol) and triazole sodium salt (1.33 g, 14.8 mmol) in tetrahydrofuran (5 mL) and dimethylformamide (10 mL) was stirred at 85° C. for 4 h. After concentration, the residue was purified by flash chromatography (SiO$_2$) eluting with 25%-50% ethyl acetate/hexane. The isolated product was recrystallized from hot ethyl acetate/hexane to give the title compound as white needles (1.51 g, 54% yield). $^1$H-NMR (500 MHz, CDCl$_3$) δ ppm: 8.50 (1H, d, J=2.4 Hz), 8.25 (1H, s), 7.69-7.67 (1H, m), 7.60-7.57 (2H, m). LCMS [M+H]$^+$ calcd for C$_9$H$_6$N$_4$F: 189.16; found: 189.14.

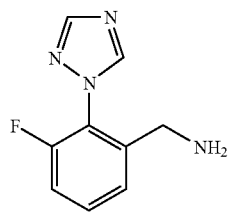

Intermediate 69

(3-Fluoro-2-(1H-1,2,4-triazol-1-yl)phenyl)methanamine. The title compound can be prepared from 3-fluoro-2-1,2,4-triazol-1-yl-benzonitrile. $^1$H-NMR (500 MHz, CD$_3$OD) δ ppm: 9.61 (1H, d, J=2.9 Hz), 8.79 (1H, s), 7.82-7.74 (1H, m), 7.67-7.57 (2H, m), 4.14-4.13 (2H, m). LCMS [M+H]$^+$ calcd for C$_9$H$_{10}$N$_4$F: 193.08; found: 193.16.

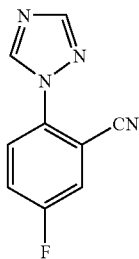

Intermediate 70

5-Fluoro-2-(1H-1,2,4-triazol-1-yl)benzonitrile. A suspension of 2,5-diflurobenzonitrile (4.5 g, 32.35 mmol) and 1,2,4-triazole sodium salt (3.6 g, 40 mmol) in dimethylformamide (40 mL) was heated at 80° C. for 15 h. The reaction mixture was then cooled, diluted with CH$_2$Cl$_2$ (200 mL), washed with water (3×30 mL) and brine (30 mL), then dried (Na$_2$SO$_4$), filtered and concentrated to give a white solid which was purified by flash column chromatography (SiO$_2$) using 1:1 to 3:1 ethyl acetate/Hexanes to afford the title compound (2.98 g, 49% yield) as a white powder. $^1$H NMR (500 MHz, CDCl$_3$) δ: 8.70 (1H, s), 8.18 (1H, s), 7.76 (1H, dd, J=9.0, 4.8 Hz), 7.55 (1H, dd, J=7.3, 2.8 Hz), 7.51-7.47 (1H, m). LCMS (M+H) calcd for C$_9$H$_6$FN$_4$: 189.17; found: 189.10.

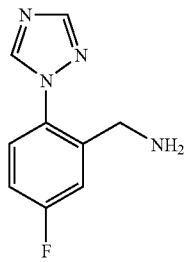

Intermediate 71

(5-Fluoro-2-(1H-1,2,4-triazol-1-yl)phenyl)methanamine hydrochloride. A solution of 5-fluoro-2-(1H-1,2,4-triazol-1-yl)benzonitrile (2.94 g, 15.59 mmol) in ethanol (100 mL) and 1N HCl (50 mL) was degassed by bubbling N$_2$. Then, 10% Pd/C was added, the flask evacuated and vented to H$_2$ three times and left on a Parr shaker under a H$_2$ atmosphere (40 psi). After 6 h, the reaction mixture was filtered, concentrated and the aqueous solution lyophilized to afford the title compound (4.07 g, 98%) as a white powder. LCMS (M+H) calcd for C$_9$H$_{10}$FN$_4$: 193.09; found: 193.15.

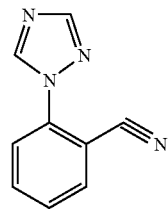

Intermediate 72

2-(1H-1,2,4-Triazol-1-yl)benzonitrile. A suspension of 2-fluorobenzylnitrile (3.0 g, 25 mmol) and 1,2,4-triazole sodium salt (2.4 g, 27 mmol) were stirred in tetrahydrofuran (7 mL) and dimethylformamide (14 mL) at 95° C. for 18 h. After cooling and concentrating, the product was crystallized from hot CH$_2$Cl$_2$/hexane (1:1) to give the title compound as a white solid (4.25 g, 100% yield). $^1$H-NMR (300 MHz, CDCl$_3$) δ ppm: 8.74 (1H, s), 8.16 (1H, s), 7.82 (1H, dd, J=4.9, 1.3 Hz), 7.77-7.25 (2H, m), 7.57-7.51 (1H, m). LCMS [M+H]$^+$ calcd for C$_9$H$_7$N$_4$: 171.06; found: 171.12.

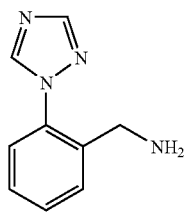

Intermediate 73

(2-(1H-1,2,4-Triazol-1-yl)phenyl)methanamine hydrochloride. 2-(1H-1,2,4-Triazol-1-yl)benzonitrile (4.25 g, 25 mmol) was dissolved in ethanol (50 mL) and 1N HCl (25 mL). 10% Pd—C (1 g) was added and the mixture shaken under H$_2$ for 2 h at 50 psi. After filtration through Celite® and concentration, the residue was triturated with diethyl ether Intermediate 74

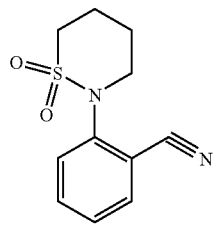

2-(1,1-Dioxo-1λ⁶-[1,2]thiazinan-2-yl)benzonitrile.
Sodium hydride (0.675 g, 25 mmol, 95%) was added to a solution of 1,1-dioxo[1,2]thiazinane (3.37 g, 25 mmol) in dimethylformamide (35 mL) and the mixture stirred at room temperature for 15 min. 2-Fluorobenzonitrile (3.37 mL, 31.3 mmol) was added and the mixture stirred at 80° C. for 18 h. The mixture was cooled, diluted with water and extracted with ethyl acetate. The organic phase was washed with water and brine, then dried (Na$_2$SO$_4$) and concentrated. The residue was purified by flash chromatography (SiO$_2$) eluting with 10%-100% ethyl acetate/hexane. The isolated solid was recrystallized from hot ethyl acetate/hexane (2:1) to give the title compound as white crystals (4.15 g, 70% yield). $^1$H-NMR (300 MHz, CDCl$_3$) δ ppm: 7.70 (1H, dd, J=7.7, 1.1 Hz), 7.64-7.53 (2H, m), 7.41 (1H, td, J=7.3, 1.6 Hz), 3.72 (2H, t, J=5.5 Hz), 3.32 (2H, t, J=6.0 Hz), 2.40-2.32 (2H, m), 2.05-1.97 (2H, m). LCMS [M+H]$^+$ calcd for C$_{11}$H$_{12}$N$_2$O$_2$S: 237.06; found: 237.10.

Intermediate 75

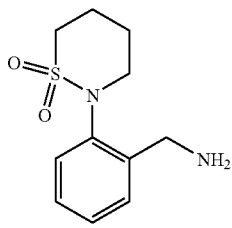

2-(1,1-Dioxo-1λ⁶-[1,2]thiazinan-2-yl)benzylamine hydrochloride. 2-(1,1-Dioxo-1λ⁶-[1,2]thiazinan-2-yl)benzonitrile, (2.63 g, 11.14 mmol) was dissolved in ethanol (150 mL) and 1N HCl (13 mL). 10% Pd—C (0.5 g) was added and the mixture shaken under H$_2$ at 55 psi for 24 h. Filtration through Celite® followed by concentration gave the title compound as a white solid (2.93 g, 95% yield). $^1$H-NMR (300 MHz, CD$_3$OD) δ ppm: 7.61-7.47 (4H, m), 4.30 (2H, q, J=13.7 Hz), 3.96-3.87 (1H, m), 3.49-3.36 (3H, m), 2.40-2.31 (2H, m), 2.05-1.96 (2H, m). LCMS [M+H]$^+$ calcd for C$_{11}$H$_{17}$N$_2$SO$_2$: 241.10; found: 241.10.

Intermediate 76

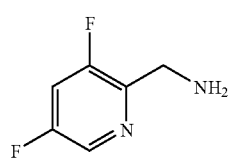

(3,5-Difluoropyridin-2-yl)methanamine hydrochloride. A mixture of 3,5-difluoropicolinonitrile (1.4 g, 10 mmol), conc. HCl (12 ml) and 10% Pd—C (200 mg) in 1:1 ethanol/tetrahydrofuran was shaken under a hydrogen atmosphere (50 psi) for 5 h. The reaction mixture was filtered and the ethanol removed in vacuo. The remaining solution was lyophilized to afford an off-white solid (2.16 g, 100% yield). LCMS (M+H) calcd for C$_6$H$_7$F$_2$N$_2$: 145.06; found: 145.12.

Intermediate 77

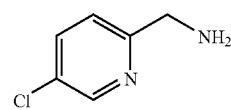

(5-Chloropyridin-2-yl)methanamine. A solution of 5-chloropicolinonitrile (3.8 g, 27.43 mmol), conc. HCl (3 mL) and 10% Pd—C (1.0 g) in ethanol (100 mL) was shaken under a hydrogen atmosphere (40 psi) for 2 h. The reaction mixture was filtered, concentrated and the resulting residue taken up in satd NaHCO$_3$ (50 mL) and extracted with CH$_2$Cl$_2$ (4×25 mL). The combined CH$_2$Cl$_2$ layers were dried (Na$_2$SO$_4$), filtered and concentrated to give the title compound as a yellow oil (2.0 g, 51% yield). LCMS (M+H) calcd for C$_6$H$_8$ClN$_2$: 143.04; found: 143.07. $^1$HNMR (500 MHz, CDCl$_3$) δ ppm: 8.56-8.51 (1H, br d), 7.66-7.60 (1H, m), 7.28-7.14 (1H, m), 3.97 (2H, s), 1.72 (2H, s).

Intermediate 78

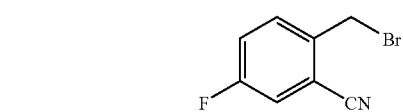

2-(Bromomethyl)-5-fluorobenzonitrile. N$_2$ was passed through a mixture of 5-fluoro-2-methylbenzonitrile (28.51 g, 211 mmol), NBS (41.31 g, 232 mmol) and AIBN (2.5 g, 15 mmol) in CCl$_4$ (845 mL) for 10 min after which the reaction was heated at reflux for 8 h. After standing at room temperature overnight, the reaction mixture was filtered and the filter cake washed with CCl$_4$ (500 mL). The combined filtrate was evaporated to give a yellow oil. Flash chromatography (SiO$_2$) using 5-25% ethyl acetate/Hexanes as eluent afforded the title compound (29.74 g, 66% yield) as a pale yellow oil. $^1$H NMR (500 MHz, CDCl$_3$) δ: 7.55 (1H, dd, J=8.6, 5.2 Hz), 7.37 (1H, dd, J=7.9, 2.8 Hz), 7.32-7.28 (1H, m), 4.61 (2H, s).

Intermediate 79

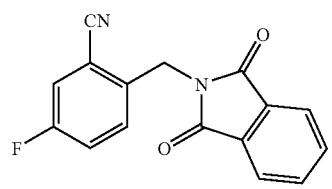

2-((1,3-Dioxoisoindolin-2-yl)methyl)-5-fluorobenzonitrile. To a stirred solution of intermediate 104, 2-(bromomethyl)-5-fluorobenzonitrile (29.72 g, 139 mmol) and phthalimide (32.69 g, 222 mmol) in dimethylformamide (300 mL) was added Cs$_2$CO$_3$ (67.87 g, 208 mmol). After stirring vigorously for 1 h, the reaction mixture was poured into water (1.2 L). The precipitated product was filtered, washed with water (600 mL) and methanol (150 mL) to give a white solid. The solid was taken up into 1 L of water/methanol (2:1) to which was added K$_2$CO$_3$ (12 g) and the mixture stirred at 40° C. After 30 min., the mixture was cooled and filtered. The filter cake was washed with water (500 mL), and dried under vacuum to afford the title compound (38.91 g, 94% yield) as a white powder. $^1$H NMR (500 MHz, CDCl$_3$) δ: 7.89 (2H, dd, J=5.5, 3.1 HZ), 7.76 (5.5, 3.1 Hz), 7.41 (1H, dd, J=8.6, 5.2 Hz), 7.38 (1H, dd, J=7.9, 2.8 Hz), 7.24 (1H, td, J=8.2, 2.8 Hz), 5.06 (2H, s). LCMS (M+H) calcd for C$_{16}$H$_{10}$FN$_2$O$_2$: 281.07; found: 281.15.

Intermediate 80

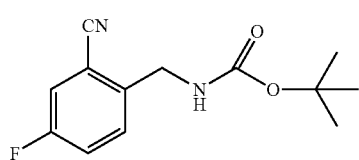

tert-Butyl 2-cyano-4-fluorobenzylcarbamate. A suspension of 2-((1,3-dioxoisoindolin-2-yl)methyl)-5-fluorobenzonitrile, (5.6 g, 20 mmol) in dimethylformamide (20 mL) was warmed until it was dissolved. To this was added tetrahydrofuran (100 mL) and the mixture placed in a pre-heated (70° C.) oil bath. Hydrazine monohydrate was added to this and the reaction stirred for 8 h. The resulting white slurry was left at ambient temperature overnight. To this slurry was added di-tert-butyldicarbonate (6.55 g, 30 mmol) and the mixture stirred for 6 h at room temperature. The reaction mixture was diluted with ether (100 mL), filtered and the filtrate treated with activated carbon at 40° C. After filtration and concentration the crude product was purified by flash chromatography, using 20-30% ethyl acetate/Hexanes as eluent, to provide the title compound (2.88 g, 58% yield) as a light yellow powder. $^1$H NMR (500 MHz, CDCl$_3$) δ: 9.46 (1H, br s), 7.61 (1H, dd, J=7.9, 2.1 Hz), 7.34 (1H, dd, J=8.2, 4.6 Hz), 7.22 (1H, td, J=8.6, 2.4 Hz), 4.71 (2H, s), 1.59 (9H, s). LCMS (M+H) calcd for C$_{13}$H$_{16}$FN$_2$O$_2$: 251.12; found: 251.22.

Intermediate 81

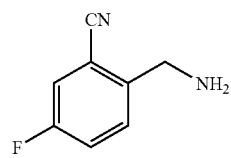

2-(Aminomethyl)-5-fluorobenzonitrile trifluoroacetic acid salt. A round-bottom flask was charged with tert-butyl 2-cyano-4-fluorobenzylcarbamate, (1.9 g, 7.591 mmol) then treated with trifluoroacetic acid (20 ml) at room temperature. After 1 h, the reaction mixture was concentrated to give a yellow oil which was dissolved in CHCl$_3$ and re-concentrated to afford the title compound (2.01 g, 100% yield) as a pale yellow solid. LCMS (M+H) calcd for C$_8$H$_8$FN$_2$: 151.07; found: 151.08.

Intermediate 82

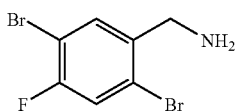

(2,5-Dibromo-4-fluorophenyl)methanamine. A solution of 2,5-dibromo-4-fluorobenzyl bromide (0.350 g, 1 mmol) in 7M NH$_3$/MeOH was heated in a sealed tube at 100° C. for 2 h. The reaction mixture was cooled and concentrated to give a white solid which was dissolved in CH$_2$Cl$_2$ and treated with Et$_3$N (1 mL) then concentrated. The resulting residue was triturated with ethyl acetate (25 mL), filtered and concentrated to give the title compound (0.291 g) as a pale yellow oil. HRMS (M+H) calcd for C$_7$H$_7$Br$_2$FN: 283.94; found: 283.93.

Intermediate 83

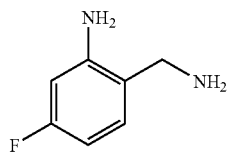

2-(Aminomethyl)-5-fluorobenzenamine hydrochloride. 2-Amino-4-fluorobenzonitrile (Fritz Hunziker et al. Eur. J. Med. Chem. 1981, 16, 391) (0.300 g, 1.68 mmol), was dissolved in acetic anhydride (5 mL) and the solution was stirred at 23° C. for 18 h. An additional portion of acetic anhydride (3 mL) was added to dissolve the N-(2-cyano-5-fluorophenyl) acetamide. Then palladium (10% on charcoal) (25 mg) was added and the mixture was agitated under H$_2$ (34 psi) for 72 h. The Pd—C was removed by filtration on Celite® and the filtrate concentrated in vacuo to afford a bis-acetamide: LCMS (M+H)+m/z 225. This was heated at reflux with HCl (6N, 10 mL) for 30 min. The acid was removed under reduced pressure to give a solid which was crystallized from MeOH-ether to afford the title compound (0.120 g, 51% yield). $^1$H NMR (400 MHz, MeOD) δ ppm: 7.51 (1H, m), 6.96 (2H, m), 4.20 (2H, s).

Intermediate 84

4-Fluoro-2-(2-oxopyrrolidin-1-yl)benzonitrile. A 48 mL pressure vessel containing 2-bromo-4-fluorobenzonitrile (1.00 g, 5.00 mmol), 2-pyrrolidinone (0.46 mL, 6.00 mmol), Cs$_2$CO$_3$ (2.28 g, 7.0 mmol) and 9,9-dimethyl-4,5-bis(diphenylphosphino)xanthene (xantphos) (0.231 g, 0.40 mmol) in dioxane (6 mL) was degassed with argon for 15 min. Pd$_2$dba$_3$ was introduced and the reaction mixture heated at 105° C. for 48 h. The mixture was cooled, diluted with ethyl acetate or dioxane, and then filtered through Celite®. The resulting mixture was concentrated in vacuo and subjected to column chromatography on silica gel with hexanes:ethyl acetate (3:7) gradient as the eluent to afford the title compound as a white solid (0.887 g, 87% yield): $^1$H NMR (400 MHz, CDCl$_3$) δ ppm: 7.69 (1H, dd, J=5.8, 8.6 Hz), 7.22 (1H, dd, J=2.5, 9.6 Hz), 7.07 (1H, ddd, J=2.5, 7.6, 8.6 Hz), 3.96 (2H, t, J=7.0 Hz), 2.62 (2H, t, J=8.1 Hz), 2.30-2.22 (2H, m); LCMS ($^+$ESI, M+H$^+$) m/z 205.

Intermediate 85

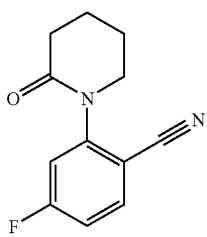

4-Fluoro-2-(2-oxopiperidin-1-yl)benzonitrile. $^1$H NMR (400 MHz, CDCl$_3$) δ ppm: 7.71 (1H, dd, J=5.7, 8.7 Hz), 7.14-7.06 (1H, m), 7.08 (1H, dd, J=2.4, 9.0 Hz), 3.65 (2H, t, J=5.7 Hz), 2.60 (2H, t, J=6.3 Hz), 2.05-1.95 (4H, m); LCMS ($^+$ESI, M+H$^+$) ml/z 219.

Intermediate 86

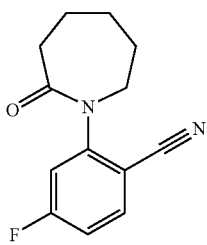

4-Fluoro-2-(2-oxoazepan-1-yl)benzonitrile. $^1$H NMR (400 MHz, CDCl$_3$) δ ppm: 7.68 (1H, dd, J=5.8, 8.6 Hz), 7.08 (1H, ddd, J=2.5, 7.6, 8.6 Hz), 7.01 (1H, dd, J=2.5, 9.0 Hz), 3.77-3.76 (2H, m), 2.75-2.72 (2H, m), 1.91-1.86 (6H, m); LCMS ($^+$ESI, M+H$^+$) m/z 233.

Intermediate 87

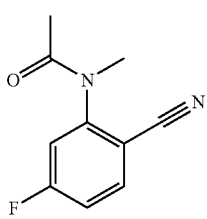

N-(2-Cyano-5-fluorophenyl)-N-methylacetamide. $^1$H NMR (400 MHz, CDCl$_3$) δ ppm: 7.79-7.75 (1H, m), 7.32-7.19 (1H, m), 7.10-7.07 (1H, m), 3.42 (0.6H, brs), 3.30 (2.4H, s), 2.32 (0.6H, brs), 1.91 (2.4H, s); LCMS ($^+$ESI, M+H$^+$) m/z 193; HPLC: 94% (220 nm).

Intermediate 88

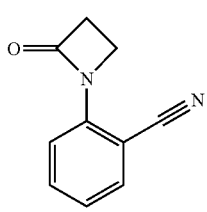

2-(2-Oxoazetidin-1-yl)benzonitrile. $^1$H NMR (400 MHz, DMSO-d6) δ ppm: 8.02 (1H, d, J=8.4 Hz), 7.76 (1H, dd, J=1.5, 7.8 Hz), 7.69-7.65 (1H, m), 7.23 (1H, s), 4.04 (2H, t, J=4.8 Hz), 3.16 (2H, t, J=4.8 Hz). LCMS ($^+$ESI, M+H$^+$) m/z 173.

Intermediate 89

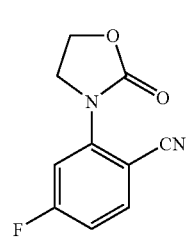

2-(2-Oxooxazolidin-3-yl)benzonitrile. $^1$H NMR (400 MHz, CDCl$_3$) δ ppm: 7.71 (1H, dd, J=1.5, 7.6 Hz), 7.68-7.63 (1H, m), 7.58 (1H, d, J=7.6 Hz), 7.38 (1H, dt, J=1.3, 7.6 Hz), 4.57 (2H, t, J=7.8 Hz), 4.21 (2H, t, J=7.8 Hz); LCMS ($^+$ESI, M+H$^+$) m/z 189.

Intermediate 90

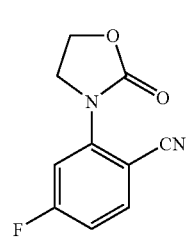

4-Fluoro-2-(2-oxooxazolidin-3-yl)benzonitrile. A 48 mL pressure vessel containing 2-bromo-4-fluorobenzonitrile (1.00 g, 5.00 mmol), 2-oxazolidone (0.390 g, 4.50 mmol), K$_2$CO$_3$ (0.970 g, 7.0 mmol) and xantphos (0.231 g, 0.40 mmol) in dioxane (10 mL) was degassed with argon for 15 min. Pd$_2$dba$_3$ (0.140 g, 0.15 mmol) was introduced and then the reaction mixture was heated at 70° C. for 18 h. The mixture was cooled, diluted with dioxane, and then filtered through Celite®. The resulting mixture was concentrated in vacuo and subjected to column chromatography on silica gel with hexanes:ethyl acetate (1:1) to (3:7) gradient as the eluent to afford the title compound as a white solid (0.460 g, 50% yield): $^1$H NMR (400 MHz, CDCl$_3$) δ ppm: 7.73 (1H, dd, J=5.8, 8.6 Hz), 7.43 (1H, dd, J=2.5, 9.6 Hz), 7.11 (1H, ddd, J=2.5, 7.5, 8.7 Hz), 4.60 (2H, t, J=7.1 Hz), 4.29 (2H, t, J=7.1 HJz); LCMS ($^+$ESI, M+H$^+$) m/z 207.

Intermediate 91

3-(2-(Aminomethyl)-5-fluorophenyl)oxazolidin-2-one hydrochloride. $^1$H NMR (400 MHz, MeOD) δ ppm: 7.73 (1H, dd, J=6.0, 8.6 Hz), 7.43 (1H, dd, J=2.5, 9.5 Hz), 7.11 (1H, ddd, J=2.5, 7.5, 8.6 Hz), 4.64 (2H, t, J=7.7 Hz), 4.17 (2H, t, J=7.7 Hz), 4.14 (2H, s); LCMS ($^+$ESI, M+H$^+$) m/z 211.

Intermediate 92

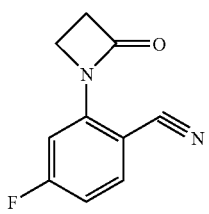

4-Fluoro-2-(2-oxoazetidin-1-yl)benzonitrile. $^1$H NMR (400 MHz, CDCl$_3$) δ ppm: 8.06 (1H, dd, J=10.7, 2.6 Hz), 7.58 (1H, dd, J=8.6, 6.3 Hz), 7.87 (1H, td, J=8.6, 2.5 Hz), 4.25 (2H, t, J=5.0 Hz), 3.26 (2H, t, J=5.0 Hz); LCMS ($^+$ESI, M+H$^+$) m/z 191.

Intermediate 93

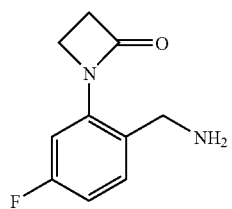

1-(2-(Aminomethyl)-5-fluorophenyl)azetidin-2-one hydrochloride. $^1$H NMR (400 MHz, DMSO/D$_2$O) δ ppm: 7.54 (1H, dd, (t), J=8.6 Hz), 7.25 (1H, dd, J=10.8, 2.5 Hz), 7.17 (1H, td, J=8.6, 2.5 Hz), 4.12 (2H, s), 3.79 (2H, t, J=4.6 Hz), 3.09 (2H, t, J=4.6 Hz); LCMS ($^+$ESI, M+H$^+$) m/z 195.

Intermediate 94

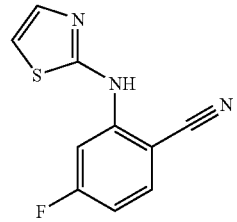

(R)-2-(2-((tert-Butyldimethylsilyloxy)methyl)-5-oxopyrrolidin-1-yl)-4-fluorobenzonitrile. $^1$H NMR (400 MHz, CDCl$_3$) δ ppm: 7.68 (1H, dd, J=5.8, 8.8 Hz), 7.19 (1H, dd, J=2.5, 9.1 Hz), 7.11-7.07 (1H, m), 4.46-4.42 (1H, m), 3.55 (2H, d, J=3.3 Hz), 2.72-2.52 (2H, m), 2.43-2.33 (1H, m), 2.09-2.01 (1H, m), 0.81 (9H, s), −0.04 (3H, s), −0.07 (3H, s); LCMS ($^+$ESI, M+H$^+$) m/z 349.

Intermediate 95

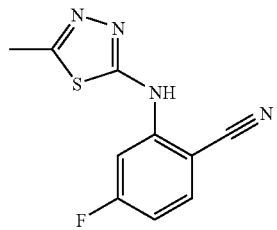

(S)-2-(2-((tert-Butyldimethylsilyloxy)methyl)-5-oxopyrrolidin-1-yl)-4-fluorobenzonitrile. $^1$H NMR (400 MHz, CDCl$_3$) δ ppm: 7.68 (1H, dd, J=5.8, 8.6 Hz), 7.19 (1H, dd, J=2.5, 9.4 Hz), 7.11-7.07 (1H, m), 4.46-4.43 (1H, m), 3.55 (2H, d, J=3.3 Hz), 2.72-2.52 (2H, m), 2.43-2.33 (1H, m), 2.09-2.01 (1H, m), 0.81 (9H, s), −0.04 (3H, s), −0.07 (3H, s); LCMS ($^+$ESI, M+H$^+$) m/z 349.

Intermediate 96

4-Fluoro-2-(thiazol-2-ylamino)benzonitrile. $^1$H NMR (400 MHz, DMSO-d$_6$) δ ppm: 9.21 (1H, s), 8.39-8.35 (1H, m), 7.97 (1H, d, J=5.0 Hz), 7.23-7.13 (3H, m); LCMS ($^+$ESI, M+H$^+$) m/z 220.

Intermediate 97

4-Fluoro-2-(5-methyl-1,3,4-thiadiazol-2-ylamino)benzonitrile. $^1$H NMR (400 MHz, DMSO-d$_6$) δ ppm: 8.30 (1H, dd, J=6.5, 8.8 Hz), 7.96 (1H, s), 7.26-7.19 (2H, m), 2.64 (3H, s); LCMS ($^+$ESI, M+H$^+$) m/z 235.

Intermediate 98

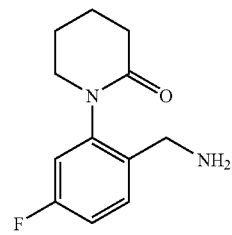

1-(2-(Aminomethyl)-5-fluorophenyl)piperidin-2-one hydrochloride salt. To a stirred solution of 4-fluoro-2-(2-oxopiperidin-1-yl)benzonitrile (150 mg, 0.69 mmol) in H$_2$O (10 mL) was added ethanol (10 mL) 10% palladium on charcoal (50 mg) and 1N HCl (2.1 mL, 20.6 mmol). The reaction was shaken in a Parr system under H$_2$ (40 psi) for 1 h. Then the Pd/C catalyst was removed by filtration on Celite® and the filtrate was concentrated in vacuo to yield a solid. Toluene (2×50 mL) was added to the solid and the solution was evaporated in vacuo. LCMS (M+H)$^+$ m/z 170.

Intermediate 99

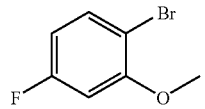

1-Bromo-4-fluoro-2-methoxybenzene. To a mixture of 2-bromo-5-fluorophenol (10 g, 50.8 mmol) and iodomethane (11.2 g, 78.7 mmol) in dimethylformamide (100 mL) was added potassium carbonate (10.9 g, 79 mmol) and the mixture stirred at room temperature for 3 hrs. The mixture was diluted with water (100 mL) and extracted with ether (50 mL×3). The combined extracts were washed with brine, dried over anhydrous magnesium sulfate, and concentrated in vacuo to obtain 11.3 g of 1-bromo-4-fluoro-2-methoxybenzene as an amber colored oil.

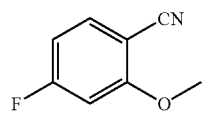

Intermediate 100

4-Fluoro-2-methoxybenzonitrile. To a solution of 1-bromo-4-fluoro-2-methoxybenzene (9.0 g) in N-methylpyrrolidone (100 mL, Sure Seal; Aldrich) was added CuCN (6.6 g, 73.7 mmol, 1.8 eq.; Aldrich), and the mixture stirred at 180° C. under anhydrous nitrogen for 5.5 hrs. After cooling, 14% aqueous NH$_4$OH (330 mL) was added and stirring continued for 45 min at room temperature. The mixture was extracted with ether (100 mL×3), and the combined extracts washed sequentially with dilute aqueous NH$_4$OH, dilute HCl and brine, then dried (MgSO$_4$), and concentrated to provide the title compound (5.2 g, Yield 85% in 2 steps) as a white solid: $^1$H NMR (CDCl$_3$, 500 MHz) δ ppm: 3.91 (3H, s, OMe), 6.69 (1H, dd, J=2.3 Hz, J=10.5 Hz, Ar—H), 6.72 (1H, dt, J=2.5 Hz, J=J=8.0 Hz, Ar—H), 7.55 (1H, dd, J=6.5 Hz, J=8.5 Hz, Ar—H); $^{13}$C NMR (CDCl$_3$, 125.8 Hz) δ ppm: 56.49, 98.16, 100.06, 100.27, 108.31, 108.50, 115.83 135.37, 135.46, 163.25, 163.34 165.47, 167.50. An analytical sample was obtained by trituration with ether: Anal. calcd for C$_8$H$_6$FNO: C 63.57, H 4.00, N 9.26; found: C 63.36, H 3.91, N 9.16.

Intermediate 101

4-Fluoro-2-methoxybenzylamine hydrochloride. To a mixture of 4-fluoro-2-methoxybenzonitrile, (800 mg, 5.3 mmol) and conc.HCl (0.53 mL, 6.36 mmol, 1.2 eq.) in ethanol (20 mL) was added 10% Pd—C (100 mg; Aldrich), and the mixture hydrogenated at 1 atm hydrogen for 15 hrs at room temperature. To this mixture was added an additional amount of conc.HCl (1 mL) and 10% Pd—C (200 mg) and the reaction allowed to continue for another 40 hrs. The mixture was filtered through Celite® and the filtrate concentrated in vacuo to dryness. The residue was triturated with ether to provide the title compound (895 mg, Yield 88%) as a white powder: $^1$H NMR (CDCl$_3$, 500 MHz) δ ppm: 3.84 (3H, s, OMe), 3.91 (2H, d, J=5.5 Hz, N—CH$_2$), 6.81 (1H, dt, J=2.5 Hz, J=J=8.5 Hz, Ar—H), 6.99 (1H, dd, J=2.5 Hz, J=11.3 Hz, Ar—H), 7.47 (1H, dd, J=7 Hz, J=8.5 Hz, Ar—H); $^{13}$C NMR (CDCl$_3$, 125.8 Hz) δ ppm: 36.76, 56.03, 99.30, 99.51 106.28, 106.45, 117.93, 117.95, 131.60, 131.69, 158.56, 158.64, 162.28, 164.22. HRMS (ESI) calcd for C$_8$H$_{11}$FNO (M+H) 156.0825, found 156.0830.

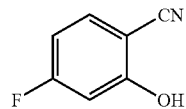

Intermediate 102

4-Fluoro-2-hydroxybenzonitrile. A mixture of 4-fluoro-2-methoxybenzonitrile, (4.53 g, 30 mmol;) and AlCl$_3$ (5.0 g, 37.6 mmol; Aldrich) in anhydrous toluene (30 mL) was stirred at approximately 130° C. for 18 hrs. After cooling, ice water (~50 mL) was added and the resulting mixture extracted with ether (20 mL×2). The combined extracts were washed sequentially with water and brine, then dried (MgSO$_4$), and concentrated in vacuo to provide the title compound (3.90 g, 28.5 mmol, Yield 95%) as a white solid: $^1$H NMR (DMSO-d6, 300 MHz) δ ppm: 6.74-6.84 (2H, m, Ar—Hs), 7.71 (1H, dd, J=7 Hz, J=8.5 Hz, Ar—H), 11.64 (1H, s, OH); $^{13}$C NMR (DMSO-d6, 75.5 Hz) δ ppm: 95.13 102.45, 102.78, 106.53, 106.83 115.53, 134.68, 134.84, 161.41, 161.58, 163.00, 166.35. HRMS (ESI-) calcd for C$_7$H$_3$NOF (M−H) 136.0199, found 136.0199.

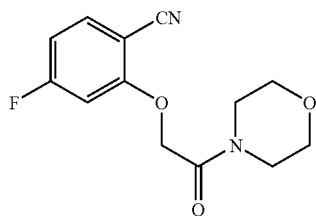

Intermediate 103

4-Fluoro-2-(2-morpholino-2-oxoethoxy)benzonitrile. To a solution of 4-fluoro-2-hydroxybenzonitrile, (685 mg, 5 mmol) in dimethylformamide (8 mL, Sure Seal; Aldrich) was added NaH (200 mg, 5 mmol; 60% oil dispersion; Aldrich), and the mixture stirred for 5 min under an anhydrous nitrogen atmosphere. To this was added 4-(2-chloroacetyl)morpholine (900 mg, 5.5 mmol, 1.1 eq.; Avocado Organics), and stirring continued at room temperature for 21 hrs. The reaction was quenched by careful addition of water (30 mL). The resulting mixture was extracted with CH$_2$Cl$_2$ (25 mL×2). The combined extracts were washed with brine, dried (MgSO$_4$) and concentrated. The residue was triturated to obtain 1.10 g (4.17 mmol, Yield 83%) of the title compound as a white solid: $^1$H NMR (CDCl$_3$, 500 MHz) δ ppm: 3.63 (2H, t, J=4 Hz, NCH$_2$), 3.67 (1H, m, OCH), 3.72 (1H, m, OCH), 4.86 (2H, s, OCH$_2$), 6.80-6.86 (2H, m, Ar—Hs), 7.61 (1H, dd, J=8.5 Hz, 6.1 Hz, Ar—H); $^{13}$C NMR (CDCl$_3$, 125.77 Hz) δppm: 42.63, 46.04, 66.80, 68.33, 98.45, 98.47, 101.57, 101.79, 109.56, 109.74, 115.42, 135.48, 135.57, 161.26, 161.35, 114.79, 165.23, 167.28. HRMS calcd for C$_{13}$H$_{14}$N$_2$O$_3$F (M+H) 265.0988, found 265.0998.

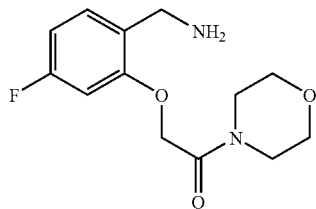

Intermediate 104

2-(2-(Aminomethyl)-5-fluorophenoxy)-1-morpholinoethanone hydrochloride. A solution of 4-fluoro-2-(2-morpholino-2-oxoethoxy)benzonitrile, (500 mg, 1.89 mmol) in warm ethanol (30 mL) and ethyl acetate (30 mL) was mixed with conc.HCl (0.32 mL, 3.78 mmol, 2 eq.). To this was added 10% Pd—C (100 mg; Aldrich), and the mixture was hydrogenated at 1 atm of hydrogen for 20 hrs at room temperature. To this mixture was added an additional amount of 10% Pd—C (50 mg) and stirring continued for another 7 hrs. The mixture was filtered through Celite® and the filtrate concentrated in vacuo to dryness. The residue was triturated with ethyl acetate, then with ethanol to obtain the title compound (168 mg, Yield 29%) as an off-white powder: $^1$H NMR (CD$_3$OD, 500 MHz) δ ppm: 3.55 (2H, t, J=5 Hz, NCH$_2$), 3.62 (2H, t, J=5 Hz, NCH$_2$), 3.70 (2H, t, J=5 Hz, OCH$_2$), 3.75 (2H, t, J=5 Hz, OCH$_2$), 4.17 (2H, s, NCH$_2$), 5.17 (2H, s, OCH$_2$), 6.82 (1H, dt, J=2.5, 8.5 Hz, Ar—H), 7.05 (1H, dd, J=2.5, 10.5 Hz, Ar—H), 7.43 (1H, dd, J=6.5, 8.5 Hz, Ar—H); $^{13}$C NMR (CD$_3$OD, 125.77 Hz) δ ppm: 39.40, 42.49, 44.97, 66.11, 66.46, 66.59, 101.38, 101.59, 108.40, 108.57, 118.40, 132.53, 132.62, 158.43, 158.52, 63.87, 165.83, 168.27. HRMS (ESI) calcd for C$_{13}$H$_{18}$N$_2$O$_3$F (M+H) 269.1301, found 269.1301.

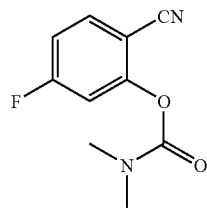

Intermediate 105

Dimethyl-carbamic acid 2-cyano-5-fluoro-phenyl ester. Under N$_2$, a stirred solution of 4-fluoro-2-hydroxybenzonitrile (685 mg, 5.00 mmol), dimethylcarbamoyl chloride, and triethylamine (606 mg, 6 mmol) in dichloromethane (10 mL) was heated at reflux for 20 hrs. The cooled mixture was diluted with dichloromethane (10 mL) washed with water, and brine. The organic layer was separated, dried (Na$_2$SO$_4$), concentrated, and the residue purified by column chromatography (SiO$_2$, 5% ethyl acetate-CH$_2$Cl$_2$) to provide 700 mg (Yield 67%) of the title compound as a white crystalline solid: $^1$H NMR (CDCl$_3$, 500 MHz) δ ppm: 3.03 (3H, s, NMe), 3.15 (3H, s, NMe), 6.99 (1H, dt, J=2.5 Hz, 8.5 Hz, Ar—H), 7.23 (1H, dd, J=2.5 Hz, 9.5 Hz, Ar—H), 7.61 (1H, dd, J=9 Hz, 6 Hz, Ar—H); $^{13}$C NMR (CDCl$_3$, 125.77 Hz) δ ppm: 36.76, 37.06, 102.84, 102.86, 111.59, 111.79, 113.24, 113.42, 114.99, 134.36, 134.45, 152.54, 155.06, 155.16, 164.26, 166.31. HRMS (ESI) calcd for C$_{10}$H$_{10}$N$_2$O$_2$F (M+H) 209.0726, found 209.0722.

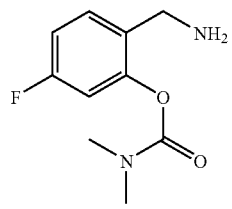

Intermediate 106

Dimethyl-carbamic acid 2-aminomethyl-5-fluoro-phenyl ester hydrochloride. To a solution of dimethyl-carbamic acid 2-cyano-5-fluoro-phenyl ester, (340 mg, 1.63 mmol) in ethyl acetate (20 mL) and ethanol (20 mL), was added conc.HCl (0.4 mL) and 10% Pd—C (100 mg) and the mixture hydrogenated in a Parr Shaker at 55 psi of hydrogen for 20 hrs. The reaction mixture was filtered through Celite®, and the filtrate concentrated in vacuo to give an oil which was partitioned between ethyl acetate (10 mL) and water (10 mL). After separation, the aqueous phase was washed with additional ethyl acetate (5 mL). The combined extracts were concentrated in vacuo to dryness. The residual oil was triturated with ether to provide 145 mg (Yield 38%) of the title compound, as a tan powder: $^1$H NMR (CD$_3$OD, 500 MHz) δ ppm: 3.06 (3H, s, NMe), 3.21 (3H, s, NMe), 4.11 (2H, s, NCH$_2$), 7.13 (2H, m, Ar—Hs), 7.60 (1H, m, Ar—H); $^{13}$C NMR (CD3OD, 125.77 Hz) δ ppm: 36.03, 36.25 37.58, 110.79, 110.99, 113.26, 113.43, 122.32, 132.18, 132.25, 151.55, 154.72, 162.69, 164.67. HRMS (ESI) calcd for C$_{10}$H$_{13}$N$_2$O$_2$F (M+H) 213.1039, found 213.1039.

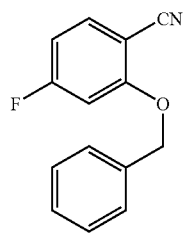

Intermediate 107

2-(Benzyloxy)-4-fluorobenzonitrile. Benzyl alcohol (13 mL, 125 mmol) was slowly added to a stirred suspension of NaH (95%, 2.86 g, 113 mmol) in toluene (200 mL) at room temperature. After 30 min, 2,4-difluorobenzonitrile (15.3 g, 110 mmol; Aldrich) was added all at once and stirring continued overnight (18 h). After this, the reaction mixture was washed with water (2×25 mL) and brine (25 ml). The organic layer was dried (Na$_2$SO$_4$), filtered and concentrated to give a white slurry which was triturated with hexanes and filtered to afford the title compound as a white solid (20.34 g, 81% yield). $^1$H NMR (500 MHz, CDCl$_3$): 7.59-7.55 (1H, m), 7.45-7.34 (5H, m), 6.75-6.71 (2H, m), 5.19 (2H, s); $^{13}$C NMR (125.76 MHz, DMSO-d6) δ ppm: 71.16, 98.75, 101.54, 101.75, 108.66, 108.84, 115.83, 127.16, 128.58, 128.94, 135.03, 135.44, 135.54, 162.22, 162.31, 165.26, 167.29. LCMS calcd for C$_{14}$H$_{11}$FNO: 228.2; found: 228.0.

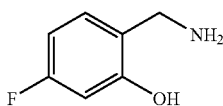

Intermediate 108

2-Hydroxy-4-fluoro-benzylamine hydrochloride. A solution 2-(benzyloxy)-4-fluorobenzonitrile, (9.03 g, 39.7 mmol) in ethanol (100 mL) and ethyl acetate (100 mL) was stirred with 10% palladium on carbon (1.67 g,) and concentrated hydrochloric acid (12 mL, 144 mmol) under a hydrogen atmosphere (60 psi) for four days. The catalyst was removed by filtration through Celite®, and the filtrate was concentrated. The crude product was triturated with ether and the resulting solid collected by filtration to give the title compound (5.24 g, 74% yield) as a pale orange solid. $^1$H NMR (500 MHz, DMSO-D6) δ ppm: 10.81 (1H, s), 8.18 (3H, s), 7.36 (1 H, t, J=7.3 Hz), 6.79 (1H, dd, J=10.8, 2.6 Hz), 6.66 (1H, dt, J=8.5, 2.3 Hz), 3.90 (2 H, d, J=5.2 Hz).

Intermediate 109

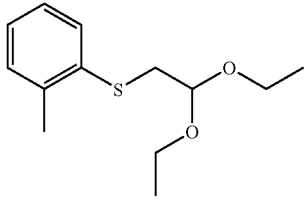

(2,2-Diethoxyethyl)(o-tolyl)sulfane. In ethanol (50 mL) was dissolved sodium metal (1.6 g, 66 mmol) at 23° C. 2-Methylbenzenethiol (8.1 mL, 68 mmol) was slowly added to this solution, followed by bromoacetaldehyde diethylacetal (9.50 mL, 63 mmol). The reaction mixture was stirred at reflux for 18 h. The solvent was then evaporated in vacuo and the residue was washed with H$_2$O (100 mL) and extracted with ether (100 mL). The organic solution was dried (MgSO$_4$), concentrated in vacuo and purified by distillation to afford the title compound (13.48 g, 82% yield): $^1$H NMR (400 MHz, CDCl$_3$) δ ppm: 7.33 (1H, d, J=7.9 Hz), 7.16-7.08 (3H, m), 4.65 (1H, t, J=5.6 Hz), 3.66 (2H, q, J=7.0 Hz), 3.55 (2H, q, J=7.0 Hz), 3.09 (2H, d, J=5.6 Hz), 2.38 (3H, s), 1.20 (6H, t, J=7.0 Hz). LCMS (M+H)$^+$ m/z 241 (t=2.65 min.).

Intermediate 110

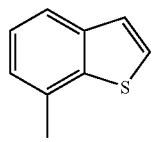

7-Methylbenzo[b]thiophene. To a solution of (2,2-diethoxyethyl)(o-tolyl)sulfane (0.58 g, 2.41 mmol) in chlorobenzene (20 mL) was added polyphosphoric acid. The reaction mixture was stirred at reflux for 18 h. Water (100 mL) was then added and the organic material was extracted with CH$_2$Cl$_2$ (2×50 mL). The organic solution was dried (MgSO$_4$) and concentrated in vacuo to afford 335 mg (94% yield) of the title compound: $^1$H NMR (400 MHz, CDCl$_3$) δ: 7.68 (1H, d, J=7.8 Hz), 7.43 (1H, d, J=5.4 Hz), 7.36 (1H, d, J=5.4 Hz), 7.30 (1H, dd, J=7.8, 7.1 Hz), 7.14 (1H, d, J=7.1 Hz), 2.58 (3H, s); LCMS (M+H)$^+$ m/z 148.

Intermediate 111

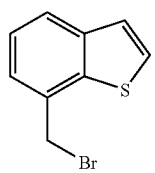

7-(Bromomethyl)benzo[b]thiophene. To a solution of 7-methylbenzo[b]thiophene (1.0 g, 6.5 mmol) in CCl$_4$ (20 mL) was added benzoyl peroxide (1.1 g, 4.54 mmol) followed by portionwise addition of NBS (1.15 g, 6.5 mmol). The reaction mixture stirred at reflux while irradiating with a 250 W lamp. The reaction mixture was stirred at reflux for 3 h. The solution was cooled, filtered and the solvent evaporated in vacuo. The residue was subjected to column chromatography on silica gel with hexanes as the eluent to afford the title compound (0.570 g, 33% yield): $^1$H NMR (400 MHz, CDCl$_3$) δ: 7.80 (1H, dd, J=7.8, 1.7 Hz), 7.49 (1H, d, J=5.4 Hz), 7.40-7.33 (3H, m), 4.78 (2H, s). LCMS (M+H)$^+$ m/z 209.

Intermediate 112

Benzo[b]thiophen-7-ylmethanamine hydrochloride. To 7-(bromomethyl)benzo[b]thiophene (0.20 g, 0.96 mmol) was added a methanolic solution saturated with ammonia (30 mL). The reaction mixture was heated in a steel bomb at 70° C. for 18 h. The solvent was evaporated in vacuo and the residue was dissolved in MeOH (10 mL). HCl (1M in ethanol, 1 mL) was added to the solution and the solvents were removed in vacuo to afford the title compound (0.177 g, 99% yield); LCMS (M+H)$^+$ m/z 164.

Intermediate 113

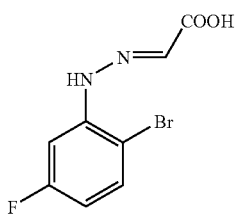

2-(2-(2-Bromo-5-fluorophenyl)hydrazono)acetic acid: To a solution of (2-bromo-5-fluorophenyl)hydrazine (2.15 g, 10.5 mmol) and concentrated HCl (1.2 mL) in water (30 mL) was added glyoxylic acid hydrate (1.06 g, 11.5 mmol). The resulting mixture was stirred at room temperature for 2 h. The precipitate that formed was collected by filtration, washed with water and dried at reduced pressure to afford the title compound as a yellow solid (2.67 g, 98% yield): $^1$H NMR (400 MHz, DMSO-D6) δ ppm 12.57 (1H, s), 10.65 (1H, s), 7.65 (1H, s), 7.56 (1H, dd, J=8.7, 5.9 Hz), 7.31 (1H, dd, J=11.4, 3.0 Hz), 6.73 (1H, td, J=8.5, 3.0 Hz); LCMS ($^+$ESI, M+H$^+$) m/z 261-263.

Intermediate 114

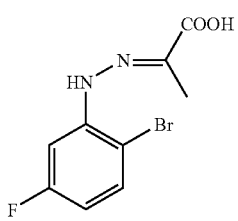

2-(2-(2-Bromo-5-fluorophenyl)hydrazono)propanoic acid: $^1$H NMR (400 MHz, DMSO-D6) δ ppm 12.48 (1H, brs), 8.51 (1H, s), 7.53-7.65 (2H, m), 6.70-6.81 (1H, m), 2.13 (3H, s); LCMS ($^+$ESI, M+H$^+$) m/z 275-277.

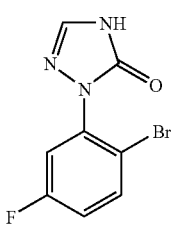

Intermediate 115

1-(2-Bromo-5-fluorophenyl)-1H-1,2,4-triazol-5(4H)-one: To a stirred suspension of 2-(2-(2-bromo-5-fluorophenyl)hydrazono)acetic acid (2.65 g, 10.2 mmol) in toluene (80 mL) was added triethylamine (1.42 mL, 10.2 mmol) and diphenylphosphoryl azide (2.2 mL, 10.2 mmol). The resulting mixture was slowly heated to reflux temperature and the reflux was maintained for 1 h. The clear orange solution was cooled and then poured onto 10% aqueous KOH (100 mL). The basic extract was acidified (pH 1) with concentrated HCl. The precipitate that formed was collected by filtration, washed with water and dried at reduced pressure to afford the title compound as a yellow solid (1.75 g, 67% yield): $^1$H NMR (400 MHz, DMSO-D6) δ ppm 11.87 (1H, s), 8.10-8.08 (1H, m), 7.83 (1H, dd, J=8.8, 5.8 Hz), 7.50 (1 H, dd, J=9.1, 3.0 Hz), 7.34 (1H, td, J=8.6, 3.0 Hz); LCMS ($^+$ESI, M+H$^+$) m/z 258-260.

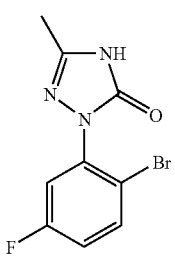

Intermediate 116

1-(2-Bromo-5-fluorophenyl)-3-methyl-1H-1,2,4-triazol-5(4H)-one: $^1$H NMR (400 MHz, CDCl$_3$) δ ppm 11.74 (1H, brs), 7.70 (1H, dd, J=9.0, 5.4 Hz), 7.26 (1H, dd, J=8.5, 2.9 Hz), 7.10 (1H, td, J=8.6, 2.9 Hz), 2.31 (3H, s); LCMS ($^+$ESI, M+H$^+$) m/z 272-274.

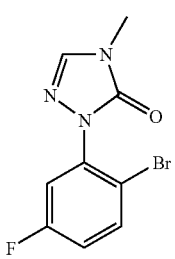

Intermediate 117

1-(2-Bromo-5-fluorophenyl)-4-methyl-1H-1,2,4-triazol-5(4H)-one: To a stirred suspension of sodium hydride (0.124 g of a 60% dispersion in mineral oil, 3.09 mmol) in DMF (5 mL) was added a solution of 1-(2-bromo-5-fluorophenyl)-1H-1,2,4-triazol-5(4H)-one (0.725 g, 2.81 mmol) in DMF (5 mL) at 0° C. The resulting mixture was stirred 45 min at room temperature followed by the addition of iodomethane (0.23 mL, 3.65 mmol). The mixture was stirred at room temperature for 2 h and then poured onto saturated aqueous NH$_4$Cl. The product was extracted with EtOAc, washed with water (3×), brine, dried over Na$_2$SO$_4$ and filtered. The residue was purified with a Biotage column chromatography system on silica gel with hexanes:ethyl acetate (3:7) gradient as the eluent to afford the title compound as a white solid (0.508 g, 66% yield): $^1$H NMR (400 MHz, CDCl$_3$) δ 7.65 (1H, dd, J=9.0, 5.4 Hz), 7.56 (1H, s), 7.20 (1H, dd, J=8.6, 3.0 Hz), 7.04 (1H, ddd, J=8.9, 7.6, 2.9 Hz), 3.39 (3H, s); LCMS (ESI, M+H$^+$) m/z 272-274.

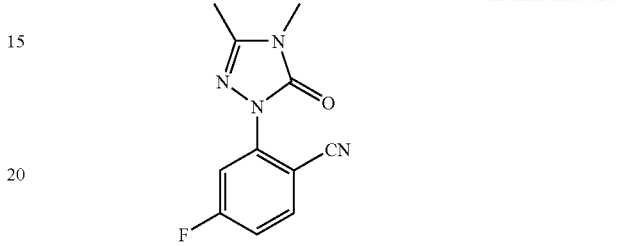

Intermediate 118

2-(3,4-Dimethyl-5-oxo-4,5-dihydro-1H-1,2,4-triazol-1-yl)-4-fluorobenzonitrile: $^1$H NMR (400 MHz, CDCl$_3$) δ 7.76 (1H, dd, J=8.6, 5.8 Hz), 7.72 (1H, dd, J=9.9, 2.5 Hz), 7.09 (1H, ddd, J=8.7, 7.5, 2.5 Hz), 3.34 (3H, s), 2.36 (3H, s); LCMS ($^+$ESI, M+H$^+$) n/z 233.

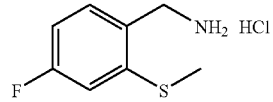

Intermediate 119

4-Fluoro-2-methylsulfanyl-benzylamine. 4-Fluoro-2-(methylthio)benzonitrile (prepared as in Anthony, N. J. et al. PCT Appl. WO 02/30931, 2002) (1.67 g, 0.1 mol) was dissolved in 20 mL THF (under N$_2$) and treated with 10 mL 2M BH$_3$—(CH$_3$)$_2$S. This was heated at 60° C. for 2 hrs. Heating was discontinued and 5 mL MeOH was cautiously added, followed by the cautious addition of 4 mL 6N HCl. Then 20 mL more H$_2$O added and EtOAc and the layers were separated. The aqueous layer was made basic with 1N NaOH and extracted with CH$_2$Cl$_2$. The extracts were dried (MgSO$_4$), filtered, concentrated and dried in vacuum to give the title compound (1.3 g, 76%)as a solid. $^1$H NMR (500 MHz, CDCl$_3$) δ: 7.20-7.31 (1 H, m) 6.90 (1H, dd, J=2.4 Hz) 6.75-6.86 (1H, m) 3.86 (2H, s) 2.47 (3H, s). LC/MS (M+H): 172.

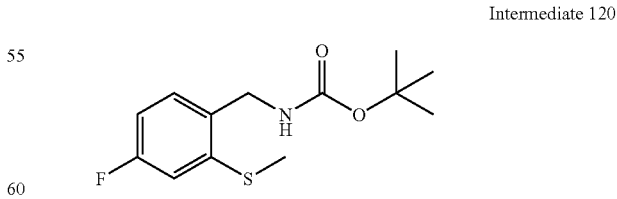

Intermediate 120

N-t-Butoxycarbonyl-(4-fluoro-2-(methylthio)phenyl)methanamine. A stirred solution of 4-fluoro-2-methylsulfanyl-benzylamine (5.1 g, 0.03 mol) and 3.3 g triethylamine in 100 mL CH$_2$Cl$_2$ under N2 was treated with di-t-butyl dicarbonate (7.2 g, 0.033 mol) portionwise and stirred at room temperature for 30 min. The reaction mixture was then washed with dilute (aqueous) HCl and water. The organic layer was dried over MgSO$_4$, filtered and concentrated to leave 8.1 g (100% yield) of the title compound as a clear oil. $^1$H NMR (500 MHz, CDCl$_3$) δ: 7.22-7.29 (1H, m) 6.89 (1H, dd, J=9.61, 2.29 Hz) 6.75-6.83 (1H, m) 4.93 (1H, s) 4.31 (2H, d, J=5.49 Hz) 2.47 (3H, s) 1.44 (9H, s). LC/MS (M+H): 272.

Intermediate 121

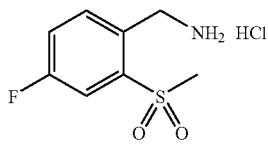

(4-Fluoro-2-(methylsulfonyl)phenyl)methanamine hydrochloride. A solution of N-t-butoxycarbonyl-(4-fluoro-2-(methylthio)phenyl)methanamine (8.1 g, 0.03 mol) in 100 mL acetone and 50 mL water was treated with oxone (18.5 g, 0.03 mol) and stirred for 10 min. Then an additional 18.5 g oxone was added and the mixture was warmed at 60° C. for 1.5 hrs. This was cooled, concentrated to remove acetone and extracted with CH$_2$Cl$_2$. This was concentrated to an oil, dissolved in 20 mL ethanol and treated with 10 mL 6N HCl and warmed at 60° C. for 2 h. Removal of the solvent gave a gum which was crystallized from ethanol to the title compound (2.0 g) as crystals. Additional material was obtained by neutralizing the aqueous solution and extracting the free base with CH$_2$Cl$_2$. $^1$H NMR (500 MHz, DMSO-D$_6$) δ: 8.54 (3 H, s) 7.89 (1H, dd, J=8.54, 5.19 Hz) 7.67-7.85 (2H, m) 4.40 (2H, s) 3.41 (3 H, s). LC/MS (M+H)=204.

Intermediate 122

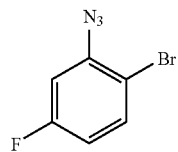

2-Azido-1-bromo-4-fluorobenzene: 2-Bromo-5-fluoro aniline (2.00 g, 10.53 mmol) was dissolved in concentrated HCl (10 mL) and water (10 mL) and cooled to 0° C. Aqueous NaNO$_2$ solution (1.090 g, 15.8 mmol of NaNO$_2$ in 10 mL of water) was added dropwise at such a rate that the temperature did not exceed 5° C. This mixture was stirred at 0° C. for 1.5 h. A solution of NaN$_3$ (1.027 g, 15.8 mmol) and NaOAc (12.95 g, 158 mmol) in water (50 mL) was then added at 0-5° C. and the mixture was stirred for an additional 1 h at this temperature. The mixture was extracted with EtOAc and the combined extracts were washed with brine and dried over Na$_2$SO$_4$. The filtrate was concentrated to afford the title compound as a tan solid (2.188 g, 96% yield): $^1$H NMR (400 MHz, CDCl$_3$) δ: 7.53 (1H, dd, J=8.8, 5.6 Hz), 6.94 (1H, dd, J=8.8, 2.8 Hz), 6.79 (1H, ddd, J=8.8, 7.6, 2.8 Hz).

Intermediate 123

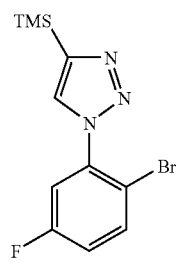

1-(2-Bromo-5-fluorophenyl)-4-(trimethylsilyl)-1H-1,2,3-triazole: A mixture of 2-azido-1-bromo-4-fluorobenzene (1.05 g, 4.85 mmol) and trimethylsilylacetylene (2.01 mL, 14.54 mmol) in toluene (5 mL) was heated in a pressure vessel at 110° C. for 21.5 h. The reaction mixture was concentrated in vacuo and the residue was purified with a Biotage column chromatography system on silica gel with hexanes:ethyl acetate (9:1) gradient as the eluent to afford the title compound as a colorless oil (1.45 g, 95% yield): $^1$H NMR (400 MHz, CDCl$_3$) δ: 7.97 (1H, s), 7.74 (1H, dd, J=9.0, 5.4 Hz), 7.37 (1H, dd, J=8.5, 2.9 Hz), 7.16 (1H, ddd, J=8.8, 7.6, 3.0 Hz), 0.40 (9H, s), LCMS ($^+$ESI, M+H$^+$) m/z 314/316.

Intermediate 124

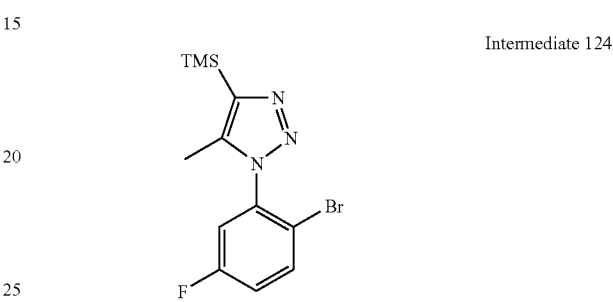

1-(2-Bromo-5-fluorophenyl)-5-methyl-4-(trimethylsilyl)-1H-1,2,3-triazole: The title compound was prepared according to an analogous procedure provided for 1-(2-bromo-5-fluorophenyl)-4-(trimethylsilyl)-1H-1,2,3-triazole. $^1$H NMR (400 MHz, CDCl$_3$) δ: 7.73-7.69 (1H, m), 7.20-7.16 (2H, m), 2.22 (3H, s), 0.39 (9H, s); LCMS ($^+$ESI, M+H$^+$) m/z 328/330.

Intermediate 125

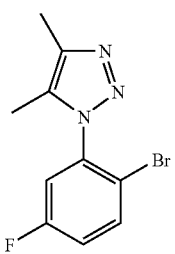

1-(2-bromo-5-fluorophenyl)-4,5-dimethyl-1H-1,2,3-triazole: The title compound was prepared according to an analogous procedure provided for 1-(2-bromo-5-fluorophenyl)-4-(trimethylsilyl)-1H-1,2,3-triazole. $^1$H NMR (400 MHz, CDCl$_3$) δ: 7.71 (1H, dd, J=8.8, 5.3 Hz), 7.12-7.20 (2H, m), 2.34 (3H, s), 2.12 (3 H, s), LCMS ($^+$ESI, M+H$^+$) m/z 270/272.

Intermediate 126

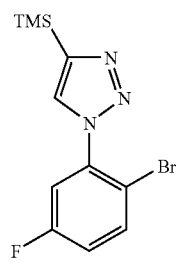

1-(2-Bromo-5-fluorophenyl)-1H-1,2,3-triazole: 1-(2-Bromo-5-fluorophenyl)-4-(trimethylsilyl)-1H-1,2,3-triazole (0.800 g, 2.55 mmol) was dissolved in THF (10 mL) and tetrabutylammonium fluoride (2.8 mL, 2.80 mmol, 1.0 M in THF) was added dropwise and the reaction mixture was stirred at 25° C. for 4 h. The resulting mixture was concentrated in vacuo and the residue was purified with a Biotage column chromatography system on silica gel with a hexanes:ethyl acetate (8:2 to 7:3) gradient as the eluent to afford the title compound as a white solid (0.36 g, 58% yield): $^1$H NMR (400 MHz, CDCl$_3$) δ: 8.06 (1H, d, J=1.0 Hz), 7.90 (1H, d, J=1.3 Hz), 7.76 (1H, dd, J=8.8, 5.3 Hz), 7.39 (1H, dd, J=8.3, 2.8 Hz), 7.19 (1H, ddd, J=8.9, 7.5, 3.0 Hz), LCMS ($^+$ESI, M+H$^+$) m/z 242/244.

Intermediate 127

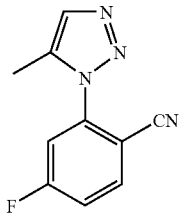

1-(2-Bromo-5-fluorophenyl)-5-methyl-1H-1,2,3-triazole. The title compound was prepared according to an analogous procedure provided for 1-(2-bromo-5-fluorophenyl)-1H-1,2,3-triazole. $^1$H NMR (400 MHz, CDCl$_3$) δ: 7.76 (1H, dd, J=9.1, 5.3 Hz), 7.62 (1H, s), 7.19-7.26 (2H, m), 2.25 (3H, s), LCMS ($^+$ESI, M+H$^+$) m/z 256/258.

Intermediate 128

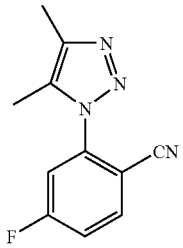

4-Fluoro-2-(1H-1,2,3-triazol-1-yl)benzonitrile: A mixture of 1-(2-bromo-5-fluorophenyl)-1H-1,2,3-triazole (0.603 g, 2.49 mmol), CuCN (0.245 g, 2.74 mmol), in 15 mL of NMP was subjected to microwave irradiation at 150° C. for 0.5 h. The brown mixture was filtered over Celite® and washed with DMF. This solution was treated with 10% aqueous NH$_4$OH (28-30% solution) and extracted with EtOAc. The organic fractions were combined and successively washed with 10% aqueous NH$_4$OH (28-30% solution), saturated aqueous NH$_4$Cl, water, brine and dried over $Na_2SO_4$. The resulting mixture was concentrated in vacuo and the residue was purified with a Biotage column chromatography system on silica gel with hexanes:ethyl acetate (7:3 to 6:4) gradient as the eluent to afford the title compound as a light yellow solid (0.285 g, 61% yield): $^1$H NMR (400 MHz, CDCl$_3$) δ: 8.40 (1H, d, J=1.0 Hz), 7.96 (1H, s), 7.91 (1H, dd, J=8.6, 5.6 Hz), 7.77 (1H, dd, J=8.7, 2.4 Hz), 7.31-7.39 (1H, m).

Intermediate 129

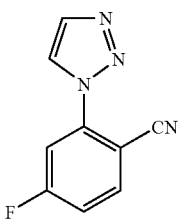

4-Fluoro-2-(5-methyl-1H-1,2,3-triazol-1-yl)benzonitrile. The title compound was prepared according to an analogous procedure provided for 4-fluoro-2-(1H-1,2,3-triazol-1-yl)benzonitrile. $^1$H NMR (400 MHz, CDCl$_3$) δ: 7.93 (1H, dd, J=8.7, 5.4 Hz), 7.67 (1H, s), 7.44 (1H, ddd, J=8.6, 7.6, 2.5 Hz), 7.35 (1H, dd, J=8.1, 2.5 Hz), 2.39 (3H, s), LCMS ($^+$ESI, M+H$^+$) m/z 203.

Intermediate 130

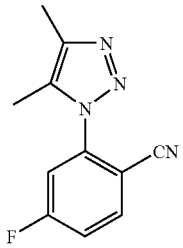

2-(4,5-dimethyl-1H-1,2,3-triazol-1-yl)-4-fluorobenzonitrile. The title compound was prepared according to an analogous procedure provided for 4-fluoro-2-(1H-1,2,3-triazol-1-yl)benzonitrile. $^1$H NMR (400 MHz, CDCl$_3$) δ: 7.88 (1H, dd, J=8.1, 2.5 Hz), J=8.7, 5.4 Hz), 7.38 (1H, ddd, J=8.7, 7.5, 2.5 Hz), 7.29 (1H, dd, J=8.1, 2.5 Hz), 2.37 (3H, s), 2.26 (3H, s), LCMS ($^+$ESI, M+H$^+$) m/z 217.

Intermediate 131

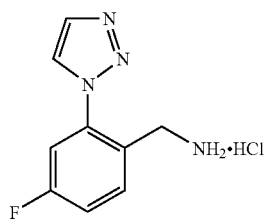

(4-Fluoro-2-(1H-1,2,3-triazol-1-yl)phenyl)methanamine hydrochloride. $^1$H NMR (400 MHz, DMSO-D6) δ: 8.73 (1H, d, J=1.0 Hz), 8.53 (3H, brs), 8.07 (1H, d, J=1.0 Hz), 7.91 (1H, dd, J=8.7, 5.9 Hz), 7.66 (1H, dd, J=9.2, 2.7 Hz), 7.60 (1H, td, J=8.5, 2.7 Hz), 3.92 (2H, q, J=5.6 Hz), LCMS ($^+$ESI, M+H$^+$) m/z 193.

Intermediate 132

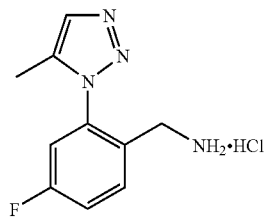

(4-Fluoro-2-(5-methyl-1H-1,2,3-triazol-1-yl)phenyl)methanamine hydrochloride: ¹H NMR (400 MHz, DMSO-D6) δ: 8.61 (2H, s), 7.98 (1H, dd, J=9.5, 6.2 Hz), 7.80 (1H, s), 7.61-7.67 (2H, m), 3.66 (2H, q, J=5.7 Hz), 2.26 (3H, s), LCMS (⁺ESI, M+H⁺) m/z 206.

Intermediate 133

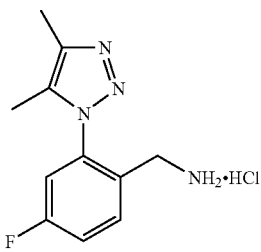

(2-(4,5-dimethyl-1H-1,2,3-triazol-1-yl)-4-fluorophenyl)methanamine hydrochloride. ¹H NMR (400 MHz, DMSO-D6) δ: 8.58 (2H, s), 7.96 (1H, dd, J=8.7, 5.9 Hz), 7.56-7.65 (2H, m), 2.46-2.52 (2H, m), 2.30 (3H, s), 2.18 (3H, s), LCMS (⁺ESI, M+H⁺) m/z 221.

Intermediate 134

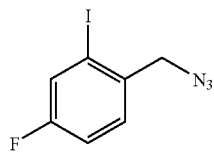

1-(Azidomethyl)-4-fluoro-2-iodobenzene: A solution of 1-(bromomethyl)-4-fluoro-2-iodobenzene (M. Protiva et al., Collect. Czech. Chem. Comm., 44, 1979, 2108-2123) (17.9 g, 56.8 mmol) in N,N-dimethylformamide (35 ml) was treated with sodium azide (5.0 g, 76.7 mmol) and the resulting mixture was heated to 50° C. for 4 h. The cooled mixture was filtered, the filtrate was concentrated in vacuo and the residue was chromatographed on silica gel (elution hexane) to give 15.7 g (97% yield) of the title azide as a clear oil. ¹HNMR 400 MHz (DMSO-d₆) δ: 4.53 (2H, s), 7.32 (1H, m), 7.54 (1H, dd, J=6.0, 8.6 Hz), 7.83 (1H, dd, J=3.0, 8.0 Hz).

Intermediate 135

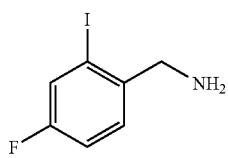

(4-Fluoro-2-iodophenyl)methanamine: A solution of 1-(azidomethyl)-4-fluoro-2-iodobenzene (15.2 g, 54.8 mmol) in DMF (35 ml) at 0° C. was treated with triphenylphosphine (21.6 g, 81.2 mmol) and then stirred for 1 h. The reaction mixture was then treated with water (5 ml) and heated at 55° C. for 1 h. The DMF was concentrated in vacuo and the residue was diluted with ethyl acetate (200 ml). The organic phase was extracted with 0.5 N hydrochloric acid (140 ml) and the aqueous extract was washed with ethyl acetate. The aqueous phase was then adjusted to pH 9 with 1 N LiOH and extracted with ethyl acetate (2×200 ml). The combined organic phases were dried over anhydrous magnesium sulfate and concentrated. The residue was diluted with ether (200 ml), filtered and concentrated. Distillation of the residue in vacuo gave 8.52 g (62% yield) of the title amine as a clear oil: bp 85° C./0.35 torr (bulb to bulb distillation air bath temperature). ¹HNMR 400 MHz (DMSO-d₆) δ: 3.64 (2H, s), 7.27 (1H, m), 7.53 (1H, dd, J=6.0, 8.6 Hz), 7.83 (1H, dd, J=3.0, 8.0 Hz).

Intermediate 136

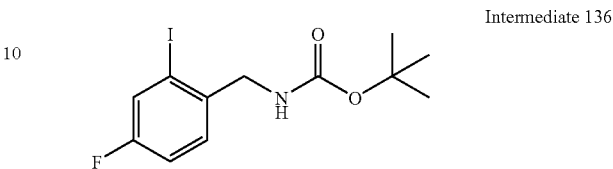

tert-Butyl 4-fluoro-2-iodobenzylcarbamate: A solution of (4-fluoro-2-iodophenyl)methanamine (21.4 g, 85.2 mmol) in dichloromethane (350 ml) was treated at 0° C. with di-tert-butyl dicarbonate (20.5 g, 93.8 mmol) followed by triethylamine added drop wise over 30 min. The resulting mixture was then allowed to warm up to 25° C. and stirred for 18 h. The reaction mixture was then washed with water, brine, dried over anhydrous magnesium and concentrated. Chromatography of the residue on silica gel (elution gradient of ethyl acetate 5-20% in hexane) gave 28.37 g (95% yield) of the title carbamate as a clear oil. ¹HNMR 400 MHz (CDCl₃) δ: 1.47 (9H, s), 4.32 (2H, d, J=6.0 Hz), 5.04 (1H, broad), 7.07 (1H, m), 7.35 (1H, m), 7.56 (1H, dd, J 2.8, 8.0 Hz).

Intermediate 137

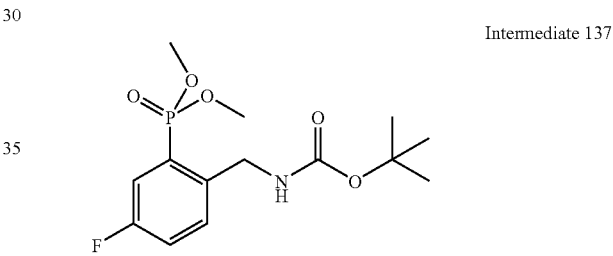

tert-Butyl 2-(dimethoxyphosphoryl)-4-fluorobenzylcarbamate: A solution of tert-butyl 4-fluoro-2-iodobenzylcarbamate (5.00 g, 14.24 mmol), dimethyl phosphite (4.70 g, 42.7 mmol) and N,N-diisopropylethylamine (9.9 ml, 56.8 mmol) in methanol (75 ml) was flushed with argon and then treated with triphenylphosphine (0.5 g) and palladium(II) acetate (0.75 g). The resulting mixture was then sealed and heated at 100° C. for 1 hour. The cooled reaction mixture was concentrated in vacuo, diluted with ethyl acetate, washed with water, brine, dried over anhydrous magnesium and concentrated. Chromatography of the residue on silica gel (elution gradient of acetonitrile in dichloromethane) gave 3.24 g (68% yield) of the title phosphonate as a clear oil. ¹HNMR 400 MHz (CDCl₃) δ: 1.44 (9H, s), 3.81 (3H, s), 3.84 (3H, s), 4.49 (2H, d, J=6.0 Hz), 5.7 (1H, broad), 7.24 (1H, m), 7.47-7.7 (2H, m). HRMS (ESI⁺) calculated for $C_{14}H_{22}FNO_5P$ [M+H⁺]: 334.1220; found: 334.1217.

Intermediate 138

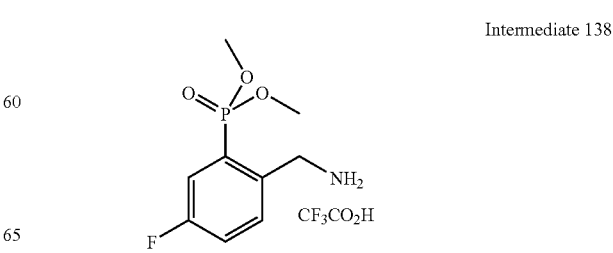

Dimethyl 2-(aminomethyl)-5-fluorophenylphosphonate trifluoroacetic acid salt: A solution of tert-butyl 2-(dimethoxyphosphoryl)-4-fluorobenzylcarbamate (0.140 g, 0.42 mmol) in dichloromethane (5 ml) was treated with trifluoroacetic acid (5 ml) and the resulting mixture was stirred at 25° C. for 1 h. The solvent was then evaporated in vacuo to give the title amine salt as an amorphous white solid. MS (ESI$^+$) m/z 234 [M+H$^+$].

Intermediate 139

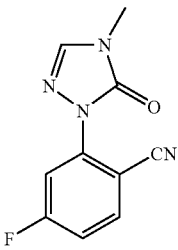

4-Fluoro-2-(4-methyl-5-oxo-4,5-dihydro-1H-1,2,4-triazol-1-yl)benzonitrile: A mixture of 1-(2-bromo-5-fluorophenyl)-4-methyl-1H-1,2,4-triazol-5(4H)-one (0.484 g, 1.78 mmol), CuCN (0.319 g, 3.56 mmol), and 8 mL of NMP was subjected to microwave irradiation at 120° C. for 3 h. The brown mixture was filtered over Celite® and washed with DMF. This solution was treated with 10% aqueous NH$_4$OH (28-30% solution) and extracted with EtOAc. The combined organic fractions were successively washed with 10% aqueous NH$_4$OH (28-30% solution), saturated aqueous NH$_4$Cl, water, brine and dried over Na$_2$SO$_4$. The resulting mixture was concentrated in vacuo and the residue was purified with a Biotage column chromatography system on silica gel with hexanes:ethyl acetate (3:7 to 2:8) gradient as the eluent to afford the title compound as a pink solid (0.305 g, 79% yield): $^1$H NMR (400 MHz, CDCl$_3$) δ 7.76 (1H, dd, J=8.8, 5.8 Hz), 7.72 (1H, dd, J=9.6, 2.5 Hz), 7.64 (1H, s), 7.10 (1H, ddd, J=8.7, 7.4, 2.7 Hz), 3.40 (3H, s); LCMS ($^+$ESI, M+H$^+$) m/z 219.

Intermediate 140

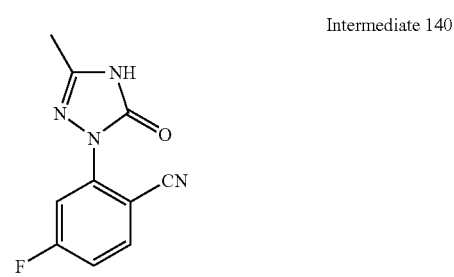

4-Fluoro-2-(3-methyl-5-oxo-4,5-dihydro-1H-1,2,4-triazol-1-yl)benzonitrile: $^1$H NMR (400 MHz, CDCl$_3$) δ 11.24 (1H, brs), 7.80 (1H, J=8.8, 5.8 Hz), 7.63 (1H, dd, J=9.3, 2.5 Hz), 7.16 (1H, ddd, J=8.7, 7.5, 2.5 Hz), 2.38 (3H, s). LCMS ($^+$ESI, M+H$^+$) m/z 219.

Intermediate 141

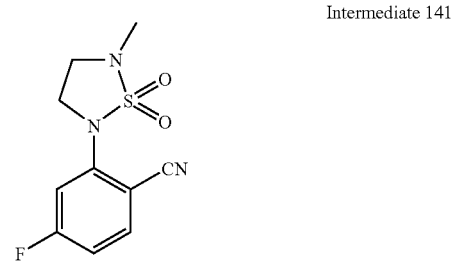

4-Fluoro-2-(1,1-dioxo-5-methyl-1,2,5-thiazolidin-2-yl)benzonitrile: A high pressure reaction vessel containing 2-bromo-4-fluorobenzonitrile (0.250 g, 1.25 mmol), 2-(methyl)-1,2,5-thiadiazolidine 1,1-dioxide (0.204 g, 1.5 mmol), K$_2$CO$_3$ (0.242 g, 1.4 mmol) and xantphos (0.058 g, 0.1 mmol) in dioxane (6 mL) was degassed with argon for 15 min. Pd$_2$dba$_3$ (0.034 g, 0.08 mmol) was introduced and the reaction mixture was heated at 100° C. for 9 h. The mixture was cooled, diluted with dioxane, and then filtered through Celite®. The resulting mixture was concentrated in vacuo and the residue was purified with a Biotage column chromatography system on silica gel with hexanes:ethyl acetate (7:3) gradient as the eluent to afford the title compound as a white solid (0.152 g, 48%): $^1$H NMR (400 MHz, CDCl$_3$) δ 7.69 (2H, dd, J=8.6, 5.8 Hz), 7.52 (2H, dd, J=9.5, 2.4 Hz), 7.09 (2 H, ddd, J=8.7, 7.4, 2.4 Hz), 4.06 (3H, t, J=6.4 Hz), 3.56 (3H, t, J=6.6 Hz), 2.90 (3 H, s); LCMS ($^+$ESI, M+H$^+$) m/z 256.

Intermediate 142

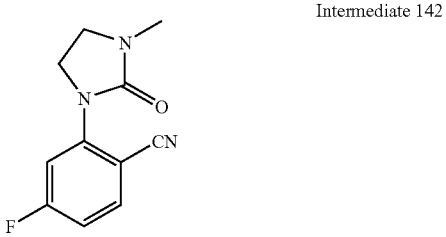

4-Fluoro-2-(3-methyl-2-oxoimidazolidin-1-yl)benzonitrile: $^1$H NMR (400 MHz, CDCl$_3$) δ 7.65 (1H, dd, J=8.7, 5.9 Hz), 7.45 (1H, dd, J=10.4, 2.5 Hz), 6.96 (1 H, ddd, J=8.7, 7.5, 2.5 Hz), 4.08 (2H, dd, J=8.7, 6.9 Hz), 3.55 (2H, dd, J=8.7, 6.0 Hz), 2.93-2.93 (3H, s), 1.55-1.61 (4H, m); LCMS ($^+$ESI, M+H$^+$) m/z 220.

Intermediate 143

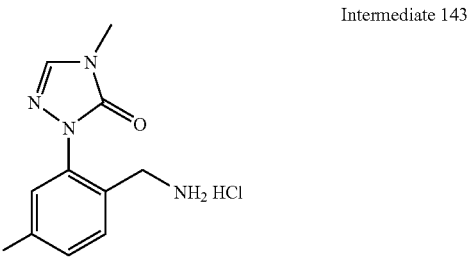

1-(2-(Aminomethyl)-5-fluorophenyl)-4-methyl-1H-1,2, 4-triazol-5(4H)-one hydrochloride: $^1$H NMR (400 MHz, DMSO-D6) δ 8.36 (2H, brs), 8.30 (1H, s), 7.70-7.77 (1H, m), 7.36-7.41 (2H, m), 4.02 (2H, s), 3.27 (3H, s); LCMS ($^+$ESI, M+H$^+$) m/z 223.

Intermediate 144

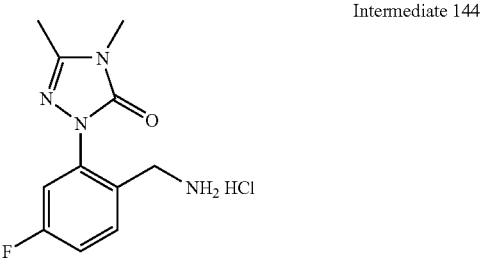

1-(2-(Aminomethyl)-5-fluorophenyl)-3,4-dimethyl-1H-1,2,4-triazol-5(4H)-one hydrochloride: ¹H NMR (400 MHz, DMSO-D6) δ 8.32 (2H, brs), 7.72 (1H, dd, J=8.6, 6.6 Hz), 7.33-7.40 (2H, m), 4.03 (2H, s), 3.24 (3H, s), 2.30 (3H, s); LCMS (⁺ESI, M+H⁺) m/z 237.

Intermediate 145

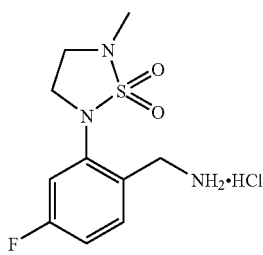

2-Methyl-5-(2-(aminomethyl)-5-fluorophenyl)-1,2,5-thiadiazolidine 1,1-dioxide hydrochloride: ¹H NMR (400 MHz, DMSO-D6) δ 8.49 (2H, brs), 7.73 (1H, dd, J=8.8, 6.3 Hz), 7.50 (1H, dd, J=10.0, 2.7 Hz), 7.39 (1H, td, J=8.5, 2.8 Hz), 4.14 (2H, brs), 3.91 (2H, t, J=6.4 Hz), 3.50 (2H, t, J=6.3 Hz), 2.74 (3H, s); LCMS (⁺ESI, M+H⁺) m/z 260.

Intermediate 146

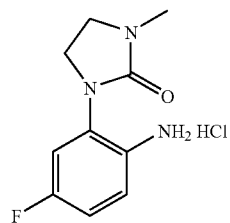

1-(2-(Aminomethyl)-5-fluorophenyl)-3-methylimidazolidin-2-one hydrochloride: ¹H NMR (400 MHz, DMSO-D6) δ 8.28 (2H, brs), 7.65 (1H, dd, J=8.6, 6.6 Hz), 7.35 (1H, dd, J=10.5, 2.5 Hz), 7.22 (1H, td, J=8.6, 2.5 Hz), 3.92-3.80 (4H, m), 3.50 (2H, m), 2.78 (3H, s). LCMS (⁺ESI, M+H⁺) m/z 224.

Intermediate 147

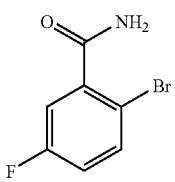

2-Bromo-5-fluorobenzamide. A solution of 2-bromo-5-fluorobenzoic acid (10.0 g, 45.66 mmol) in dichloromethane (100 ml) was treated at 25° C. with oxalyl chloride (8.0 ml, 91.3 mmol) followed by a drop of N,N-dimethylformamide. The resulting mixture was then stirred for 4 h. The solvent and excess reagent were evaporated in vacuo and the residual oil was dissolved in tetrahydrofuran (100 ml) and added to a mixture of tetrahydrofuran (200 ml), water (100 ml) and concentrated ammonium hydroxide (10 ml). The resulting mixture was then stirred at 25° C. for 20 h. The reaction mixture was diluted with ethyl acetate, washed with brine, dried over anhydrous magnesium sulfate and concentrated to give 9.51 g (96% yield) of the title amide as a white solid. ¹HNMR 400 MHz (CDCl₃) δ (ppm): 5.9-6.3 (2H, broad, NH₂), 7.05 (1H, m, aromatic), 7.42 (1H, dd, J=3.2 Hz and J=8.3 Hz, aromatic), 7.61 (1H, dd, J=5.1 Hz and J=9.1 Hz, aromatic).

Intermediate 148

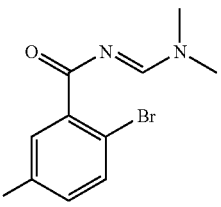

2-Bromo-N-((dimethylamino)methylene)-5-fluorobenzamide. A mixture of 2-bromo-5-fluorobenzamide (9.50 g, 43.57 mmol) and N,N-dimethylformamide dimethyl acetal (20 ml) was heated under argon at 120° C. for 1.5 h. The methanol formed during the reaction was collected through a reflux condenser. The reaction mixture was allowed to cool and the excess N,N-dimethylformamide dimethyl acetal was removed under reduced pressure. The residual oil was crystallized from a mixture of ether (75 ml) and hexane (50 ml) to give 8.55 g (72% yield) of the title material as white crystals. ¹HNMR 400 MHz (CDCl₃) δ (ppm): 3.21 (3H, s, CH₃), 3.24 (3H, s, CH₃), 7.0 (1H, m, aromatic), 7.58 (1H, dd, J=5.0 Hz and J=8.5 Hz, aromatic), 7.64 (1H, dd, J=3.0 Hz and J=9.1 Hz, aromatic), 8.64 (1H, s, CH).

Intermediate 149

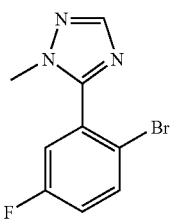

5-(2-Bromo-5-fluorophenyl)-1-methyl-1H-1,2,4-triazole. A solution of 2-bromo-N-((dimethylamino)methylene)-5-fluorobenzamide (22.90 g, 83.84 mmol) in acetic acid (150 ml) was treated with methylhydrazine (5.0 ml, 94.0 mmol) and then heated at 90° C. for 4 h. The solvent and excess reagent were then evaporated in vacuo and the residual oil was diluted with ethyl acetate, washed with saturated sodium bicarbonate, brine, dried over anhydrous magnesium sulfate and concentrated. Column chromatography of the residual oil on silica gel (gradient of ethyl acetate 0-40% in toluene) gave 11.80 g (55% yield) of the title triazole as a white solid. ¹HNMR 400 MHz (CDCl₃) δ (ppm): 3.82 (3H, s, CH₃), 7.15-7.22 (2H, m, aromatics), 7.70 (1H, dd, J=5.1 Hz and J=9.1 Hz, aromatic), 8.02 (1H, s, CH). HRMS (ESI⁺) calculated for C₉H₈BrFN₃ [M+H⁺]: 255.9886; found: 255.9896.

Intermediate 150

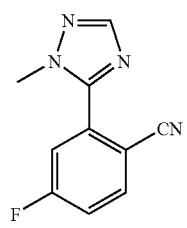

4-Fluoro-2-(1-methyl-1H-1,2,4-triazol-5-yl)benzonitrile. A solution of 5-(2-bromo-5-fluorophenyl)-1-methyl-1H-1,2,4-triazole (1.85 g, 7.22 mmol) in N,N-dimethylformamide (10 ml) was treated with copper (I) cyanide (0.71 g, 7.95 mmol). The mixture was then maintained under vacuum for a few minutes, flushed with argon and heated at 100° C. for 16 h. The solvent was then evaporated in vacuo and the residual oil was diluted with ethyl acetate and washed with a solution of 10% ammonium hydroxide followed by 20% ammonium chloride in water. The organic fraction was then washed with brine, dried over anhydrous magnesium sulfate and concentrated. Column chromatography of the residue on silica gel (elution gradient ethyl acetate 0-40% in toluene) gave 1.09 g (75% yield) of the title nitrile as white crystals: mp 134° C. (ethyl acetate-hexane). $^1$HNMR 400 MHz (CDCl$_3$) δ (ppm): 3.98 (3H, s, CH$_3$), 7.37-7.42 (2H, m, aromatics), 7.90 (1H, dd, J=5.0 Hz and J=8.6 Hz, aromatic), 8.08 (1H, s, CH). Anal. Calcd for C$_{10}$H$_7$FN$_4$: C 59.40, H 3.49, N 27.71; Found: C 59.22, H 3.28, N 27.68.

Intermediate 151

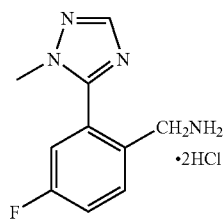

(4-Fluoro-2-(1-methyl-1H-1,2,4-triazol-5-yl)phenyl)methanamine bis hydrochloride. A solution of 4-fluoro-2-(1-methyl-1H-1,2,4-triazol-5-yl)benzonitrile (3.56 g, 17.61 mmol) in acetic acid (180 ml) was hydrogenated at 25° C. over 10% palladium on activated carbon (2 g), under 45 psi of hydrogen for 6 h. The catalyst was removed by filtration. The solvent was evaporated in vacuo and the last traces of acetic acid were removed by co-evaporation with toluene. The residue was diluted with dichloromethane and washed with 25% aqueous sodium hydroxide (20 ml) and brine. The organic fraction was dried over anhydrous magnesium sulfate and concentrated to give 3.56 g of the free base as a clear oil. The oil was diluted with anhydrous ethanol (25 ml) and treated with concentrated hydrochloric acid (8 ml). The solvent was then concentrated in vacuo and the residue was co-evaporated with anhydrous ethanol to give a white solid. Trituration with anhydrous ethanol (~50 ml) gave 4.07 g (83% yield) of the title amine bis-hydrochloride salt as a white solid. $^1$HNMR 400 MHz (DMSO-d$_6$) δ (ppm): 3.90 (3H, s, CH$_3$), 4.01 (2H, m, CH$_2$), 7.55 (1H, m, aromatic), 7.69 (1H, dd, J=2.6 Hz and J=9.5 Hz, aromatic), 7.84 (1H, dd, J=5.5 Hz and J=8.6 Hz, aromatic), 8.18 (1H, s, CH), 8.56 (3H, broad, NH). Anal. Calcd for C$_{10}$H$_{11}$FN$_4$ · 2 HCl: C 43.02, H 4.69, N 20.07; Found: C 43.29, H 4.82, N 19.98.

Intermediate 152

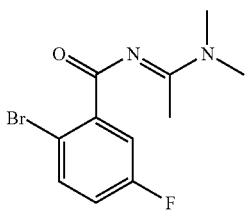

2-Bromo-N-(1-(dimethylamino)ethylidene)-5-fluorobenzamide. A mixture of 2-bromo-5-fluorobenzamide (9.57 g, 43.89 mmol) and N,N-dimethylacetamide dimethyl acetal (20 ml) was heated under argon at 120° C. for 1.5 h. The methanol formed was collected through a reflux condenser. The reaction mixture was allowed to cool and the excess N,N-dimethylacetamide dimethyl acetal was removed under reduced pressure. The residual oil was crystallized from a mixture of ether (30 ml) and hexane (50 ml) to give 9.51 g (75% yield) of the title material as white crystals. $^1$HNMR 400 MHz (CDCl$_3$) δ (ppm): 2.43 (3H, s, CH$_3$), 3.16 (3H, s, NCH$_3$), 3.19 (3H, s, NCH$_3$), 6.90-6.97 (1H, m, aromatic), 7.46 (1H, dd, J=3.1 Hz and J=9.1 Hz, aromatic), 7.53 (1H, dd, J=5.1 Hz and J=9.1 Hz, aromatic). MS (ESI$^+$) m/e 287 [M+H$^+$].

Intermediate 153

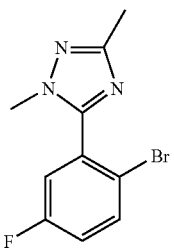

5-(2-Bromo-5-fluorophenyl)-1,3-dimethyl-1H-1,2,4-triazole. A solution of 2-bromo-N-(1-(dimethylamino)ethylidene)-5-fluorobenzamide (4.98 g, 17.34 mmol) in acetic acid (35 ml) was treated with methylhydrazine (0.90 g, 19.1 mmol) and then heated at 90° C. for 2 h. The solvent and excess reagent were then evaporated in vacuo and the residual oil was diluted with ethyl acetate, washed with saturated sodium bicarbonate, brine, dried over anhydrous magnesium sulfate and concentrated. Column chromatography of the residual oil on silica gel (gradient of ethyl acetate in hexane) gave 2.72 g (58% yield) of the title triazole as a white solid. $^1$HNMR 400 MHz (CDCl$_3$) δ (ppm): 2.45 (3H, s, CH$_3$), 3.73 (3H, s, NCH$_3$), 7.11-7.16 (1H, m, aromatic), 7.19 (1H, dd, J=3.1 Hz and J=8.6 Hz, aromatic), 7.67 (1H, dd, J=5.1 Hz and J=9.1 Hz, aromatic). HRMS (ESI$^+$) calculated for C$_{10}$H$_{10}$BrFN$_3$ [M+H$^+$]: 270.0042; found: 270.0037.

Intermediate 154

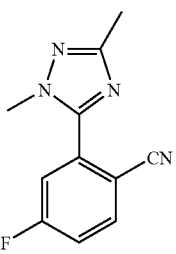

2-(1,3-Dimethyl-1H-1,2,4-triazol-5-yl)-4-fluorobenzonitrile. 5-(2-Bromo-5-fluorophenyl)-1,3-dimethyl-1H-1,2,4-triazole (2.72 g, 10.07 mmol) was treated with copper (I) cyanide to give 1.90 g (87% yield) of the title material as a white solid. $^1$HNMR 400 MHz (CDCl$_3$) δ (ppm): 2.48 (3H, s, CH$_3$), 3.89 (3H, s, NCH$_3$), 7.34-7.42 (2H, m, aromatics), 7.88 (1H, dd, J=5.0 Hz and J=8.6 Hz, aromatic). HRMS (ESI$^+$) calculated for C$_{11}$H$_{10}$FN$_4$ [M+H$^+$]: 217.0889; found: 217.0893.

Intermediate 155

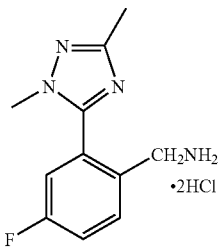

(2-(1,3-Dimethyl-1H-1,2,4-triazol-5-yl)-4-fluorophenyl)methanamine bis hydrochloride. 2-(1,3-Dimethyl-1H-1,2,4-triazol-5-yl)-4-fluorobenzonitrile (7.80 g, 36.1 mmol) was hydrogenated to give 8.76 g (83% yield) the title bis hydrochloride salt as a white solid. $^1$HNMR 400 MHz (DMSO-$d_6$) δ (ppm): 2.32 (3H, s, CH$_3$), 3.80 (3H, s, NCH$_3$), 3.99 (2H, m, CH$_2$), 7.51 (1H, m, aromatic), 7.61 (1H, dd, J=2.7 Hz and J=9.3 Hz, aromatic), 7.82 (1H, dd, J=5.7 Hz and J=8.6 Hz, aromatic), 8.56 (3H, broad, NH). HRMS (ESI$^+$) calculated for C$_{11}$H$_{14}$FN$_4$ [M+H$^+$]: 221.1202; found: 221.1201.

Intermediate 156

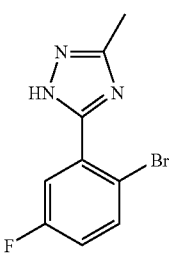

5-(2-Bromo-5-fluorophenyl)-3-methyl-1H-1,2,4-triazole. A solution of 2-bromo-N-(1-(dimethylamino)ethylidene)-5-fluorobenzamide (4.50 g, 15.6 mmol) in acetic acid (35 ml) was treated with hydrazine monohydrate (0.86 g, 17.2 mmol) and then heated at 90° C. for 2 h. The solvent and excess reagent were then evaporated in vacuo and crystallization of the residue from a mixture of ethyl acetate and ether gave 1.90 g (47% yield) of the title triazole as a tan solid. $^1$HNMR 400 MHz (CDCl$_3$) δ (ppm): 2.55 (3H, s, CH$_3$), 7.01-7.06 (1H, m, aromatic), 7.65 (1H, dd, J=5.1 Hz and J=9.1 Hz, aromatic), 7.73 (1H, dd, J=3.2 Hz and J=9.1 Hz, aromatic). HRMS (ESI$^+$) calculated for C$_9$H$_8$BrFN$_3$ [M+H$^+$]: 255.9886; found: 255.9880.

Intermediate 157

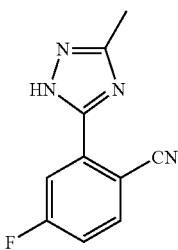

4-Fluoro-2-(3-methyl-1H-1,2,4-triazol-5-yl)benzonitrile. 5-(2-Bromo-5-fluorophenyl)-3-methyl-1H-1,2,4-triazole (4.00 g, 15.6 mmol) was treated with copper (I) cyanide as described in the procedure for intermediate 150 to give 0.83 g (26% yield) of the title material as a white solid. $^1$HNMR 400 MHz (CDCl$_3$) δ (ppm): 2.66 (3H, s, CH$_3$), 7.21-7.25 (1H, m, aromatic), 7.84 (1H, dd, J=5.6 Hz and J=8.6 Hz, aromatic), 8.10 (1H, dd, J=2.8 Hz and J=9.3 Hz, aromatic). HRMS (ESI$^+$) calculated for C$_{10}$H$_8$FN$_4$ [M+H$^+$]: 203.0733; found: 203.0743.

Intermediate 158

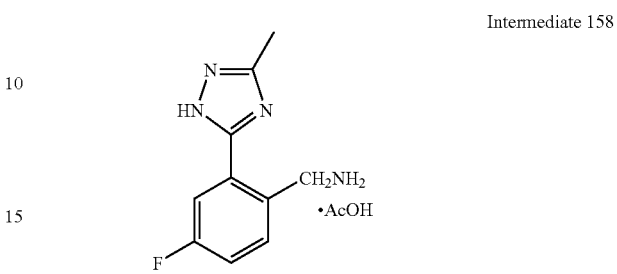

(4-Fluoro-2-(3-methyl-1H-1,2,4-triazol-5-yl)phenyl)methanamine acetic acid salt. 4-Fluoro-2-(3-methyl-1H-1,2,4-triazol-5-yl)benzonitrile (0.803 g, 4.1 mmol) was hydrogenated as described in the procedure for intermediate 151 to give 0.796 g (73% yield) the title acetic acid salt as a white solid. $^1$HNMR 400 MHz (DMSO-$d_6$) δ (ppm): 2.41 (3H, s, CH$_3$), 3.97 (2H, s, CH$_2$), 7.24 (1H, m, aromatic), 7.55 (1H, dd, J=6.1 Hz and J=8.1 Hz, aromatic), 7.66 (1H, dd, J=2.8 Hz and J=10.3 Hz, aromatic). HRMS (ESI$^+$) calculated for C$_{10}$H$_{12}$FN$_4$ [M+H$^+$]: 207.1046; found: 207.1049.

Intermediate 159

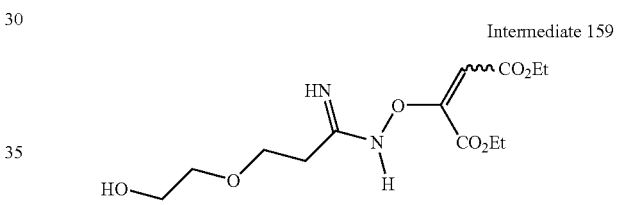

Diethyl 2-(3-(2-hydroxyethoxy)propanimidamidooxy)but-2-enedioate. Treatment of 3-(2-hydroxyethoxy)propanenitrile (9.00 g, 78.1 mmol) with 50% aqueous hydroxylamine (5.16 g, 78.1 mmol) followed by reaction with diethyl acetylenedicarboxylate (13.30 g, 78.1 mmol) gave 21.53 g (86% yield) of the title material as a light yellow oil after chromatography. $^1$HNMR 400 MHz (CDCl$_3$) δ (ppm): (mixture of E/Z isomers ratio~3:1) 1.25-1.4 (6H, 4×t), 2.42-2.49 (2H, m), 3.60-3.79 (6H, m), 4.16-4.21 (2H, m), 4.33-4.38 (2H, m), 5.3 and 5.65 (2H, two broad s), 5.77 and 5.83 (1H, 2×s). MS (ESI$^+$) m/e 319 [M+H$^+$].

Intermediate 160

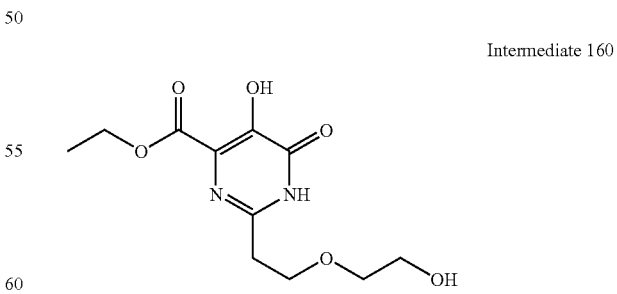

Ethyl 5-hydroxy-2-(2-(2-hydroxyethoxy)ethyl)-6-oxo-1,6-dihydropyrimidine-4-carboxylate. Intermediate 159 (21.5 g, 67.5 mmol) was heated at 150° C. in xylene (400 ml) for 6 h. The solvent was then evaporated in vacuo and the residual oil was used as such for the next step. MS (ESI$^+$) m/e 273 [M+H$^+$].

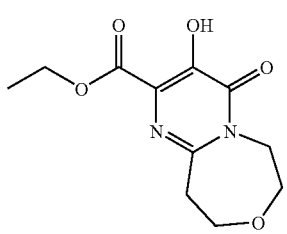

Intermediate 161

Ethyl 3-hydroxy-4-oxo-6,7,9,10-tetrahydro-4H-pyrimido[1,2-d][1,4]oxazepine-2-carboxylate. Intermediate 160 (67.5 mmol) was dissolved in tetrahydrofuran (200 ml), cooled to 0-5° C. and treated with methanesulfonyl chloride (23.0 g, 0.20 mol) followed by triethylamine (28.0 ml, 0.20 mol) added drop wise over 1 h. The cooling bath was then removed and the mixture was stirred at 25° C. for 3 h. The solvent was evaporated in vacuo and the residual oil was diluted with ethyl acetate, washed with water and brine, dried over anhydrous magnesium sulfate and concentrated under reduced pressure. The residual oil was dissolved in a mixture of tetrahydrofuran (100 ml) and anhydrous ethanol (300 ml), treated with anhydrous potassium carbonate (25 g) and stirred at 25° C. for 7 days. The mixture was concentrated under reduced pressure and the residue was diluted with cold water (100 ml) and acidified to pH 4 with concentrated hydrochloric acid. The mixture was extracted with ethyl acetate and the organic phase was extracted three times with 1 N sodium carbonate. The combined basic extracts were cooled and acidified with concentrated hydrochloric acid. This aqueous phase was saturated with sodium chloride and extracted several times with dichloromethane. The combined organic extracts were washed with brine, dried over anhydrous magnesium sulfate and concentrated under reduced pressure to give 8.61 g (50% yield) of the title material as white crystals: mp 189-190° C. (ethyl acetate). $^1$HNMR 400 MHz (CDCl$_3$) δ (ppm): 1.47 (3H, t, J=7.1 Hz, CH$_3$), 3.23 (2H, m, CH$_2$), 3.85-3.93 (4H, m, 2×CH$_2$), 4.53 (2H, q, J=7.1 Hz, OCH$_2$), 4.53 (2H, m, CH$_2$), 10.72 (1H, s, OH). Anal. Calcd for C$_{11}$H$_{14}$N$_2$O$_5$: C 51.97, H 5.55, N 11.02; Found: C 51.76, H 5.29, N 10.86.

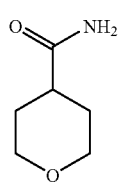

Intermediate 162

Tetrahydro-2H-pyran-4-carboxamide: A mixture of methyl tetrahydro-2H-pyran-4-carboxylate (7.0 g, 48.6 mmol) and concentrated ammonia (20 ml) was stirred at 22° C. for 18 h. The excess ammonia was then removed under reduced pressure and the residue was crystallized from ethanol to give 4.94 g (78% yield) of the title amide as white crystals: mp 179-181° C. $^1$HNMR 400 MHz (CDCl$_3$) δ (ppm): 1.81 (4H, m, 2×CH$_2$), 2.42 (1H, m, CH), 3.44 (2H, m, OCH$_2$), 4.04 (2H, m, OCH$_2$), 5.55 and 5.8 (2×1H, broad, NH$_2$).

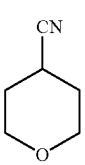

Intermediate 163

Tetrahydro-2H-pyran-4-carbonitrile: A suspension of tetrahydro-2H-pyran-4-carboxamide (4.90 g, 37.9 mmol) in benzene (10 ml) was treated with thionyl chloride (5 ml) and the resulting mixture was stirred at reflux for 4 hours. The cooled mixture was poured onto ice and basified with 50% potassium hydroxide. The aqueous fraction was saturated with salt and extracted with ethyl acetate. The organic fraction was then dried over anhydrous magnesium sulfate and concentrated. Distillation under reduced pressure gave 3.80 g (90% yield) of the title nitrile as a clear oil: bp 80-90° C./15 torr (bulb to bulb distillation, air bath temperature). $^1$HNMR 400 MHz (CDCl$_3$) δ (ppm): 1.91 (4H, m, 2×CH$_2$), 2.89 (1H, m, CH), 3.62 (2H, m, OCH$_2$), 3.92 (2H, m, OCH$_2$).

Intermediate 164

4-((2-Chloroethoxy)methyl)tetrahydro-2H-pyran-4-carbonitrile: A solution of tetrahydro-2H-pyran-4-carbonitrile (3.80 g, 34.2 mmol) in tetrahydrofuran (10 ml) was added dropwise over 5 min to a cold (−78° C.) solution of lithium diisopropylamide (37.5 mmol) in tetrahydrofuran (50 ml). After 30 min, a solution of 2-chloroethyl chloromethyl ether (5.00 g, 38.7 mmol) in tetrahydrofuran (10 ml) was added dropwise over 5 min and the mixture stirred for 30 min. The cooling bath was then removed and the solution was allowed to warm up to 25° C. then stirred for 1.5 h. The reaction mixture was quenched with saturated ammonium chloride and extracted with ethyl acetate. The organic fraction was dried over anhydrous magnesium sulfate and concentrated. Filtration of the residue on silica gel (elution toluene-ethyl acetate 8:2) followed by distillation in vacuo gave 6.33 g (91% yield) of the title nitrile as a clear oil: bp 90-100° C./0.2 torr (bulb to bulb distillation, air bath temperature). $^1$HNMR 400 MHz (CDCl$_3$) δ (ppm): 1.74 (2H, m, CH$_2$), 1.92 (2H, m, CH$_2$), 3.58 (2H, s, CH$_2$), 3.67 (2H, t, J=5.6 Hz, CH$_2$), 3.74 (2H, dt, J=2.3 Hz and J=12.4 Hz, CH$_2$), 3.83 (2H, t, J=5.6 Hz, CH$_2$), 4.0 (2H, m, OCH$_2$).

Intermediate 165

4-((2-Chloroethoxy)methyl)-N-hydroxytetrahydro-2H-pyran-4-carboximidamide: Reaction of 4-((2-chloroethoxy)methyl)tetrahydro-2H-pyran-4-carbonitrile (10.78 g, 52.9 mmol) with hydroxylamine gave 10.59 g (84% yield) of the title material as a white solid. $^1$HNMR 400 MHz (CDCl$_3$) δ

(ppm): 1.60 (2H, m, CH$_2$), 2.04 (2H, m, CH$_2$), 3.52 (2H, s, CH$_2$), 3.55-3.85 (8H, m, 4×CH$_2$), 5.01 (2H, broad s). MS (ESI$^+$) m/e 237 [M+H$^+$].

Intermediate 166

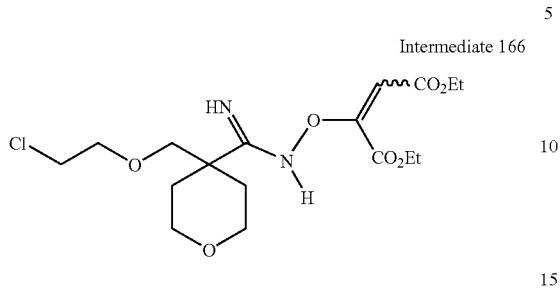

Diethyl 2-(4-((2-chloroethoxy)methyl)tetrahydro-2H-pyran-4-carboximidamidooxy)but-2-enedioate. Reaction of 4-((2-chloroethoxy)methyl)-N-hydroxytetrahydro-2H-pyran-4-carboximidamide (10.50 g, 44.36 mmol) with diethyl acetylenedicarboxylate gave 15.25 g (84% yield) of title material as light yellow oil after chromatography. $^1$HNMR 400 MHz (CDCl$_3$) δ (ppm): (mixture of E/Z isomers ratio~3:2) 1.25-1.4 (6H, quartet of triplets), 1.6 (2H, m), 2.05 (2H, m), 3.52 (1H, s), 3.54 (1H, s), 3.65-3.85 (8H, m), 4.16-4.23 (2H, m), 4.28-4.41 (2H, m), 5.33 (1H, broad s), 5.59 (1H, broad s), 5.64 (1H, s), 5.78 (1H, s). MS (ESI$^+$) m/e 407 [M+H$^+$].

Intermediate 167

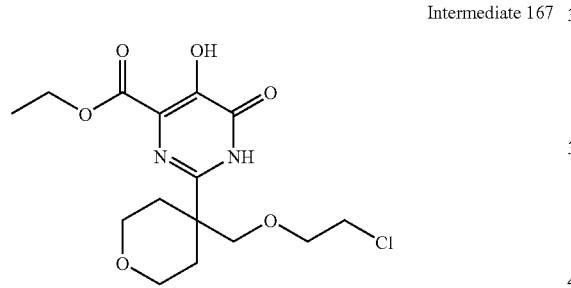

Ethyl 2-(4-((2-chloroethoxy)methyl)tetrahydro-2H-pyran-4-yl)-5-hydroxy-6-oxo-1,6-dihydropyrimidine-4-carboxylate. Heating of intermediate 166 (15.25 g, 37.48 mmol) as described in the preparation of intermediate 160 gave the title compound as a syrup. MS (ESI$^+$) m/e 407 [M+H$^+$].

Intermediate 168

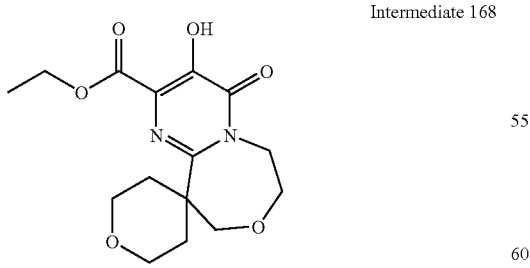

Ethyl 3'-hydroxy-4'-oxo-2,3,4',5,6,6',7',9'-octahydrospiro[pyran-4,10'-pyrimido[1,2-d][1,4]oxazepine]-2'-carboxylate. Cyclization of the crude intermediate 167 (37.48 mmol) gave the title compound as a syrup. MS (ESI$^+$) m/e 325 [M+H$^+$].

Intermediate 169

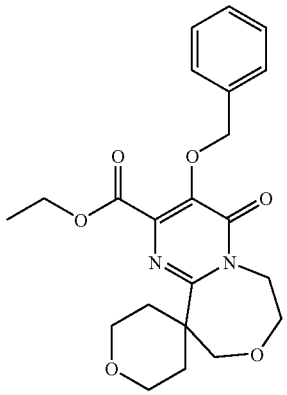

Ethyl 3'-(benzyloxy)-4'-oxo-2,3,4',5,6,6',7',9'-octahydrospiro[pyran-4,10'-pyrimido[1,2-d][1,4]oxazepine]-2'-carboxylate. Benzylation of the crude intermediate 168 (37.48 mmol) followed by chromatography on silica gel gave 5.06 g (33% yield for three steps) of the title compound as a syrup. $^1$HNMR 400 MHz (CDCl$_3$) δ (ppm): 3.25 (3H, t, J=7.0 Hz, CH$_3$), 1.8 (2H, broad m, CH$_2$), 2.35 (2H, broad m, CH$_2$), 3.6-4.0 (10H, broad m, 5×CH$_2$), 4.35 (2H, q, J=7.0 Hz, OCH$_2$), 5.27 (2H, s, OCH$_2$), 7.38 (3H, m, aromatics), 7.50 (2H, m, aromatics). HRMS (ESI$^+$) calculated for C$_{22}$H$_{27}$N$_2$O$_6$ [M+H$^+$]: 415.1869; found: 415.1882.

Intermediate 170

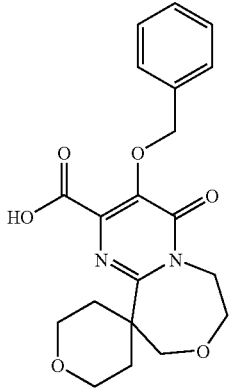

3'-(Benzyloxy)-4'-oxo-2,3,4',5,6,6',7',9'-octahydrospiro[pyran-4,10'-pyrimido[1,2-d][1,4]oxazepine]-2'-carboxylic acid. White crystals (91% yield). $^1$HNMR 400 MHz (CDCl$_3$) δ (ppm): 1.6-2.1 (2H, broad m, CH$_2$), 2.2-2.4 (2H, broad m, CH$_2$), 3.5-4.2 (10H, broad m, 5×CH$_2$), 5.49 (2H, s, OCH$_2$), 7.34-7.41 (3H, m, aromatics), 7.52-7.55 (2H, m, aromatics). HRMS (ESI$^+$) calculated for C$_{20}$H$_{23}$N$_2$O$_6$ [M+H$^+$]: 387.1556; found: 387.1563.

Intermediate 171

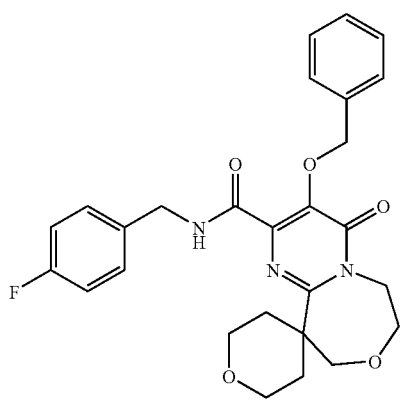

3'-(Benzyloxy)-N-(4-fluorobenzyl)-4'-oxo-2,3,4',5,6,6',7',9'-octahydrospiro[pyran-4,10'-pyrimido[1,2-d][1,4]oxazepine]-2'-carboxamide. A solution of intermediate 170 (0.200 g, 0.518 mmol) and 4-fluorobenzylamine (0.10 g, 0.80 mmol) in acetonitrile (15 ml) was treated at 25° C. with triethylamine (0.20 ml, 1.43 mmol) followed by benzotriazole-1-yl-oxy-tris-(dimethylamino)-phosphoniumhexafluorophosphate (0.26 g, 0.59 mmol) added in one portion. After 3 hours, the reaction mixture was diluted with ethyl acetate, washed successively with 0.1 N hydrochloric acid, saturated sodium bicarbonate and brine, dried over anhydrous magnesium sulfate and concentrated under reduced pressure. Chromatography of the residue on silica gel (elution gradient ethyl acetate 20-50% in toluene) gave after recrystallization from a mixture of ethyl acetate and hexane 0.197 g (77% yield) of the title amide as white crystals; mp 161-162° C. $^1$HNMR 400 MHz (CDCl$_3$) δ (ppm): 1.6-2.1 (2H, broad m, CH$_2$), 2.2-2.4 (2H, broad m, CH$_2$), 3.6-4.1 (10H, broad m, 5×CH$_2$), 4.53 (2H, d, J=6.1 Hz, NCH$_2$), 5.31 (2H, s, OCH$_2$), 7.02 (2H, m, aromatics), 7.23-7.27 (2H, m, aromatics), 7.33-7.38 (3H, m, aromatics), 7.45-7.48 (2H, m, aromatics), 7.64 (1H, broad t, NH). HRMS (ESI$^+$) calculated for C$_{27}$H$_{29}$FN$_3$O$_5$ [M+H$^+$]: 494.2091; found: 494.2122.

Intermediate 172

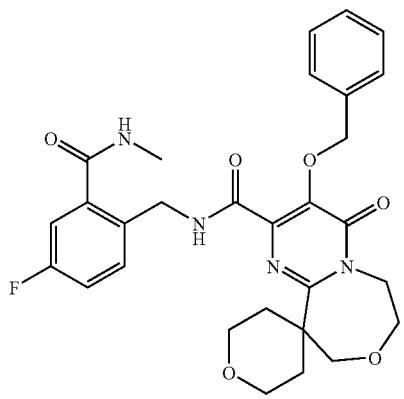

3'-(Benzyloxy)-N-(4-fluoro-2-(methylcarbamoyl)benzyl)-4'-oxo-2,3,4',5,6,6',7',9'-octahydrospiro[pyran-4,10'-pyrimido[1,2-d][1,4]oxazepine]-2'-carboxamide. White solid (100% yield). $^1$HNMR 400 MHz (CDCl$_3$) δ (ppm): 1.7-2.0 (2H, broad m, CH$_2$), 2.2-2.5 (2H, broad m, CH$_2$), 3.00 (3H, d, J=4.8 Hz, NCH$_3$), 3.5-4.0 (10H, broad m, 5×CH$_2$), 4.56 (2H, d, J=6.4 Hz, NCH$_2$), 5.31 (2H, s, OCH$_2$), 6.39 (1H, broad q, NH), 7.09-7.17 (2H, m, aromatics), 7.30-7.35 (3H, m, aromatics), 7.49-7.53 (3H, m, aromatics), 8.66 (1H, broad t, NH). HRMS (ESI$^+$) calculated for C$_{29}$H$_{32}$FN$_4$O$_6$ [M+H$^+$]: 551.2306; found: 551.2308.

Intermediate 173

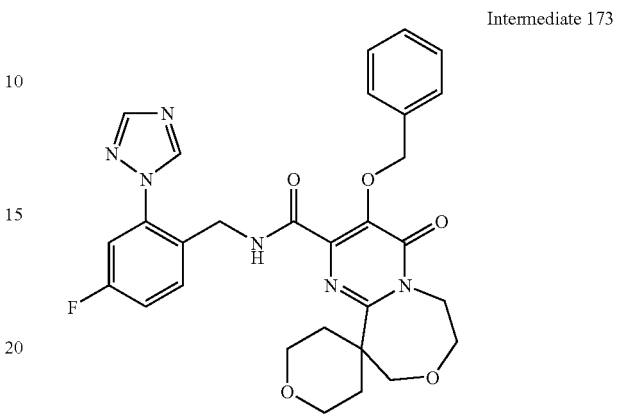

3'-(Benzyloxy)-N-(4-fluoro-2-(1H-1,2,4-triazol-1-yl)benzyl)-4'-oxo-2,3,4',5,6,6',7',9'-octahydrospiro[pyran-4,10'-pyrimido[1,2-d][1,4]oxazepine]-2'-carboxamide. White crystals (86% yield). $^1$HNMR 400 MHz (CDCl$_3$) δ (ppm): 1.6-2.1 (2H, broad m, CH$_2$), 2.2-2.5 (2H, broad m, CH$_2$), 3.6-4.0 (10H, broad m, 5×CH$_2$), 4.44 (2H, d, J=6.5 Hz, NCH$_2$), 5.32 (2H, s, OCH$_2$), 7.09 (1H, dd, J=2.6 Hz and J=8.5 Hz, aromatic), 7.20 (1H, m, aromatic), 7.30-7.33 (3H, m, aromatics), 7.48-7.51 (2H, m, aromatics), 7.78 (1H, dd, J=6.0 Hz and J=8.5 Hz, aromatic), 8.07 (1H, s, CH), 8.42 (1H, s, CH), 8.52 (1H, broad t, NH). HRMS (ESI$^+$) calculated for C$_{29}$H$_{30}$FN$_6$O$_5$ [M+H$^+$]: 561.2262; found: 561.2241.

Intermediate 174

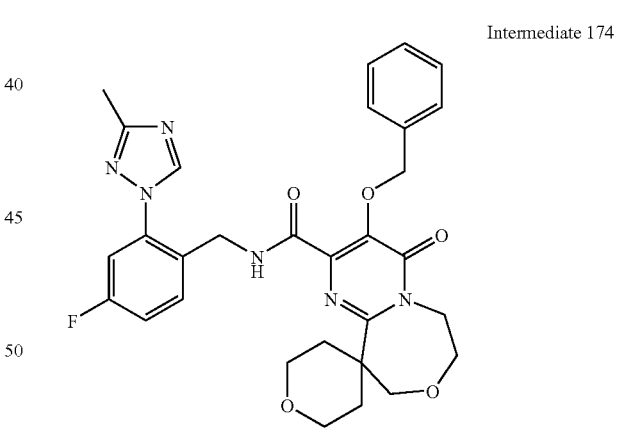

3'-(Benzyloxy)-N-(4-fluoro-2-(3-methyl-1H-1,2,4-triazol-1-yl)benzyl)-4'-oxo-2,3,4',5,6,6',7',9'-octahydrospiro[pyran-4,10'-pyrimido[1,2-d][1,4]oxazepine]-2'-carboxamide. White crystals (82% yield); mp 162° C. $^1$HNMR 400 MHz (CDCl$_3$) δ (ppm): 1.6-2.0 (2H, broad m, CH$_2$), 2.2-2.5 (2H, broad m, CH$_2$), 2.48 (3H, s, CH$_3$), 3.6-4.0 (10H, broad m, 5×CH$_2$), 4.48 (2H, d, J=6.3 Hz, NCH$_2$), 5.32 (2H, s, OCH$_2$), 7.08 (1H, dd, J=2.5 Hz and J=8.6 Hz, aromatic), 7.18 (1H, m, aromatic), 7.25-7.30 (3H, m, aromatics), 7.42-7.45 (2H, m, aromatics), 7.73 (1H, dd, J=6.1 Hz and J=8.6 Hz, aromatic), 8.29 (1H, s, CH), 8.35 (1H, broad t, NH). Anal. Calcd for C$_{30}$H$_{31}$FN$_6$O$_5$: C. 62.70; H, 5.43; N, 14.62; Found: C, 62.61; H, 5.45; N, 14.46.

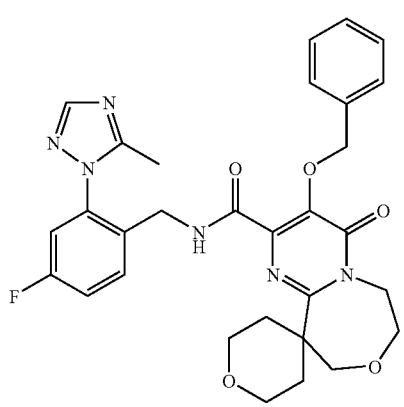

Intermediate 175

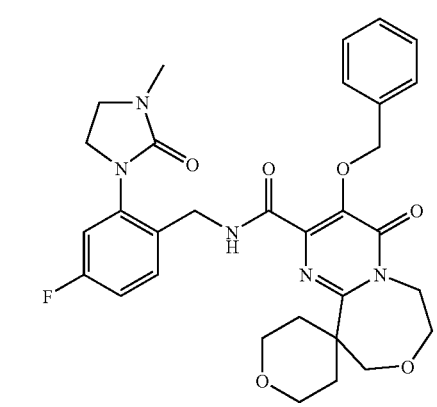

Intermediate 177

3'-(Benzyloxy)-N-(4-fluoro-2-(5-methyl-1H-1,2,4-triazol-1-yl)benzyl)-4'-oxo-2,3,4',5,6,6',7',9'-octahydrospiro[pyran-4,10'-pyrimido[1,2-d][1,4]oxazepine]-2'-carboxamide. White crystals (87% yield). $^1$HNMR 400 MHz (CDCl$_3$) δ (ppm): 1.6-2.0 (2H, broad m, CH$_2$), 2.1-2.5 (2H, broad m, CH$_2$), 2.48 (3H, s, CH$_3$), 3.6-4.0 (10H, broad m, 5×CH$_2$), 4.27 (2H, d, J=6.3 Hz, NCH$_2$), 5.33 (2H, s, OCH$_2$), 7.00 (1H, dd, J=2.8 Hz and J=8.5 Hz, aromatic), 7.22 (1H, m, aromatic), 7.31-7.36 (3H, m, aromatics), 7.48-7.51 (2H, m, aromatics), 7.73 (1H, dd, J=6.0 Hz and J=8.5 Hz, aromatic), 7.93 (1H, s, CH), 8.28 (1H, broad t, NH). HRMS (ESI$^+$) calculated for C$_{30}$H$_{32}$FN$_6$O$_5$ [M+H$^+$]: 575.2418; found: 575.2419.

3'-(Benzyloxy)-N-(4-fluoro-2-(3-methyl-2-oxoimidazolidin-1-yl)benzyl)-4'-oxo-2,3,4',5,6,6',7',9'-octahydrospiro[pyran-4,10'-pyrimido[1,2-d][1,4]oxazepine]-2'-carboxamide. White solid (81% yield). $^1$HNMR 400 MHz (CDCl$_3$) δ (ppm): 1.6-2.1 (2H, broad m, CH$_2$), 2.2-2.6 (2H, broad m, CH$_2$), 2.87 (3H, s, CH$_3$), 3.53 (2H, t, J=7.9 Hz, CH$_2$), 3.6-4.0 (10H, broad m, 5×CH$_2$), 3.79 (2H, t, J=7.9 Hz, CH$_2$), 4.52 (2H, broad d, NCH$_2$), 5.34 (2H, s, OCH$_2$), 6.89 (1H, dd, J=2.5 Hz and J=9.8 Hz, aromatic), 6.94 (1H, m, aromatic), 7.3-7.4 (3H, m, aromatics), 7.5-7.6 (3H, m, aromatics), 8.49 (1H, broad t, NH). HRMS (ESI$^+$) calculated for C$_{31}$H$_{35}$FN$_5$O$_6$ [M+H$^+$]: 592.2571; found: 592.2579.

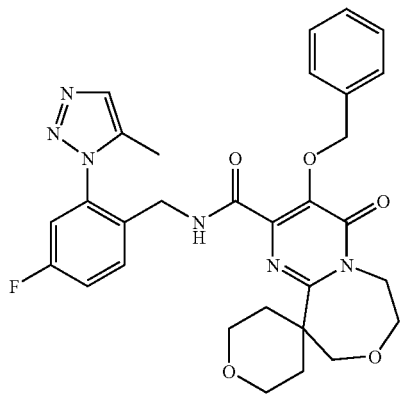

Intermediate 176

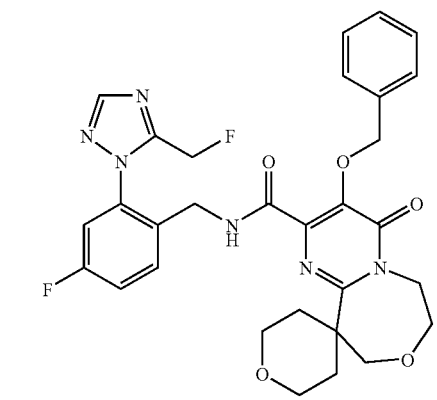

Intermediate 178

3'-(Benzyloxy)-N-(4-fluoro-2-(5-methyl-1H-1,2,3-triazol-1-yl)benzyl)-4'-oxo-2,3,4',5,6,6',7',9'-octahydrospiro[pyran-4,10'-pyrimido[1,2-d][1,4]oxazepine]-2'-carboxamide. White crystals (90% yield). $^1$HNMR 400 MHz (CDCl$_3$) δ (ppm): 1.6-2.1 (2H, broad m, CH$_2$), 2.2-2.6 (2H, broad m, CH$_2$), 2.31 (3H, s, CH$_3$), 3.6-4.0 (10H, broad m, 5×CH$_2$), 4.21 (2H, d, J=6.3 Hz, NCH$_2$), 5.34 (2H, s, OCH$_2$), 7.00 (1H, dd, J=2.5 Hz and J=8.5 Hz, aromatic), 7.26 (1H, m, aromatic), 7.3-7.36 (3H, m, aromatics), 7.53-7.55 (2H, m, aromatics), 7.65 (1H, s, CH), 7.77 (1H, dd, J=6.0 Hz and J=8.5 Hz, aromatic), 8.30 (1H, broad t, NH). HRMS (ESI$^+$) calculated for C$_{30}$H$_{32}$FN$_6$O$_5$ [M+H$^+$]: 575.2418; found: 575.2418.

3'-(Benzyloxy)-N-(4-fluoro-2-(5-(fluoromethyl)-1H-1,2,4-triazol-1-yl)benzyl)-4'-oxo-2,3,4',5,6,6',7',9'-octahydrospiro[pyran-4,10'-pyrimido[1,2-d][1,4]oxazepine]-2'-carboxamide. White crystals (69% yield). $^1$HNMR 400 MHz (CDCl$_3$) δ (ppm): 1.6-2.1 (2H, broad m, CH$_2$), 2.2-2.6 (2H, broad m, CH$_2$), 3.6-4.0 (10H, broad m, 5×CH$_2$), 4.27 (2H, d, J=6.3 Hz, NCH$_2$), 5.32 (2H, s, OCH$_2$), 5.42 (2H, d, J=47.7 Hz, CH$_2$F), 7.15 (1H, dd, J=2.5 Hz and J=8.3 Hz, aromatic), 7.26 (1H, m, aromatic), 7.31-7.36 (3H, m, aromatics), 7.47-7.52 (2H, m, aromatics), 7.73 (1H, dd, J=6.0 Hz and J=8.7 Hz, aromatic), 8.07 (1H, s, CH), 8.19 (1H, broad t, NH). MS (ESI$^+$) m/e 593 [M+H$^+$].

Intermediate 179

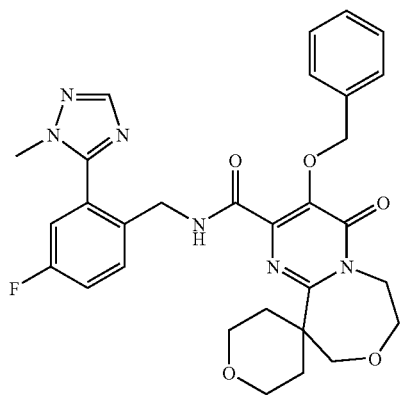

3'-(Benzyloxy)-N-(4-fluoro-2-(1-methyl-1H-1,2,4-triazol-5-yl)benzyl)-4'-oxo-2,3,4',5,6,6',7',9'-octahydrospiro[pyran-4,10'-pyrimido[1,2-d][1,4]oxazepine]-2'-carboxamide. White solid (50% yield). $^1$HNMR 400 MHz (CDCl$_3$) δ (ppm): 1.6-2.1 (2H, broad m, CH$_2$), 2.2-2.7 (2H, broad m, CH$_2$), 3.5-4.0 (10H, broad m, 5×CH$_2$), 3.95 (3H, s, CH$_3$), 4.43 (2H, d, J=6.6 Hz, NCH$_2$), 5.32 (2H, s, OCH$_2$), 7.11 (1H, dd, J=2.5 Hz and J=8.6 Hz, aromatic), 7.22 (1H, m, aromatic), 7.28-7.34 (3H, m, aromatics), 7.50-7.54 (2H, m, aromatics), 7.76 (1H, dd, J=5.8 Hz and J=8.6 Hz, aromatic), 7.92 (1H, s, CH), 8.88 (1H, broad t, NH). HRMS (ESI$^+$) calculated for C$_{30}$H$_{32}$FN$_6$O$_5$ [M+H$^+$]: 575.2418; found: 575.2419.

Intermediate 180

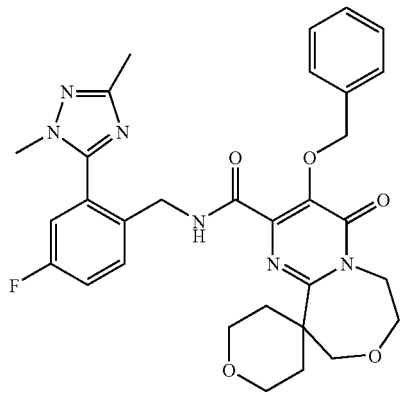

3'-(Benzyloxy)-N-(2-(1,3-dimethyl-1H-1,2,4-triazol-5-yl)-4-fluorobenzyl)-4'-oxo-2,3,4',5,6,6',7',9'-octahydrospiro[pyran-4,10'-pyrimido[1,2-d][1,4]oxazepine]-2'-carboxamide. White solid (60% yield). $^1$HNMR 400 MHz (CDCl$_3$) δ (ppm): 1.6-2.1 (2H, broad m, CH$_2$), 2.1-2.5 (2H, broad m, CH$_2$), 2.41 (3H, s, CH$_3$), 3.5-4.0 (10H, broad m, 5×CH$_2$), 3.85 (3H, s, CH$_3$), 4.46 (2H, d, J=6.0 Hz, NCH$_2$), 5.33 (2H, s, OCH$_2$), 7.09 (1H, dd, J=5.5 Hz and J=8.6 Hz, aromatic), 7.20 (1H, m, aromatic), 7.27-7.31 (3H, m, aromatics), 7.44-7.48 (2H, m, aromatics), 7.71 (1H, dd, J=2.5 Hz and J=8.6 Hz, aromatic), 8.62 (1H, broad t, NH). HRMS (ESI$^+$) calculated for C$_{31}$H$_{34}$FN$_6$O$_5$ [M+H$^+$]: 589.2575; found: 589.2551.

Intermediate 181

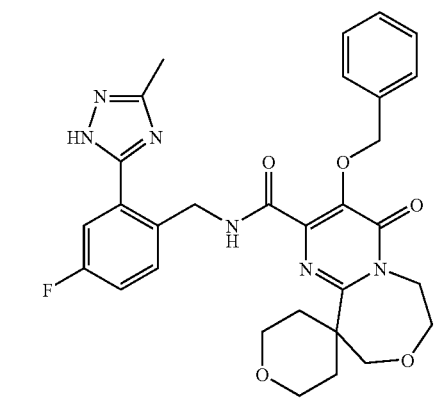

3'-(Benzyloxy)-N-(4-fluoro-2-(3-methyl-1H-1,2,4-triazol-5-yl)benzyl)-4'-oxo-2,3,4',5,6,6',7',9'-octahydrospiro[pyran-4,10'-pyrimido[1,2-d][1,4]oxazepine]-2'-carboxamide. White solid (46% yield). $^1$HNMR 400 MHz (CDCl$_3$) δ (ppm): 1.7-1.9 (2H, broad m, CH$_2$), 2.3-2.6 (2H, broad m, CH$_2$), 2.51 (3H, s, CH$_3$), 3.6-4.0 (10H, broad m, 5×CH$_2$), 4.67 (2H, d, J=6.6 Hz, NCH$_2$), 5.25 (2H, s, OCH$_2$), 7.07 (1H, m, aromatic), 7.3-7.35 (3H, m, aromatics), 7.48-7.55 (2H, m, aromatics), 7.58 (1H, dd, J=5.8 Hz and J=8.6 Hz, aromatic), 7.76 (1H, dd, J=2.8 Hz and J=9.8 Hz, aromatic), 9.30 (1H, broad t, NH). HRMS (ESI$^+$) calculated for C$_{30}$H$_{32}$FN$_6$O$_5$ [M+H$^+$]: 575.2418; found: 575.2390.

Intermediate 182

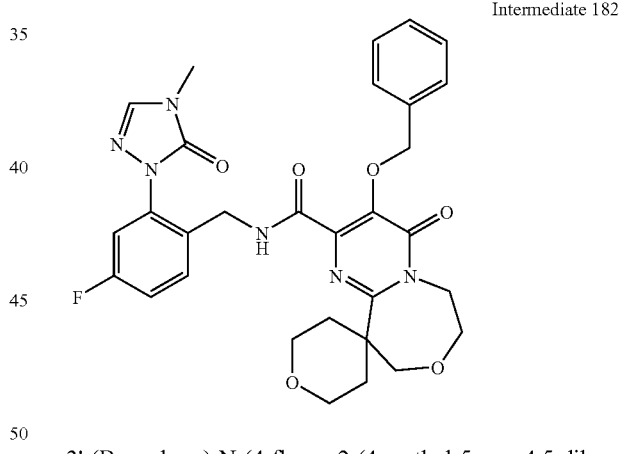

3'-(Benzyloxy)-N-(4-fluoro-2-(4-methyl-5-oxo-4,5-dihydro-1H-1,2,4-triazol-1-yl)benzyl)-4'-oxo-2,3,4',5,6,6',7',9'-octahydrospiro[pyran-4,10'-pyrimido[1,2-d][1,4]oxazepine]-2'-carboxamide: To a solution of 3'-(benzyloxy)-4'-oxo-2,3,4',5,6,6',7',9'-octahydrospiro[pyran-4,10'-pyrimido[1,2-d][1,4]oxazepine]-2'-carboxylic acid (0.095 g, 0.246 mmol) in CH$_3$CN (15 mL) was added 1-(2-(aminomethyl)-5-fluorophenyl)-4-methyl-1H-1,2,4-triazol-5(4H)-one (0.070 g, 0.271 mmol), diisopropylethylamine (0.171 mL, 0.984 mmol) and O-(7-azabenzotriazole-1yl)-N,N,N',N'-tetramethyluronium (0.103 g, 0.271 mmol). The reaction mixture was stirred at 23° C. for 18 hours. HCl (1N, 50 mL) was added and the organic material was extracted with EtOAc (3×50 mL). The combined organic phases were washed with H$_2$O (50 mL), brine (50 mL), dried over MgSO$_4$ and concentrated in vacuo. The crude material was purified on Silica gel column (Biotage™), eluted with EtOAc:Hex (1:1) to EtOAc 100% to afford the title compound as a white solid (0.130 g, 77%): $^1$H NMR (400 MHz, CDCl$_3$) δ 8.54 (1 H, brs), 7.67 (1H, dd, J=8.7, 6.2 Hz), 7.52 (2H, m), 7.45 (1H, s), 7.27-7.36 (3H, m), 7.22 (1H, dd, J=9.3, 2.5 Hz), 7.08 (1H, td, J=8.2, 2.5 Hz), 5.31 (2H, s), 4.54 (2 H, d, J=6.3 Hz), 4.1-3.6 (10H, m), 3.36 (3H, s), 2.4-2.2 (1H, brm), 2.1-1.6 (2H, brs). LCMS ($^+$ESI, M+H$^+$) m/z 591.

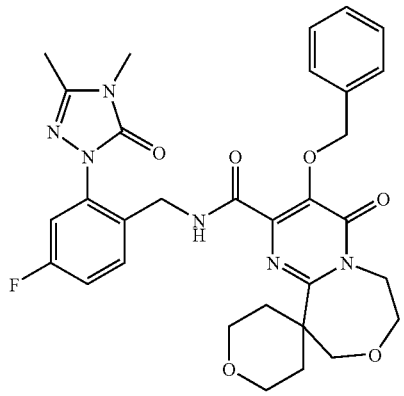

Intermediate 183

3'-(Benzyloxy)-N-(2-(3,4-dimethyl-5-oxo-4,5-dihydro-1H-1,2,4-triazol-1-yl)-4-fluorobenzyl)-4'-oxo-2,3,4',5,6,6',7',9'-octahydrospiro[pyran-4,10'-pyrimido[1,2-d][1,4]oxazepine]-2'-carboxamide: $^1$H NMR (400 MHz, CDCl$_3$) δ 8.59 (1H, brs), 7.66 (1H, dd, J=8.6, 6.3 Hz), 7.49 (2H, m), 7.31 (3H, m), 7.20 (1H, dd, J=9.3, 2.5 Hz), 7.06 (1H, td, J=8.3, 2.5 Hz), 5.31 (2H, s), 4.55 (2H, d, J=6.3 Hz), 4.0-3.6 (10 H, brm), 3.29 (3H, s), 2.4-2.3 (2H, brm), 2.28 (3H, s), 2.1-1.6 (2H, brm): LCMS ($^+$ESI, M+H$^+$) m/z 605.

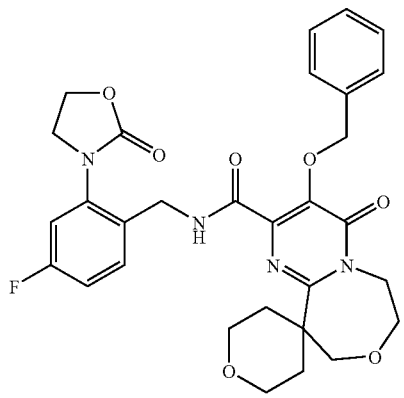

Intermediate 184

3'-(Benzyloxy)-N-(4-fluoro-2-(2-oxooxazolidin-3-yl)benzyl)-4'-oxo-2,3,4',5,6,6',7',9'-octahydrospiro[pyran-4,10'-pyrimido[1,2-d][1,4]oxazepine]-2'-carboxamide: $^1$H NMR (400 MHz, CDCl$_3$) δ 8.23 (1H, brs), 7.50-7.58 (2H, m), 7.31-7.41 (4H, m), 6.95-7.06 (2H, m), 5.34 (2H, s), 4.55 (4H, m), 4.05 (2H, t, J=7.8 Hz), 3.9-3.6 (10H, brm), 2.4-2.3 (2H, brs), 2.1-1.6 (2H, brm); LCMS ($^+$ESI, M+H$^+$) m/z 579.

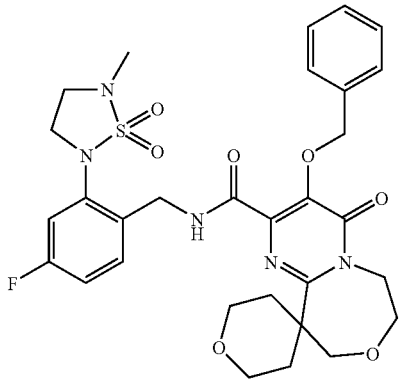

Intermediate 185

3'-(Benzyloxy)-N-(4-fluoro-2-(1,1-dioxo-5-methyl-1,2,5-thiazolidin-2-yl)benzyl)-4'-oxo-2,3,4',5,6,6',7',9'-octahydrospiro[pyran-4,10'-pyrimido[1,2-d][1,4]oxazepine]-2'-carboxamide: $^1$H NMR (400 MHz, CDCl$_3$) δ 8.02 (1H, t, J=6.4 Hz), 7.56 (1H, dd, J=8.7, 6.2 Hz), 7.45 (2H, dd, J=7.5, 1.9 Hz), 7.21-7.35 (3 H, m), 7.11 (1H, dd, J=9.3, 2.5 Hz), 7.01 (1H, td, J=8.2, 2.5 Hz), 5.25 (2H, s), 4.65 (2H, d, J=6.6 Hz), 3.9-3.6 (12H, brm), 3.43 (2H, t, J=6.4 Hz), 2.77 (3H, s), 2.4-2.15 (2H, brs), 1.95-1.5 (2H, brm); LCMS ($^+$ESI, M+H$^+$) m/z 628.

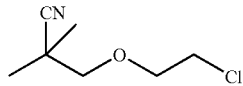

Intermediate 186

3-(2-Chloroethoxy)-2,2-dimethylpropanenitrile: To a solution of LDA (0.14 mol) in 100 mL THF at –30° C. under N$_2$ was added isobutyronitrile (9.7 g, 0.14 mol) in 40 mL THF, dropwise over 20 min. After 20 min, a solution of 1-chloro-2-(chloromethoxy)ethane (18.1 g, 0.14 mol) in 50 mL THF was added dropwise and the temperature was allowed to gradually rise to room temperature and the reaction mixture stirred for 5 h. This was treated with 200 mL of water and Et$_2$O and the layers separated. The aqueous layer was extracted further with Et$_2$O. The combined organic extracts were washed with brine, dried over Na$_2$SO$_4$, filtered and concentrated to leave 23 g of crude product as a yellow oil. This was purified by silica gel chromatography using 9:1 hexanes/CH$_2$Cl$_2$ to 4:1 hexanes/CH$_2$Cl$_2$ as eluents. This yielded 7.4 g (32%) of the title compound as an oil. $^1$H NMR (300 MHz, CDCl$_3$) δ: 1.33 (s, 6H), 3.43 (s, 2H), 3.61 (t, J=5.7 Hz, 2H), 3.77 (t, J=5.9 Hz, 2H). LC/MS (M+H): 162.

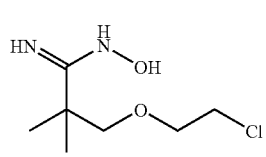

Intermediate 187

3-(2-Chloroethoxy)-N-Hydroxy-2,2-dimethylpropanamidine: 3-(2-Chloroethoxy)-2,2-dimethylpropanenitrile (6.1 g, 37.7 mmol) was placed together with 50% aqueous hydroxylamine (3.1 g, 37.7 mmol) in 60 mL EtOH and warmed at 75-80° C. with stirring for 18 h. The solution was concentrated and then azeotroped with EtOH to provide (9.4 g, ~80% pure) of the title compound as a gum. ¹H NMR (300 MHz, CDCl₃) δ: 1.17 (s, 6H), 3.40 (s, 2H), 3.58-3.73 (m, 4H), 5.16 (s, 2H). LC/MS (M+H): 195.

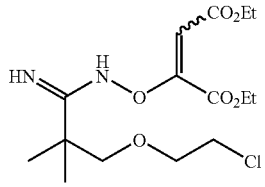

Intermediate 188

Diethyl 2-(3-(2-chloroethoxy)-2,2-dimethylpropanimidamidooxy)but-2-enedioate. A solution of 3-(2-chloroethoxy)-N-hydroxy-2,2-dimethylpropanamidine (7.4 g, 37.7 mmol) in 70 mL EtOH and 10 mL H₂O was treated with diethyl acetylenedicarboxylate (6.4 g, 37.7 mmol). This was stirred for 1 h at room temperature and concentrated. The residue was dissolved in EtOAc and washed with water and then brine. The EtOAc solution was dried over Na₂SO₄, filtered and concentrated to leave 14 g of a yellow oil. This was purified by chromatography on silica gel using 3:1 hexanes/EtOAc to give 5 g (36% yield) of the title compound as a clear oil. ¹HNMR (300 MHz, CDCl₃) δ: 1.15 (s, 6H), 1.16-1.39 (m, 6H), 3.41 (s, 2H), 3.56-3.77 (m, 4H), 4.05-4.20 (m, 2H), 4.21-4.37 (m, 2H), 5.30-5.45 (m, 1H), 5.62 (s, 0.5H), 5.64-5.75 (m, 1H), 5.77 (s, 0.5H). LC/MS (M+H): 365.

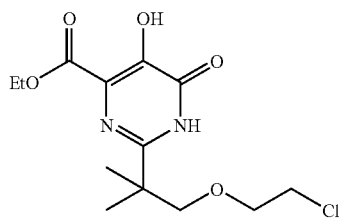

Intermediate 189

Ethyl 2-(1-(2-chloroethoxy)-2-methylpropan-2-yl)-5-hydroxy-6-oxo-1,6-dihydropyrimidine-4-carboxylate. Intermediate 188 was dissolved in 150 mL 1,2,4-trimethylbenzene and stirred at 155-160° C. for 2.5 hrs under N₂. The solvent was evaporated at reduced pressure and the residue was dissolved in EtOAc and extracted 2× with dil NaHCO₃. The aqueous extracts were acidified with HCl and extracted with CH₂Cl₂. The organic layer was dried (MgSO₄), filtered and concentrated to provide the title compound (1.9 g, 43%) as a white solid. ¹H NMR (300 MHz, CDCl₃) δ: 1.31 (s, 6H), 1.41 (t, J=7.1 Hz, 3H), 3.54 (s, 2H), 3.63-3.72 (m, 2H), 3.75-3.83 (m, 2H), 4.42 (q, J=7.3 Hz, 2H). LC/MS (M+H): 319.

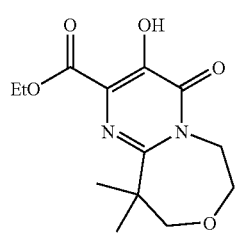

Intermediate 190

Ethyl 3-hydroxy-10,10-dimethyl-4-oxo-6,7,9,10-tetrahydro-4H-pyrimido[1,2-d][1,4]oxazepine-2-carboxylate. Intermediate 189 (1.75 g, 5.49 mmol) was dissolved in 30 mL DMF under N₂ and treated with K₂CO₃ (2.27 g, 16.5 mmol). This was warmed to 70-80° C. with stirring for 16 h. The DMF was evaporated at reduced pressure and the residue was dissolved in water and washed with Et₂O. The aqueous layer was acidified with dilute HCl and extracted with CH₂Cl₂. The organic extract was dried (MgSO₄), filtered and concentrated to provide a solid. Trituration with 1:1 Et₂O/hexanes gave the title compound (1.2 g, 77% yield) as a white solid. ¹H NMR (300 MHz, CDCl₃) δ: 1.35-1.45 (m, 9H), 3.58 (s, 2H), 3.60-4.10 (m, 1H), 4.41 (q, J=6.95 Hz, 2H), 4.30-4.82 (m, 2H), 10.42 (s, 1H). LC/MS (M+H): 283.

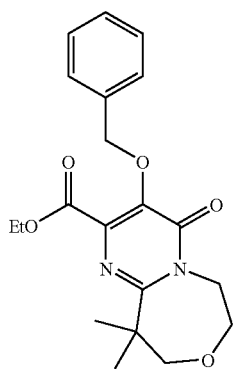

Intermediate 191

Ethyl 3-(benzyloxy)-10,10-dimethyl-4-oxo-6,7,9,10-tetrahydro-4H-pyrimido[1,2-d][1,4]oxazepine-2-carboxylate. Intermediate 190 (790 mg, 2.8 mmol) and benzyl bromide (580 mg, 3.4 mmol) were placed together in 10 mL DMF under N₂ and treated with K₂CO₃ (512 mg, 4 mmol). After warming for 2.5 h at 60-70° C., the DMF was removed under reduced pressure. The residue was dissolved in CH₂Cl₂ and washed with H₂O. The CH₂Cl₂ solution was dried over MgSO₄, filtered and concentrated to give the title compound (940 mg, 90%) as a solid. ¹H NMR (300 MHz, CDCl₃) δ: 1.27 (t, J=7.3 Hz, 3H), 1.54 (s, 6H), 3.59 (s, 2H), 3.65-3.95 (m, 2H), 4.30 (q, J=7.3 Hz, 2H), 4.40-4.80 (m, 2H), 5.19 (s, 2H), 7.29-7.34 (m, 3H), 7.39-7.49 (m, 2H). LC/MS (M+H): 373.

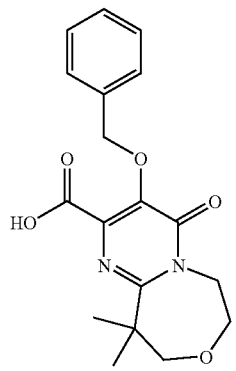

Intermediate 192

3-(Benzyloxy)-10,10-dimethyl-4-oxo-6,7,9,10-tetrahydro-4H-pyrimido[1,2-d][1,4]oxazepine-2-carboxylic acid. Intermediate 191 (920 mg, 2.5 mmol) was dissolved in 5 mL of THF and to it was added with stirring LiOH (120 mg, 5 mmol) and 5 mL water. After 30 min, the THF was evaporated and the aqueous layer was acidified with dil HCl. This was extracted with CH$_2$Cl$_2$, dried (MgSO$_4$), filtered and concentrated. Trituration from Et$_2$O gave the title compound (790 mg, 91%) as a solid: $^1$H NMR (300 MHz, CDCl$_3$) δ: 1.40 (s, 6H), 3.60 (s, 2H), 3.65-3.95 (m, 2H), 4.10-4.90 (m, 2H), 5.41 (s, 2H), 7.25-7.42 (m, 3H), 7.45-7.58 (m, 2H). LC/MS (M+H): 345.

Intermediate 193

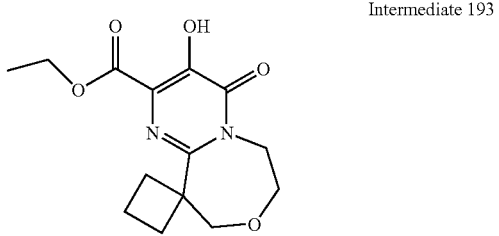

Ethyl 3'-hydroxy-4'-oxo-4',6',7',9'-tetrahydrospiro[cyclobutane-1,10'-pyrimido[1,2-d][1,4]oxazepine]-2'-carboxylate. $^1$H NMR (300 MHz, CDCl$_3$) δ: 1.42 (t, J=7.0 Hz, 3H), 1.78-2.27 (m, 4H), 2.57-2.75 (m, 2H), 3.59-3.79 (m, 2H), 3.82 (s, 2H), 4.27-4.36 (m, 2H), 4.43 (q, J=7.0 Hz, 2H), 10.50 (s, 1H). LC/MS (M+H) m/z 295.

Intermediate 194

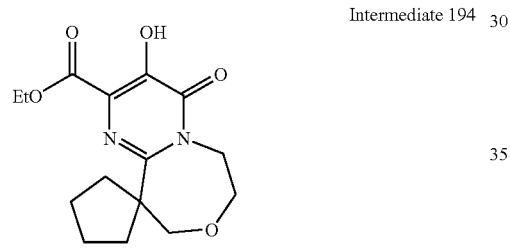

Ethyl 3'-hydroxy-4'-oxo-4',6',7',9'-tetrahydrospiro[cyclopentane-1,10'-pyrimido[1,2-d][1,4]oxazepine]-2'-carboxylate. $^1$H NMR (300 MHz, CDCl$_3$) δ: 1.41 (t, J=7.0 Hz, 3H), 1.59-1.83 (m, 8H), 2.12-2.29 (m, 2H), 3.55 (s, 2H), 3.61-3.69 (m, 2H), 3.72-3.80 (m, 2H), 4.41 (q, J=7.0 Hz, 2H), 10.67 (s, 1H). LC/MS (M+H) m/z 309.

Example 1

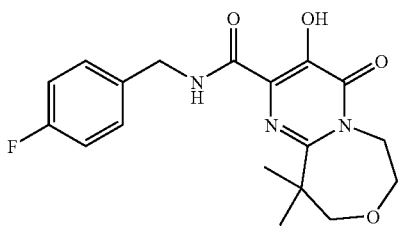

N-((4-Fluorophenyl)methyl)-3-hydroxy-10,10-dimethyl-4-oxo-6,7,9,10-tetrahydro-4H-pyrimido[1,2-d][1,4]oxazepine-2-carboxamide. Intermediate 190 (30 mg, 0.3 mmol) was combined with p-fluorobenzylamine (37 mg, 0.3 mmol) and triethylamine (101 mg, 1 mmol) in 1 mL DMF in a sealed flask with stirring and was warmed in an oil bath at 100-110° C. for 3 hrs. The DMF was removed at reduced pressure and the resulting residue was purified by reverse phase (C18) column chromatography eluted with 25% CH$_3$CN/H$_2$O+ 0.1% TFA. The fractions containing the product were concentrated and extracted with CH$_2$Cl$_2$. Evaporation of the solvent and trituration with hexanes gave the title compound as a white solid (Yield-25%). $^1$H NMR (300 MHz, CDCl$_3$) δ: 1.35 (s, 6H), 3.56 (s, 2H), 3.60-3.91 (m, 2H), 4.40-4.85 (m, 2H), 4.56 (d, J=6.2 Hz, 2H), 6.90-7.14 (m, 2H), 7.13-7.41 (m, 2H), 7.70-7.83 (m, 1H), 11.86 (s, 1H). HRMS (M+H) calcd. for C$_{18}$H$_{21}$FN$_3$O$_4$: 362.1516; found: 362.1509.

The following examples are prepared according to an analogous procedure for example 1.

Example 2

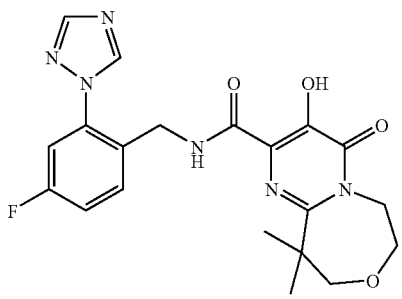

N-((4-Fluoro-2-(1H-1,2,4-triazol-1-yl)phenyl)methyl)-3-hydroxy-10,10-dimethyl-4-oxo-6,7,9,10-tetrahydro-4H-pyrimido[1,2-d][1,4]oxazepine-2-carboxamide. Yield: 48%, white crystals. $^1$H NMR (300 MHz, CDCl$_3$) δ: 1.42 (s, 6H), 3.57 (s, 2H), 3.62-3.94 (m, 2H), 4.10-4.70 (m, 2H), 4.42 (d, J=7.0 hz, 2H), 7.02-7.23 (m, 2H), 7.69 (dd, J=8.6, 6.0 Hz, 1H), 8.10 (s, 1H), 8.46 (s, 1H), 8.80-8.87 (m, 1H), 11.90 (s, 1H). HRMS (M+H) calcd. for C$_{20}$H$_{22}$FN$_6$O$_4$: 429.1687; found: 429.1668.

Example 3

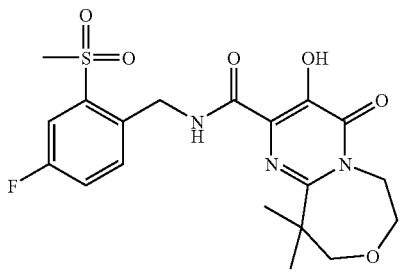

N-((4-Fluoro-2-(methylsulfonyl)phenyl)methyl)-3-hydroxy-10,10-dimethyl-4-oxo-6,7,9,10-tetrahydro-4H-pyrimido[1,2-d][1,4]oxazepine-2-carboxamide. Yield: 23%, white solid. $^1$H NMR (300 MHz, CDCl$_3$) δ: 1.40 (s, 6H), 3.17 (s, 3H), 3.57 (s, 2H), 3.60-4.00 (m, 2H), 4.00-4.50 (m, 2H), 4.82 (d, J=7.0 Hz, 2H), 7.30-7.40 (m, 1H), 7.64-7.82 (m, 2H), 8.49-8.72 (m, 1H), 11.72 (s, 1H). HRMS (M+H) calcd. for C$_{19}$H$_{23}$FN$_3$O$_6$S: 440.1292; found: 440.1297.

Example 4

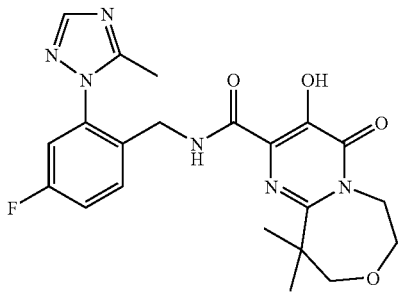

N-((4-Fluoro-2-(5-methyl-1H-1,2,4-triazol-1-yl)phenyl)methyl)-3-hydroxy-10,10-dimethyl-4-oxo-6,7,9,10-tetrahydro-4H-pyrimido[1,2-d][1,4]oxazepine-2-carboxamide. Yield: 60%, white solid. $^1$H NMR (300 MHz, CDCl$_3$) δ: 1.42 (s, 6H), 2.47 (s, 3H), 3.57 (s, 2H), 3.60-3.90 (m, 2H), 4.26 (d, J=7.0 Hz, 2H), 4.30-4.80 (m, 2H), 6.99 (dd, J=8.4, 2.56 Hz, 1H), 7.13-7.32 (m, 1H), 7.67 (dd, J=8.6, 6.0 Hz, 1H), 7.95 (s, 1H), 8.50-8.79 (m, 1H), 11.85 (s, 1H). HRMS (M+H) calcd. for C$_{21}$H$_{24}$FN$_6$O$_4$: 443.1843; found 443.1838.

Example 5

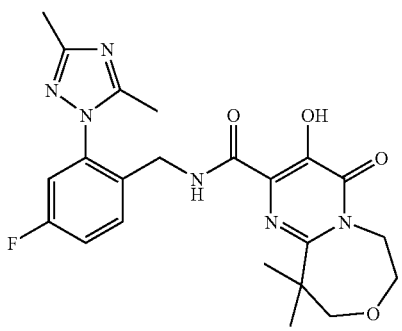

N-((2-(3,5-dimethyl-1H-1,2,4-triazol-1-yl)-4-fluorophenyl)methyl)-3-hydroxy-10,10-dimethyl-4-oxo-6,7,9,10-tetrahydro-4H-pyrimido[1,2-d][1,4]oxazepine-2-carboxamide. Yield: 43%, glassy solid. $^1$H NMR (300 MHz, CDCl$_3$) δ: 1.45 (s, 6H), 2.39 (s, 6H), 3.56 (s, 2H), 3.60-3.85 (m, 2H), 4.30 (d, J=6.6 Hz, 2H), 4.35-4.80 (m, 2H), 6.96 (dd, J=8.4, 2.6 Hz, 1H), 7.11-7.28 (m, 1H), 7.65 (dd, J=8.8, 5.9 Hz, 1H), 8.12-8.45 (m, 1H), 11.96 (s, 1H). HRMS (M+H) calcd. for C$_{22}$H$_{26}$FN$_6$O$_4$: 457.2000; found: 457.2017.

Example 6

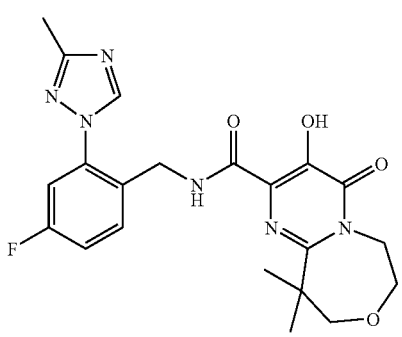

N-((4-fluoro-2-(3-methyl-1H-1,2,4-triazol-1-yl)phenyl)methyl)-3-hydroxy-10,10-dimethyl-4-oxo-6,7,9,10-tetrahydro-4H-pyrimido[1,2-d][1,4]oxazepine-2-carboxamide. Yield: 62%, white crystals. $^1$H NMR (300 MHz, CDCl$_3$) δ: 1.40 (s, 6H), 2.48 (s, 3H), 3.56 (s, 2H), 3.60-3.90 (m, 2H), 4.46 (d, J=6.6 Hz, 2H), 4.50-4.85 (m, 2H), 6.91-7.28 (m, 2H), 7.68 (dd, J=8.6, 6.0 Hz, 1H), 8.30 (s, 1H), 8.50-8.70 (m, 1H), 12.03 (s, 1H). HRMS (M+H) calcd. for C$_{21}$H$_{24}$FN$_6$O$_4$: 443.1843; found: 443.1840.

Example 7

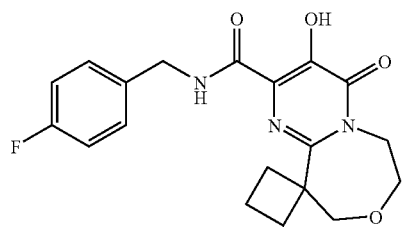

N-((4-fluorophenyl)methyl)-3'-hydroxy-4'-oxo-6',7'-dihydro-4'H-spiro[cyclobutane-1,10'-pyrimido[1,2-d][1,4]oxazepine]-2'-carboxamide. Yield: 70%, white crystals. $^1$H NMR (300 MHz, CDCl$_3$) δ: 1.74-2.69 (m, 6H), 3.55-3.88 (m, 2H), 3.78 (s, 2H), 4.25-4.38 (m, 2H), 4.57 (d, J=6.2 Hz, 2H), 6.91-7.11 (m, 2H), 7.18-7.40 (m, 2H), 7.72-7.96 (m, 1H), 11.99 (s, 1H). HRMS (M+H) calcd. for C$_{19}$H$_{21}$FN$_3$O$_4$: 374.1516; found: 374.1504.

Example 8

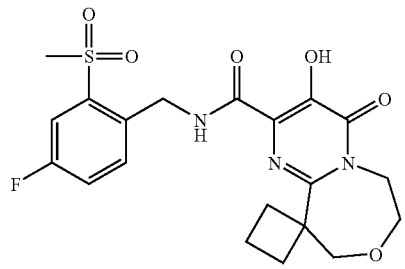

N-((4-fluoro-2-(methylsulfonyl)phenyl)methyl)-3'-hydroxy-4'-oxo-6',7'-dihydro-4'H-spiro[cyclobutane-1,10'-pyrimido[1,2-d][1,4]oxazepine]-2'-carboxamide. Yield: 50%, white crystals. $^1$H NMR (300 MHz, CDCl$_3$) δ: 1.74-2.73 (m, 6H), 3.15 (s, 3H), 3.59-3.71 (m, 2H), 3.77 (s, 2H), 4.22-4.38 (m, 2H), 4.80 (d, J=7.0 Hz, 2H), 7.24-7.48 (m, 1H), 7.59-7.87 (m, 2H), 8.50-8.72 (m, 1H), 11.80 (s, 1H)). HRMS (M+H) calcd. for C$_{20}$H$_{23}$FN$_3$O$_6$S: 452.1292; found: 452.1278.

Example 9

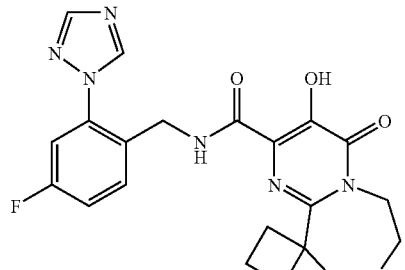

N-((4-fluoro-2-(1H-1,2,4-triazol-1-yl)phenyl)methyl)-3'-hydroxy-4'-oxo-6',7'-dihydro-4'H-spiro[cyclobutane-1,10'-pyrimido[1,2-d][1,4]oxazepine]-2'-carboxamide. Yield: 30%, white crystals. $^1$H NMR (300 MHz, CDCl$_3$) δ: 1.80-2.81 (m, 6H), 3.61-3.79 (m, 2H), 3.80 (s, 2H), 4.23-4.36 (m, 2H), 4.43 (d, J=6.6 Hz, 2H), 7.01-7.33 (m, 2H), 7.69 (dd, J=8.6, 6.0 Hz, 1H), 8.12 (s, 1H), 8.43 (s, 1H), 8.76-9.07 (m, 1H), 11.99 (s, 1H)). HRMS (M+H) calcd. for C$_{21}$H$_{22}$FN$_6$O$_4$: 441.1687; found: 441.1667.

Example 10

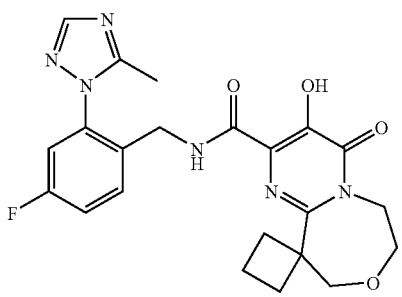

N-((4-fluoro-2-(5-methyl-1H-1,2,4-triazol-1-yl)phenyl)methyl)-3'-hydroxy-4'-oxo-6',7'-dihydro-4'H-spiro[cyclobutane-1,10'-pyrimido[1,2-d][1,4]oxazepine]-2'-carboxamide. Yield: 48%, off-white crystals. $^1$H NMR (300 MHz, CDCl$_3$) δ: 1.81-2.29 (m, 4H), 2.46 (s, 3H), 2.52-2.84 (m, 2H), 3.35-3.75 (m, 2H), 3.80 (s, 2H), 4.02-4.38 (m, 4H), 6.90-7.30 (m, 2H), 7.66 (dd, J=8.8, 5.9 Hz, 1H), 7.93 (s, 1H), 8.60-8.75 (m, 1H), 11.95 (s, 1H)). HRMS (M+H) calcd. for C$_{22}$H$_{24}$FN$_6$O$_4$: 455.1843; found: 455.1854.

Example 11

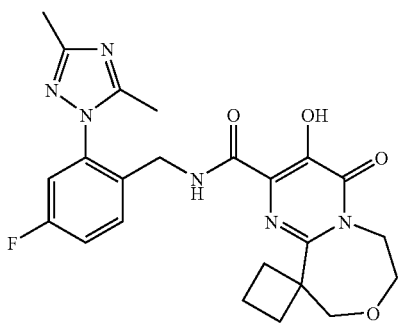

N-((2-(3,5-dimethyl-1H-1,2,4-triazol-1-yl)-4-fluorophenyl)methyl)-3'-hydroxy-4'-oxo-6',7'-dihydro-4'H-spiro[cyclobutane-1,10'-pyrimido[1,2-d][1,4]oxazepine]-2'-carboxamide. Yield: 32%, white crystals. $^1$H NMR (300 MHz, CDCl$_3$) δ: 1.77-2.29 (m, 4H), 2.38 (d, J=4.4 Hz, 6H), 2.53-2.74 (m, 2H), 3.61-3.74 (m, 2H), 3.78 (s, 2H), 4.30 (d, J=6.6 Hz, 4H), 6.88-7.27 (m, 2H), 7.65 (dd, J=8.6, 6.0 Hz, 1H), 8.43-8.65 (m, 1H), 12.08 (s, 1H)). HRMS (M+H) calcd. for C$_{23}$H$_{26}$FN$_6$O$_4$: 469.2000; found: 469.2006.

Example 12

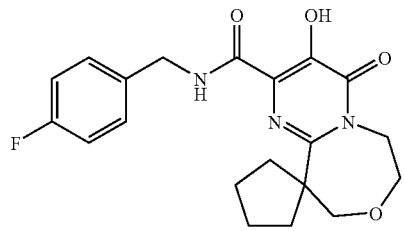

N-((4-fluorophenyl)methyl)-3'-hydroxy-4'-oxo-6',7'-dihydro-4'H-spiro[cyclopentane-1,10'-pyrimido[1,2-d][1,4]oxazepine]-2'-carboxamide. Yield: 23%, off-white crystals. $^1$H NMR (300 MHz, CDCl$_3$) δ: 1.55-2.38 (m, 8H), 3.50 (s, 2H), 3.64-3.88 (m, 2H), 4.56-4.80 (m, 4H), 6.93-7.12 (m, 2H), 7.16-7.41 (m, 2H), 7.67-7.91 (m, 1H), 11.90 (s, 1H). HRMS (M+H) calcd. for C$_{20}$H$_{23}$FN$_3$O$_4$: 388.1673; found: 388.1664.

Example 13

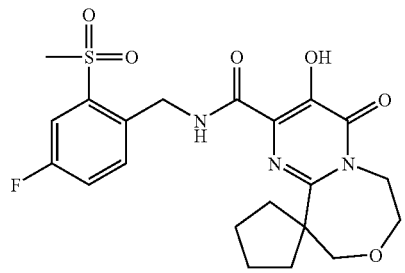

N-((4-fluoro-2-(methylsulfonyl)phenyl)methyl)-3'-hydroxy-4'-oxo-6',7'-dihydro-4'H-spiro[cyclopentane-1,10'-pyrimido[1,2-d][1,4]oxazepine]-2'-carboxamide. Yield: 60%, white crystals. $^1$H NMR (300 MHz, CDCl$_3$) δ: 1.49-2.35 (m, 8H), 3.15 (s, 3H), 3.51 (s, 2H), 3.62-3.84 (m, 2H), 4.40-4.65 (m, 2H), 4.64-4.89 (m, 2H), 7.25-7.39 (m, 1H), 7.60-7.82 (m, 2H), 8.50-8.75 (m, 1H), 11.72 (s, 1H). HRMS (M+H) calcd. for C$_{21}$H$_{25}$FN$_3$O$_6$S: 466.1448; found: 466.1429.

Example 14

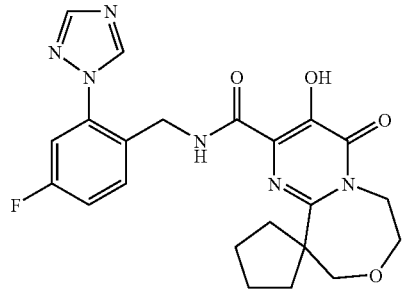

N-((4-fluoro-2-(1H-1,2,4-triazol-1-yl)phenyl)methyl)-3'-hydroxy-4'-oxo-6',7'-dihydro-4'H-spiro[cyclopentane-1,10'-pyrimido[1,2-d][1,4]oxazepine]-2'-carboxamide. Yield: 15%, off-white crystals. $^1$H NMR (300 MHz, CDCl$_3$) δ: 1.44-2.51 (m, 8H), 3.52 (s, 2H), 3.61-3.94 (m, 2H), 4.42 (d, J=7.0 Hz, 2H), 4.40-4.71 (m, 2H), 6.94-7.29 (m, 2H), 7.69 (dd, J=8.6, 6.0 Hz, 1H), 8.12 (s, 1H), 8.43 (s, 1H), 8.81-8.99 (m, 1H), 11.93 (s, 1H). HRMS (M+H) calcd. for C$_{22}$H$_{24}$FN$_6$O$_4$: 455.1843, found 455.1826.

Example 15

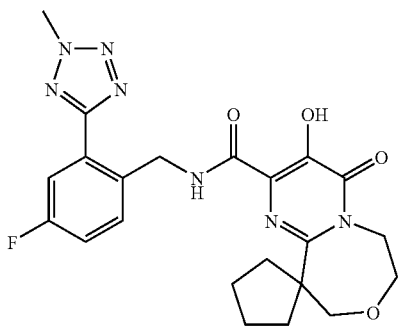

N-((4-fluoro-2-(2-methyl-2H-tetrazol-5-yl)phenyl)methyl)-3'-hydroxy-4'-oxo-6',7'-dihydro-4'H-spiro[cyclopentane-1,10'-pyrimido[1,2-d][1,4]oxazepine]-2'-carboxamide. Yield: 15%, off-white crystals. $^1$H NMR (300 MHz, CDCl$_3$) δ: 1.49-2.43 (m, 8H), 3.48 (s, 3H), 3.59-3.89 (m, 2H), 4.44 (s, 2H), 4.39-4.68 (m, 2H), 4.72 (d, J=7.0 Hz, 2H), 6.97-7.24 (m, 1H), 7.54-7.87 (m, 2H), 8.99-9.29 (m, 1H), 12.04 (s, 1H). HRMS (M+H) calcd. for C$_{22}$H$_{25}$FN$_7$O$_4$: 470.1952; found: 470.1935.

Example 16

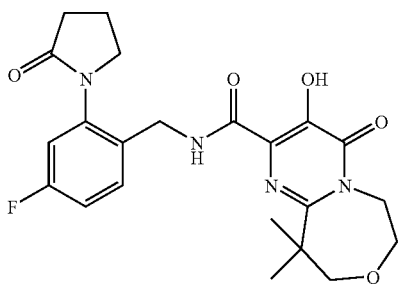

N-((4-fluoro-2-(2-oxo-1-pyrrolidinyl)phenyl)methyl)-3-hydroxy-10,10-dimethyl-4-oxo-6,7,9,10-tetrahydro-4H-pyrimido[1,2-d][1,4]oxazepine-2-carboxamide. Intermediate 192 (86 mg, 0.25 mmol) and O-(7-azabenzotriazol-1-yl)-N,N,N',N'-tetramethyluronium hexafluorophosphate (HATU) (190 mg, 0.5 mmol) were combined in 2 mL DMF under N$_2$ and stirred for 10 min. 1-(2-(aminomethyl)-5-fluorophenyl)pyrrolidin-2-one·HCl (73 mg, 0.3 mmol) and 4-di(methylamino)pyridine (125 mg, 1 mmol) in 2 mL DMF were added and the resulting mixture was stirred for 1 h and then concentrated. The residue was dissolved in CH$_2$Cl$_2$ and washed with dilute HCl. After separation of the layers, the CH$_2$Cl$_2$ layer was dried (MgSO$_4$), filtered and concentrated to give a yellow gum. This was purified by column chromatography (silica gel) eluting with 1:2 CH$_2$Cl$_2$/EtOAc to give 95 mg of the benzyl-protected intermediate amide.

This material was dissolved in 20 mL of a 1:1 solution of EtOH and EtOAc under N$_2$ and 100 mg 10% Pd/C added. The N$_2$ atmosphere was replaced with H$_2$ (1 atm) and the resulting mixture stirred for 4 h. The mixture was filtered and concentrated. The resulting residue was dissolved in CH$_3$CN and diluted with H$_2$O to initiate crystallization. Crystals (45 mg, 57% yield) were collected and vacuum dried. $^1$H NMR (300 MHz, CDCl$_3$) δ: 1.37 (s, 6H), 2.10-2.36 (m, 2H), 2.58 (t, J=8.1 Hz, 2H), 3.54 (s, 2H), 3.70-3.95 (m, 4H), 4.42 (d, J=6.2 Hz, 2H), 4.45-4.85 (m, 2 \H), 6.74-7.09 (m, 2H), 7.47 (dd, J=8.4, 6.2 Hz, 1H), 8.50 (t, J=6.2 Hz, 1H), 12.08 (s, 1H). HRMS (M+H) calcd. for C$_{22}$H$_{26}$FN$_4$O$_5$: 445.1887; found: 445.1884.

The following examples were prepared according to an analogous procedure for example 16.

Example 17

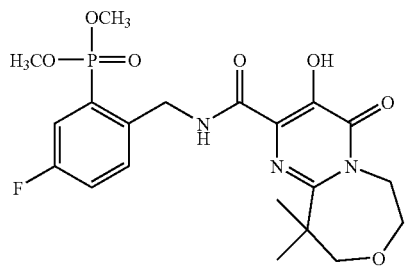

Dimethyl (5-fluoro-2-((((3-hydroxy-10,10-dimethyl-4-oxo-6,7,9,10-tetrahydro-4H-pyrimido[1,2-d][1,4]oxazepin-2-yl)carbonyl)amino)methyl)phenyl)-phosphonate. Yield: 32%. off-white crystals. $^1$H NMR (300 MHz, CDCl$_3$) δ: 1.39 (s, 6H), 3.54 (s, 2H), 3.66-3.95 (m, 2H), 3.75 (s, 3H), 3.80 (s, 3H), 4.20-4.90 (m, 2H), 4.73 (d, J=7.0 Hz, 2H), 7.13-7.29 (m, 1H), 7.32-7.68 (m, 2H), 8.76-8.96 (m, 1H), 12.01 (s, 1H). HRMS (M+H) calcd. for C$_{20}$H$_{26}$FN$_3$O$_7$P: 470.1492; found: 470.1505.

Example 18

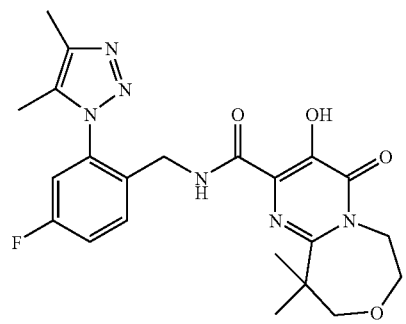

N-(2-(4,5-Dimethyl-1H-1,2,3-triazol-1-yl)-4-fluorobenzyl)-3-hydroxy-10,10-dimethyl-4-oxo-6,7,9,10-tetrahydro-4H-pyrimido[1,2-d][1,4]oxazepine-2-carboxamide. $^1$H NMR (400 MHz, CDCl$_3$) δ: 11.87 (1H, s), 8.50 (1H, t, J=6.6 Hz), 7.73 (1H, dd, J=8.7, 5.9 Hz), 7.28 (1H, td, J=8.3, 2.7 Hz), 7.01 (1H, dd, J=8.3, 2.5 Hz), 4.63 (2H, br s), 4.27 (2H, d, J=6.6 Hz), 3.81 (2H, br s), 3.62 (2H, s), 2.40 (3H, s), 2.23 (3H, s), 1.49 (6H, s). LCMS ($^+$ESI, M+H$^+$) m/z 457.

Example 19

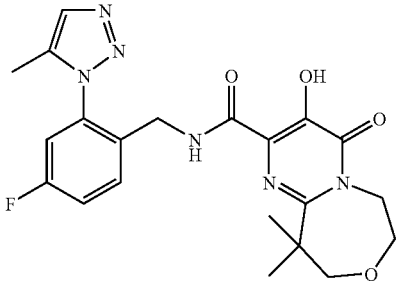

N-(4-fluoro-2-(5-methyl-1H-1,2,3-triazol-1-yl)benzyl)-3-hydroxy-10,10-dimethyl-4-oxo-6,7,9,10-tetrahydro-4H-pyrimido[1,2-d][1,4]oxazepine-2-carboxamide. $^1$HNMR 400 MHz (CDCl$_3$) δ: 11.84 (1H, s), 8.50 (1H, br s), 7.75 (1 H, dd, J=8.6, 5.8 Hz), 7.69 (1H, s), 7.29-7.33 (1H, m), 7.04 (1H, dd, J=8.3, 2.5 Hz), 4.27 (2H, d, J=6.8 Hz), 3.76 (2H, m), 3.63 (2H, s), 2.33 (3H, s), 1.62 (2H, s), 1.50 (6H, s).

Example 20

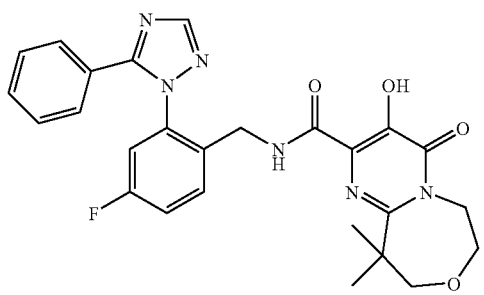

N-((4-fluoro-2-(5-phenyl-1H-1,2,4-triazol-1-yl)phenyl) methyl)-3-hydroxy-10,10-dimethyl-4-oxo-6,7,9,10-tetrahydro-4H-pyrimido[1,2-d][1,4]oxazepine-2-carboxamide. (Yield=76% as white crystals), $^1$H NMR (300 MHz, CHLOROFORM-D) δ ppm 1.40 (s, 6H) 3.55 (s, 2H) 3.61-3.96 (m, 2H) 4.43 (d, J=6.59 Hz, 2H) 6.76 (dd, J=8.42, 2.56 Hz, 1H) 7.10-7.49 (m, 6H) 7.69 (dd, J=8.78, 5.86 Hz, 1H) 8.09 (s, 1H) 8.48 (t, J=6.59 Hz, 1H) 11.81 (s, 1H); HRMS (M+H) calcd for C$_{26}$H$_{25}$F$_1$N$_6$O$_4$: 505.2000; found: 505.2004.

Example 21

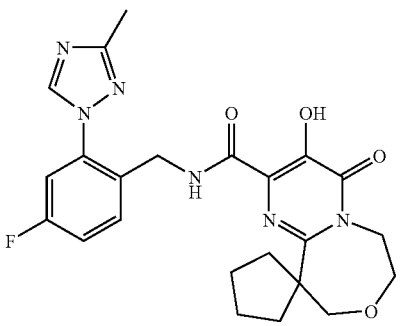

N-((4-fluoro-2-(3-methyl-1H-1,2,4-triazol-1-yl)phenyl) methyl)-3'-hydroxy-4'-oxo-6',7'-dihydro-4'H-spiro[cyclopentane-1,10'-pyrimido[1,2-d][1,4]oxazepine]-2'-carboxamide. $^1$H NMR (300 MHz, CHLOROFORM-D) δ ppm 1.50-2.38 (m, 8H) 2.50 (s, 3H) 3.50 (s, 2H) 3.68-3.83 (m, 2H) 4.45 (d, J=7.14 Hz, 2H) 4.49-4.68 (m, 2H) 6.97-7.22 (m, 2H) 7.69 (dd, J=8.60, 6.04 Hz, 1H) 8.29 (s, 1H) 8.45-8.71 (m, 1H) 12.12 (s, 1H); HRMS (M+H) calcd for C$_{23}$H$_{25}$FN$_6$O$_4$: 469.2000; found: 469.2018.

Example 22

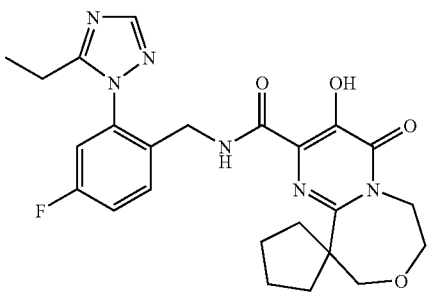

N-((2-(5-ethyl-1H-1,2,4-triazol-1-yl)-4-fluorophenyl)methyl)-3'-hydroxy-4'-oxo-6',7'-dihydro-4'H-spiro[cyclopentane-1,10'-pyrimido[1,2-d][1,4]oxazepine]-2'-carboxamide. $^1$H NMR (300 MHz, CHLOROFORM-D) δ ppm 1.29 (t, J=7.68 Hz, 3 H) 1.46-2.41 (m, 8H) 2.74 (q, J=7.56 Hz, 2H) 3.52 (s, 2H) 3.60-3.85 (m, 2H) 4.24 (d, J=6.95 Hz, 2H) 4.45-4.70 (m, 2H) 6.99 (dd, J=8.42, 2.56 Hz, 1H) 7.13-7.29 (m, 1H) 7.66 (dd, J=8.60, 6.04 Hz, 1H) 7.95 (s, 1H) 8.48-8.62 (m, 1H) 11.89 (s, 1H); HRMS (M+H) calcd for C$_{24}$H$_{27}$FN$_6$O$_4$: 483.2156; found: 483.2145.

Example 23

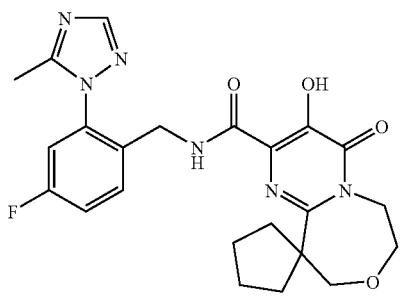

N-((4-fluoro-2-(5-methyl-1H-1,2,4-triazol-1-yl)phenyl) methyl)-3'-hydroxy-4'-oxo-6',7'-dihydro-4'H-spiro[cyclopentane-1,10'-pyrimido[1,2-d][1,4]oxazepine]-2'-carboxamide. $^1$H NMR (300 MHz, CHLOROFORM-D) δ ppm 1.50-2.39 (m, 8H) 2.50 (s, 3H) 3.52 (s, 2H) 3.63-3.87 (m, 2H) 4.26 (d, J=6.95 Hz, 2H) 4.55-4.77 (m, 2H) 6.99 (dd, J=8.42, 2.56 Hz, 1H) 7.12-7.30 (m, 1H) 7.67 (dd, J=8.60, 6.04 Hz, 1H) 7.94 (s, 1H) 8.45-8.66 (m, 1H) 11.89 (s, 1H); HRMS (M+H) calcd for C$_{23}$H$_{25}$FN$_6$O$_4$: 469.2000; found: 469.2018.

Example 24

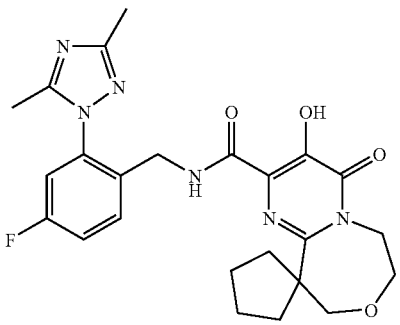

N-((2-(3,5-dimethyl-1H-1,2,4-triazol-1-yl)-4-fluorophenyl)methyl)-3'-hydroxy-4'-oxo-6',7'-dihydro-4'H-spiro[cyclopentane-1,10'-pyrimido[1,2-d][1,4]oxazepine]-2'-carboxamide. $^1$H NMR (300 MHz, CHLOROFORM-D) δ ppm 1.50-2.29 (m, 8H) 2.35 (s, 3H) 2.48 (s, 3H) 3.50 (s, 2H) 3.62-3.87 (m, 2H) 4.30 (d, J=6.95 Hz, 2H) 4.41-4.74 (m, 2H) 6.96 (dd, J=8.42, 2.56 Hz, 1H) 7.11-7.31 (m, 1H) 7.66 (dd, J=8.60, 6.04 Hz, 1H) 8.22-8.38 (m, 1H) 12.04 (s, 1H); HRMS (M+H) calcd for $C_{24}H_{27}FN_6O_4$: 483.2156; found: 483.2167.

Example 25

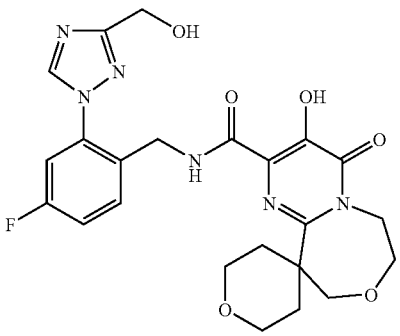

N-((4-fluoro-2-(3-(hydroxymethyl)-1H-1,2,4-triazol-1-yl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. $^1$H NMR (500 MHz, CHLOROFORM-D) δ ppm 3.56-4.14 (m, 12H) 4.39-4.62 (m, 4H) 4.84 (s, 2H) 7.06-7.36 (m, 2H) 7.69 (dd, J=8.55, 5.80 Hz, 1H) 8.43 (s, 1H) 8.49-8.70 (m, 1H) 12.03 (s, 1H); HRMS (M+H) calcd for $C_{23}H_{25}FN_6O_6$: 501.1898; found: 501.1898.

Example 26

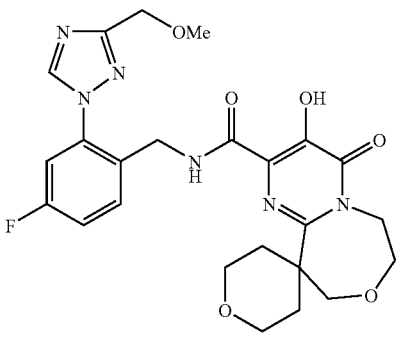

N-((4-fluoro-2-(3-((methyloxy)methyl)-1H-1,2,4-triazol-1-yl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. N-((4-fluoro-2-(3-(hydroxymethyl)-1H-1,2,4-triazol-1-yl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide (190 mg, 0.32 mmol) was dissolved in 3 mL $CH_2Cl_2$ under $N_2$ and treated with 100 mg triethylamine followed by mesylchloride (46 mg, 0.4 mmol) in 0.5 mL $CH_2Cl_2$. This was stirred for 30 min and then washed with dilute HCl. The crude product was purified by column chromatography on silica, eluted with EtOAc to give 170 mg of a clear gum. This was dissolved in 30 mL MeOH and heated at 70° C. in a sealed flask for 18 hrs and then concentrated. The residue was stirred with 5 mL TFA for 30 min and concentrated. The residue gave 45 mg of white crystals from 95%-EtOH. (Yield=34%) $^1$H NMR (500 MHz, CHLOROFORM-D) δ ppm 3.50 (s, 3H) 3.55-4.13 (m, 14H) 4.50 (d, J=5.80 Hz, 2H) 4.63 (s, 2H) 7.06-7.28 (m, 2H) 7.69 (dd, J=8.55, 5.80 Hz, 1H) 8.36 (t, J=6.87 Hz, 1H) 8.40 (s, 1H) 12.10 (s, 1H); HRMS (M+H) calcd for $C_{24}H_{27}FN_6O_6$: 515.2054; found: 515.2032.

Example 27

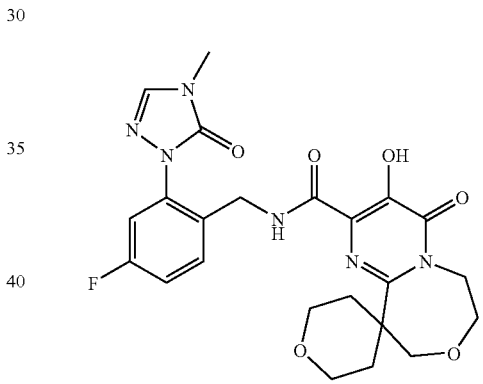

N-(4-Fluoro-2-(4-methyl-5-oxo-4,5-dihydro-1H-1,2,4-triazol-1-yl)benzyl)-3'-hydroxy-4'-oxo-2,3,4',5,6,6',7',9'-octahydrospiro[pyran-4,10'-pyrimido[1,2-d][1,4]oxazepine]-2'-carboxamide: To a solution of 3'-(benzyloxy)-N-(4-fluoro-2-(4-methyl-5-oxo-4,5-dihydro-1H-1,2,4-triazol-1-yl)benzyl)-4'-oxo-2,3,4',5,6,6',7',9'-octahydrospiro[pyran-4,10'-pyrimido[1,2-d][1,4]oxazepine]-2'-carboxamide (0.093 g, 0.174 mmol) in ethyl acetate (5 mL) was added palladium on activated carbon (10%) (0.050 g) and the resulting mixture allowed to react under one atmosphere of hydrogen for 6 hours. The catalyst was removed by filtration and the filtrate was evaporated under reduce pressure to give a white solid. Recrystallization from hot ethanol afforded the title compound as a white solid (0.053 g, 68% yield): $^1$H NMR (400 MHz, $CDCl_3$) δ 12.28 (1H, s), 8.95 (1H, brt), 7.66 (1H, dd, J=8.6, 6.1 Hz), 7.63 (1H, s), 7.22 (2H, dd, J=9.2, 2.8 Hz), 7.12 (2H, td, J=8.2, 2.8 Hz), 4.53 (2H, brs), 3.7-3.90 (10H, m), 3.43 (3H, s), 2.2-2.5 (2H, brm), 1.5-2.0 (2H, brm); LCMS ($^+$ESI, M+H$^+$) m/z 501.

Example 28

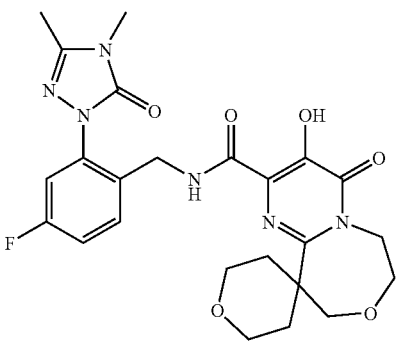

N-(2-(3,4-dimethyl-5-oxo-4,5-dihydro-1H-1,2,4-triazol-1-yl)-4-fluorobenzyl)-3'-hydroxy-4'-oxo-2,3,4',5,6,6',7',9'-octahydrospiro[pyran-4,10'-pyrimido[1,2-d][1,4]oxazepine]-2'-carboxamide: $^1$H NMR (400 MHz, CDCl$_3$) δ 12.36 (1H, brs), 9.01 (1H, brs), 7.64 (1H, dd, J=8.6, 6.1 Hz), 7.17 (1H, dd, J=9.3, 2.8 Hz), 7.09 (1 H, td, J=8.1, 2.8 Hz), 4.53 (2H, brs), 4.0-3.5 (10H, brm), 3.33 (3H, s), 2.5-2.3 (2 H, m), 2.36 (3H, s), 2.07-1.5 (2H, brm); LCMS ($^+$ESI, M+H$^+$) m/z 515.

Example 29

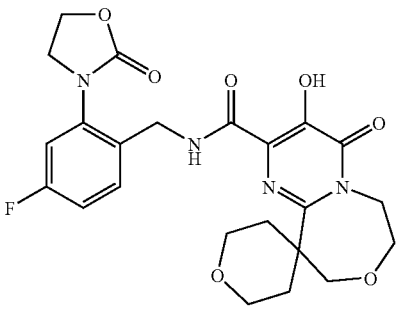

N-(4-fluoro-2-(2-oxooxazolidin-3-yl)benzyl)-3'-hydroxy-4'-oxo-2,3,4',5,6,6',7',9'-octahydrospiro[pyran-4,1'-pyrimido[1,2-d][1,4]oxazepine]-2'-carboxamide: $^1$H NMR (400 MHz, CDCl$_3$) δ 12.18 (1H, brs), 8.63 (1H, brt, J=6.3 Hz), 7.60 (1H, dd, J=8.6, 6.3 Hz), 7.08 (1H, td, J=8.2, 2.5 Hz), 6.98 (1H, dd, J=9.2, 2.5 Hz), 4.53-4.63 (4H, m), 4.05-4.15 (2H, t, J=7.3 Hz), 3.9-3.6 (10H, m), 2.4-2.3 (2H, brs), 2.1-1.6 (2H, brm); LCMS ($^+$ESI, M+H$^+$) m/z 489.

Example 30

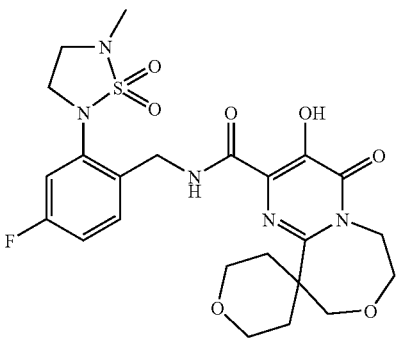

N-(4-fluoro-2-(1,1-dioxo-5-methyl-1,2,5-thiazolidin-2-yl)benzyl)-3'-hydroxy-4'-oxo-2,3,4',5,6,6',7',9'-octahydrospiro[pyran-4,10'-pyrimido[1,2-d][1,4]oxazepine]-2'-carboxamide: $^1$H NMR (400 MHz, CDCl$_3$) δ 12.18 (1H, s), 8.32 (1H, t, J=6.7 Hz), 7.67 (1H, dd, J=8.6, 6.3 Hz), 7.08-7.17 (2H, m), 4.70 (2H, d, J=6.6 Hz), 3.90-3.60 (12H, m), 3.53 (2H, t, J=6.4 Hz), 2.85 (3H, s), 2.5-2.1 (2 H, brs), 2.00-1.60 (2H, brs); LCMS ($^+$ESI, M+H$^+$) m/z 538.

Example 31

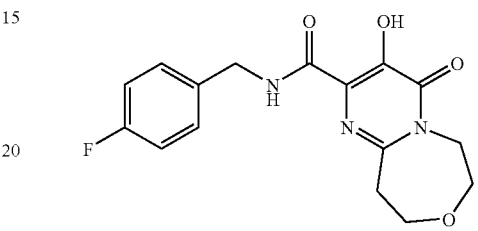

N-((4-fluorophenyl)methyl)-3-hydroxy-4-oxo-6,7,9,10-tetrahydro-4H-pyrimido[1,2-d][1,4]oxazepine-2-carboxamide. White crystals (70% yield): mp 197-199° C. (ethyl acetate). $^1$HNMR 400 MHz (CDCl$_3$) δ (ppm): 3.13 (2H, m, CH$_2$), 3.85-3.89 (4H, m, 2×CH$_2$), 4.52 (2H, m, CH$_2$), 4.59 (2H, d, J=6.4 Hz, NCH$_2$), 7.08 (2H, m, aromatics), 7.34 (2H, m, aromatics), 7.90 (1H, broad t, NH), 12.08 (1H, s, OH). Anal. Calcd for C$_{16}$H$_{16}$FN$_3$O$_4$: C 57.65, H 4.83, N 12.60; Found: C 57.38, H 4.58, N 12.47.

Example 32

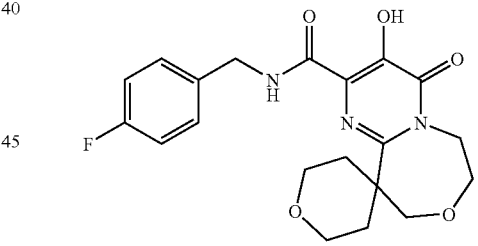

N-((4-fluorophenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. A solution of intermediate 171 (0.240 g, 0.486 mmol) in a mixture of ethyl acetate (125 ml) and ethanol (25 ml) at 25° C. was hydrogenated over 10% palladium on activated carbon (0.24 g) and under one atmosphere of hydrogen for 2 hours. The catalyst was removed by filtration and the filtrate was evaporated under reduce pressure to give a white solid. Recrystallization from ethyl acetate gave 0.143 g (73% yield) of the title compound as white crystals. $^1$HNMR 400 MHz (DMSO-d$_6$) δ (ppm): 1.5-2.0 (2H, broad m, CH$_2$), 2.2-2.5 (2H, broad m, CH$_2$), 3.4-4.0 (10H, broad m, 5×CH$_2$), 4.50 (2H, d, J=6.5 Hz, NCH$_2$), 7.18 (2H, m, aromatics), 7.37 (2H, m, aromatics), 9.07 (1H, broad t, NH), 12.29 (1H, s, OH). HRMS (ESI$^+$) calculated for C$_{20}$H$_{23}$FN$_3$O$_5$ [M+H$^+$]: 404.1622; found: 404.1624.

Example 33

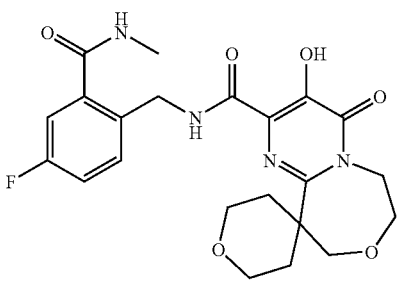

N-((4-fluoro-2-((methylamino)carbonyl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. White crystals (93% yield). $^1$HNMR 400 MHz (CDCl$_3$) δ (ppm): 1.7-2.0 (2H, broad m, CH$_2$), 2.2-2.6 (2H, broad m, CH$_2$), 3.02 (3H, d, J=4.8 Hz, NCH$_3$), 3.4-4.0 (10H, broad m, 5×CH$_2$), 4.58 (2H, d, J=6.9 Hz, NCH$_2$), 6.14 (1H, broad q, NH), 7.14-7.21 (2H, m, aromatics), 7.54 (1H, m, aromatic), 9.11 (1H, broad t, NH), 12.17 (1H, s, OH). HRMS (ESI$^+$) calculated for C$_{22}$H$_{26}$FN$_4$O$_6$ [M+H$^+$]: 461.1836; found: 461.1849.

Example 34

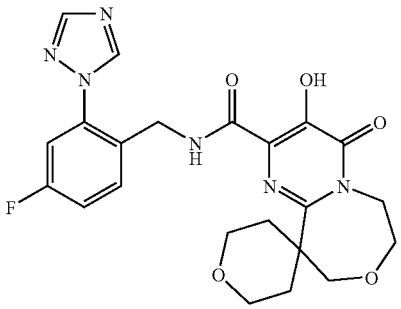

N-((4-fluoro-2-(1H-1,2,4-triazol-1-yl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. White crystals (90% yield). $^1$HNMR 400 MHz (DMSO-d$_6$) δ (ppm): 1.5-1.9 (2H, broad m, CH$_2$), 2.1-2.5 (2H, broad m, CH$_2$), 3.5-3.9 (10H, broad m, 5×CH$_2$), 4.46 (2H, d, J=6.4 Hz, NCH$_2$), 7.42 (1H, m, aromatic), 7.57-7.62 (2H, m, aromatics), 8.33 (1H, s, CH), 9.02 (1H, broad t, NH), 9.08 (1H, s, CH), 12.02 (1H, s, OH). HRMS (ESI$^+$) calculated for C$_{22}$H$_{24}$FN$_6$O$_5$ [M+H$^+$]: 471.1792; found: 471.1802.

Example 35

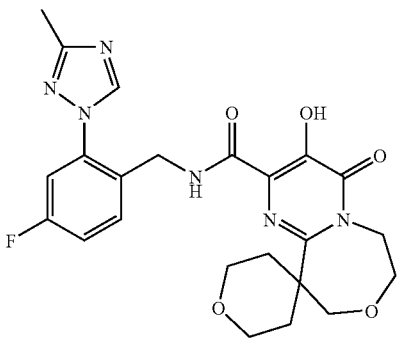

N-((4-fluoro-2-(3-methyl-1H-1,2,4-triazol-1-yl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. White crystals (79% yield). $^1$HNMR 400 MHz (CDCl$_3$) δ (ppm): 1.6-2.0 (2H, broad m, CH$_2$), 2.1-2.5 (2H, broad m, CH$_2$), 2.55 (3H, s, CH$_3$), 3.5-4.0 (10H, broad m, 5×CH$_2$), 4.52 (2H, d, J=6.6 Hz, NCH$_2$), 7.12 (1H, dd, J=2.6 Hz and J=8.6 Hz, aromatic), 7.20 (1H, m, aromatic), 7.71 (1H, dd, J=6.1 Hz and J=8.6 Hz, aromatic), 8.34 (1H, s, CH), 8.54 (1H, broad t, NH), 12.22 (1H, s, OH). HRMS (ESI$^+$) calculated for C$_{23}$H$_{26}$FN$_6$O$_5$ [M+H$^+$]: 485.1949; found: 485.1927.

Example 36

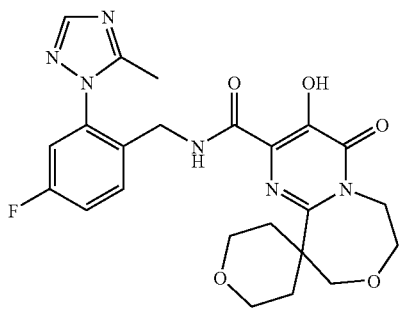

N-((4-fluoro-2-(5-methyl-1H-1,2,4-triazol-1-yl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. White crystals (78% yield). $^1$HNMR 400 MHz (CDCl$_3$) δ (ppm): 1.6-2.1 (2H, broad m, CH$_2$), 2.1-2.5 (2H, broad m, CH$_2$), 2.52 (3H, s, CH$_3$), 3.5-4.0 (10H, broad m, 5×CH$_2$), 4.32 (2H, d, J=6.6 Hz, NCH$_2$), 7.05 (1H, dd, J=2.7 Hz and J=8.5 Hz, aromatic), 7.27 (1H, m, aromatic), 7.71 (1H, dd, J=5.8 Hz and J=8.5 Hz, aromatic), 8.00 (1H, s, CH), 8.58 (1H, broad t, NH), 12.03 (1H, s, OH). HRMS (ESI$^+$) calculated for C$_{23}$H$_{26}$FN$_6$O$_5$ [M+H$^+$]: 485.1949; found: 485.1930.

Example 37

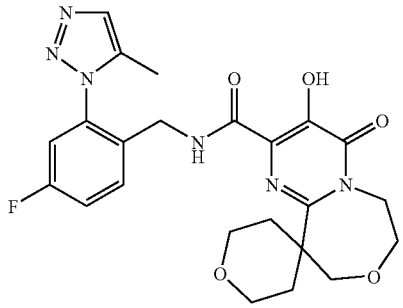

N-((4-fluoro-2-(5-methyl-1H-1,2,3-triazol-1-yl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. White crystals (76% yield). $^1$HNMR 400 MHz (CDCl$_3$) δ (ppm): 1.6-2.1 (2H, broad m, CH$_2$), 2.2-2.6 (2H, broad m, CH$_2$), 2.35 (3H, s, CH$_3$), 3.4-4.0 (10H, broad m, 5×CH$_2$), 4.25 (2H, d, J=6.1 Hz, NCH$_2$), 7.03 (1H, dd, J=2.6 Hz and J=8.5 Hz, aromatic), 7.31 (1H, m, aromatic), 7.68 (1H, s, CH), 7.76 (1H, dd, J=5.8 Hz and J=8.5 Hz, aromatic), 8.59 (1H, broad t, NH), 11.95 (1H, s, OH). HRMS (ESI$^+$) calculated for C$_{23}$H$_{26}$FN$_6$O$_5$ [M+H$^+$]: 485.1949; found: 485.1961.

Example 38

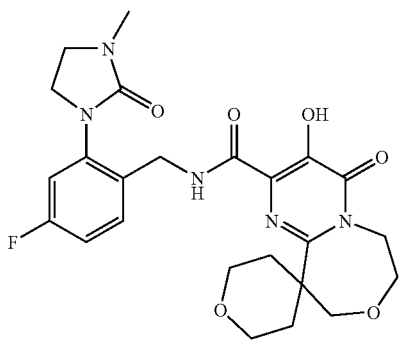

N-((4-fluoro-2-(3-methyl-2-oxo-1-imidazolidinyl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. White crystals (89% yield). $^1$HNMR 400 MHz (CDCl$_3$) δ (ppm): 1.6-2.1 (2H, broad m, CH$_2$), 2.2-2.6 (2H, broad m, CH$_2$), 2.91 (3H, s, CH$_3$), 3.57 (2H, t, J=7.9 Hz, CH$_2$), 3.6-4.0 (10H, broad m, 5×CH$_2$), 3.83 (2H, t, J=7.9 Hz, CH$_2$), 4.51 (2H, broad d, NCH$_2$), 6.89 (1H, dd, J=2.8 Hz and J=9.9 Hz, aromatic), 6.98 (1H, m, aromatic), 7.59 (1H, dd, J=6.4 Hz and J=8.6 Hz, aromatic), 9.03 (1H, broad t, NH), 12.43 (1H, s, OH). HRMS (ESI$^+$) calculated for C$_{24}$H$_{29}$FN$_5$O$_6$ [M+H$^+$]: 502.2102; found: 502.2109.

Example 39

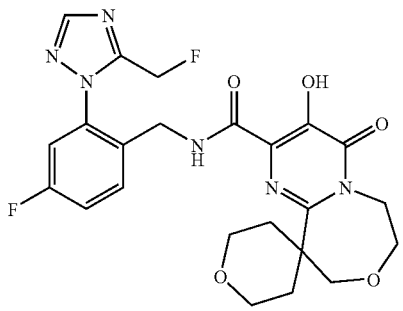

N-((4-fluoro-2-(5-(fluoromethyl)-1H-1,2,4-triazol-1-yl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. White crystals (83% yield). $^1$HNMR 400 MHz (CDCl$_3$) δ (ppm): 1.6-2.1 (2H, broad m, CH$_2$), 2.1-2.5 (2H, broad m, CH$_2$), 3.5-4.0 (10H, broad m, 5×CH$_2$), 4.33 (2H, d, J=6.6 Hz, NCH$_2$), 5.47 (2H, d, J=47.5 Hz, CH$_2$F), 7.21 (1H, dd, J=2.5 Hz and J=8.4 Hz, aromatic), 7.31 (1H, m, aromatic), 7.73 (1H, dd, J=5.9 Hz and J=8.7 Hz, aromatic), 8.16 (1H, s, CH), 8.42 (1H, broad t, NH), 11.98 (1H, s, OH). MS (ESI$^+$) m/e 503 [M+H$^+$].

Example 40

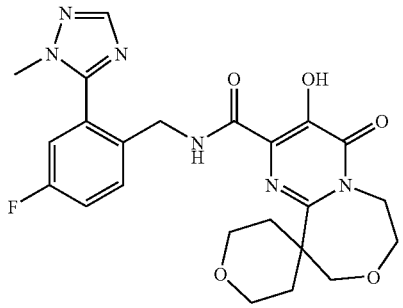

N-((4-fluoro-2-(1-methyl-1H-1,2,4-triazol-5-yl)phenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. White crystals (93% yield). $^1$HNMR 400 MHz (CDCl$_3$) δ (ppm): 1.4-2.1 (2H, broad m, CH$_2$), 2.2-2.7 (2H, broad m, CH$_2$), 3.5-4.0 (10H, broad m, 5×CH$_2$), 4.01 (3H, s, CH$_3$), 4.45 (2H, d, J=6.6 Hz, NCH$_2$), 7.17 (1H, dd, J=2.5 Hz and J=8.6 Hz, aromatic), 7.26 (1H, m, aromatic), 7.72 (1H, dd, J=5.8 Hz and J=8.6 Hz, aromatic), 7.99 (1H, s, CH), 9.37 (1H, broad t, NH), 12.18 (1H, s, OH). HRMS (ESI$^+$) calculated for C$_{23}$H$_{26}$FN$_6$O$_5$ [M+H$^+$]: 485.1949; found: 485.1960.

Example 41

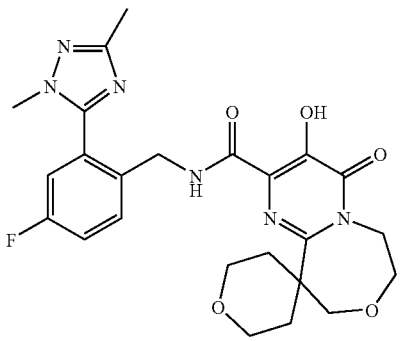

N-((2-(1,3-dimethyl-1H-1,2,4-triazol-5-yl)-4-fluorophenyl)methyl)-3'-hydroxy-4'-oxo-2,3,5,6,6',7'-hexahydro-4'H-spiro[pyran-4,10'-pyrimido[1,2-d][1,4]oxazepine]-2'-carboxamide. White crystals (67% yield). $^1$HNMR 400 MHz (CDCl$_3$) δ (ppm): 1.5-2.1 (2H, broad m, CH$_2$), 2.1-2.6 (2H, broad m, CH$_2$), 2.46 (3H, s, CH$_3$), 3.5-4.0 (10H, broad m, 5×CH$_2$), 3.90 (3H, s, CH$_3$), 4.49 (2H, d, J=6.6 Hz, NCH$_2$), 7.14 (1H, dd, J=2.5 Hz and J=8.6 Hz, aromatic), 7.24 (1H, m, aromatic), 7.69 (1H, dd, J=5.6 Hz and J=8.6 Hz, aromatic), 8.93 (1H, broad t, NH), 12.35 (1H, s, OH). HRMS (ESI$^+$) calculated for C$_{24}$H$_{28}$FN$_6$O$_5$ [M+H$^+$]: 499.2105; found: 499.2109.

Example 42

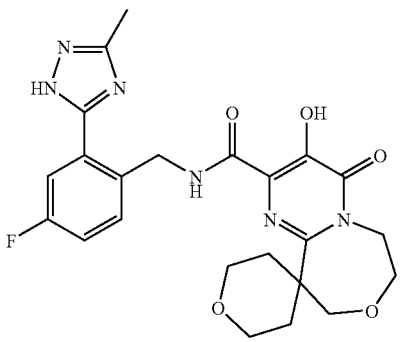

N-((4-fluoro-2-(3-methyl-1H-1,2,4-triazol-5-yl)phenyl) methyl)-3'-hydroxy-4'-oxo-2,3,5,6,6',7'-hexahydro-4'H-spiro[pyran-4,10'-pyrimido[1,2-d][1,4]oxazepine]-2'-carboxamide. White crystals (69% yield). $^1$HNMR 400 MHz (DMSO-$d_6$) δ (ppm): 1.4-2.0 (2H, broad m, $CH_2$), 2.0-2.6 (2H, broad m, $CH_2$), 2.48 (3H, s, $CH_3$), 3.4-4.0 (10H, broad m, 5×$CH_2$), 4.77 (2H, d, J=6.0 Hz, $NCH_2$), 7.26 (1H, m, aromatic), 7.51 (1H, dd, J=5.8 Hz and J=8.6 Hz, aromatic), 7.79 (1H, dd, J=2.5 Hz and J=10.6 Hz, aromatic), 9.25 (1H, broad t, NH), 12.21 (1H, s, OH), 14.03 (1H, s, NH). HRMS (ESI$^+$) calculated for $C_{23}H_{26}FN_6O_5$ [M+H$^+$]: 485.1949; found: 485.1947.

We claim:

1. A compound of Formula I

I wherein:

R$^1$ is (Ar$^1$)alkyl, (Ar$^1$)(CON(R$^8$)(R$^9$))alkyl, (Ar$^1$) (CO$_2$R$^{14}$)alkyl, (Ar$^1$)hydroxyalkyl, or (Ar$^1$)oxyalkyl;

R$^2$ is hydrogen, alkyl, hydroxy or alkoxy;

R$^3$ is hydrogen, halo, hydroxy, cyano, alkyl, cycloalkyl, C$_{5-7}$cycloalkenyl, haloalkyl, alkoxy, alkylthio, haloalkoxy, N(R$^8$)(R$^9$), NHAr$^2$, N(R$^6$)SO$_2$R$^7$, N(R$^6$) COR$^7$, N(R$^6$)CO$_2$R$^7$, OCOR$^7$, OCO$_2$R$^7$, OCON(R$^8$) (R$^9$), OCH$_2$CO$_2$R$^7$, OCH$_2$CON(R$^8$)(R$^9$), COR$^6$, CO$_2$R$^6$, CON(R$^8$)(R$^9$), SOR$^7$, S(=NR$^7$), SO$_2$R$^7$, SO$_2$N (R$^6$)(R$^6$), PO(OR$^6$)$_2$, C$_{2-4}$(R$^{12}$)alkynyl, R$^{13}$, Ar$^2$, or Ar$^3$;

R$^4$ is hydrogen, halo, hydroxy, cyano, alkyl, alkoxy, haloalkyl, haloalkoxy, or N(R$^6$)(R$^6$);

R$^5$ is hydrogen, halo, hydroxy, cyano, alkyl, alkoxy, haloalkyl, haloalkoxy, or N(R$^6$)(R$^6$);

R$^6$ is hydrogen, alkyl, or cycloalkyl;

R$^7$ is alkyl or cycloalkyl;

R$^8$ is hydrogen, alkyl, hydroxyalkyl, alkoxyalkyl or dialkylaminoalkyl;

R$^9$ is hydrogen, alkyl, hydroxyalkyl, alkoxyalkyl or dialkylaminoalkyl; or

N(R$^8$)(R$^9$) taken together is azetidinyl, pyrrolidinyl, (R$^{10}$)-piperidinyl, N—(R$^{11}$)-piperazinyl, morpholinyl, thiomorpholinyl, or dioxothiazinyl;

R$^{10}$ is hydrogen, alkyl, hydroxy, or hydroxyalkyl;

R$^{11}$ is hydrogen, alkyl, cyclolkyl, COR$^6$, or CO$_2$R$^6$;

R$^{12}$ is hydrogen, hydroxy, N(R$^6$)(R$^6$), SO$_2$R$^7$, OSO$_2$R$^7$, or dioxothiazinyl;

R$^{13}$ is azetidinonyl, pyrrolidinonyl, valerolactamyl, caprolactamyl, maleimido, oxazolidinonyl, imidazolidinonyl, triazolonyl, dioxothiazolidinyl or dioxothiazinyl, and is substituted with 0-2 substituents selected from the group consisting of alkyl, hydroxyalkyl, haloalkyl, alkoxyalkyl, and aminoalkyl;

R$^{14}$ is methyl;

Ar$^1$ is

Ar$^2$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, alkyl, alkoxy, N(R$^8$)(R$^9$), CON(R$^8$)(R$^9$), CO$_2$R$^6$, CONHSO$_2$N(R$^6$)(R$^6$), CONHSO$_2$N(R$^6$)(phenyl), and CONHSO$_2$N(R$^6$)(halophenyl);

Ar$^3$ is phenyl substituted with 0-2 substituents selected from the group consisting of halo, cyano, hydroxy, alkyl, alkoxy, alkoxymethyl, haloalkyl, haloalkoxy, N(R$^8$) (R$^9$), CON(R$^6$)(R$^6$), and CH$_2$N(R$^8$)(R$^9$), or is dioxolanylphenyl; and X—Y—Z is C(R$^{14}$)$_2$CH$_2$OCH$_2$CH$_2$;

or a pharmaceutically acceptable salt thereof.

2. A compound of claim 1 where

R$^1$ is C$_{1-6}$(Ar$^1$)alkyl, C$_{1-6}$(Ar$^1$)(CON(R$^8$)(R$^9$))alkyl, C$_{1-6}$ (Ar$^1$)(CO$_2$R$^{14}$)alkyl, C$_{1-6}$(Ar$^1$)hydroxyalkyl, or C$_{1-6}$ (Ar$^1$)oxyalkyl;

R$^2$ is hydrogen, C$_{1-6}$alkyl, hydroxy or alkoxy;

R$^3$ is hydrogen, halo, hydroxy, cyano, C$_{1-6}$alkyl, C$_{3-7}$cycloalkyl, C$_{5-7}$cycloalkenyl, C$_{1-6}$haloalkyl, C$_{1-6}$alkoxy, C$_{1-6}$alkylthio, C$_{1-6}$haloalkoxy, N(R$^8$)(R$^9$), NHAr$^2$, N(R$^6$)SO$_2$R$^7$, N(R$^6$)COR$^7$, N(R$^6$)CO$_2$R$^7$, OCOR$^7$, OCO$_2$R$^7$, OCON(R$^8$)(R$^9$), OCH$_2$CO$_2$R$^7$, OCH$_2$CON (R$^8$)(R$^9$), COR$^6$, CO$_2$R$^6$, CON(R$^8$)(R$^9$), SOR$^7$, SO$_2$R$^7$, SO$_2$N(R$^6$)(R$^6$), PO(OR$^6$)$_2$, C$_{2-4}$(R$^{12}$)alkynyl, R$^{13}$, Ar$^2$, or Ar$^3$;

R$^4$ is hydrogen, halo, hydroxy, cyano, C$_{1-6}$alkoxy, C$_{1-6}$haloalkyl, C$_{3-6}$haloalkoxy, or N(R$^6$)(R$^6$);

R$^5$ is hydrogen, halo, hydroxy, cyano, C$_{1-6}$alkyl, C$_{1-6}$alkoxy, C$_{1-6}$haloalkyl, C$_{1-6}$haloalkoxy, or N(R$^6$) (R$^6$);

R$^6$ is hydrogen, C$_{1-6}$alkyl, or C$_{3-7}$cycloalkyl;

R$^7$ is C$_{1-6}$alkyl or C$_{3-7}$cycloalkyl;

R$^8$ is hydrogen, C$_{1-6}$alkyl, C$_{1-6}$hydroxyalkyl, C$_{1-6}$(C$_{1-6}$alkoxy)alkyl or C$_{1-6}$(C$_{1-6}$dialkylamino)alkyl;

R⁹ is hydrogen, C₁₋₆alkyl, C₁₋₆hydroxyalkyl, C₁₋₆(C₁₋₆alkoxy)alkyl or C₁₋₆(C₁₋₆ dialkylamino)alkyl; or N(R⁸)(R⁹) taken together is azetidinyl, pyrrolidinyl, (R¹⁰)-piperidinyl, N—(R¹¹)-piperazinyl, morpholinyl, thiomorpholinyl, or dioxothiazinyl;

R¹⁰ is hydrogen, C₁₋₆alkyl, or C₁₋₆hydroxyalkyl;

R¹¹ is hydrogen, C₁₋₆alkyl, C₃₋₇cyclolkyl, COR⁶, or CO₂R⁶;

R¹² is hydrogen, hydroxy, N(R⁶)(R⁶), SO₂R⁷, OSO₂R⁷, or dioxothiazinyl;

R¹³ is azetidinonyl, pyrrolidinonyl, valerolactamyl, caprolactamyl, maleimido, oxazolidinonyl, or dioxothiazinyl, and is substituted with 0-1 substituents selected from the group consisting of hydroxymethyl, methoxymethyl, and aminomethyl;

R¹⁴ is dependently hydrogen or methyl;

Ar¹ is

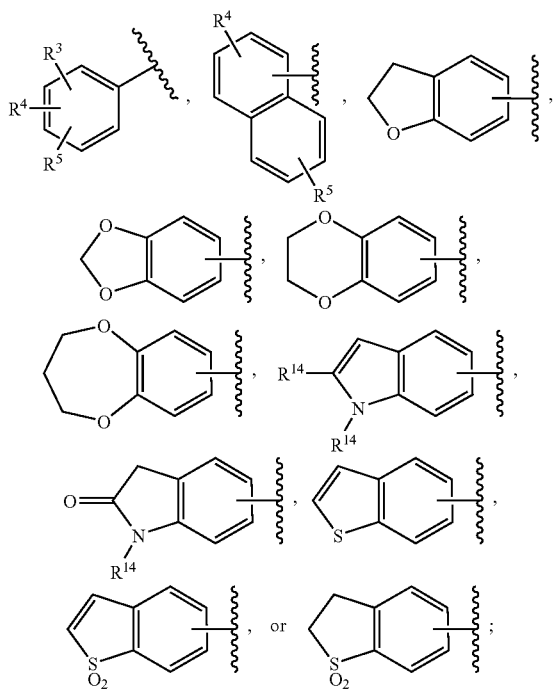

Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, alkyl, alkoxy, N(R⁸)(R⁹), CON(R⁸)(R⁹), CO₂R⁶, CONHSO₂N(R⁶)(R⁶), CONHSO₂N(R⁶)(phenyl), and CONHSO₂N(R⁶)(halophenyl);

Ar³ is phenyl substituted with 0-2 substituents selected from the group consisting of halo, cyano, hydroxy, alkyl, alkoxy, alkoxyalkyl, haloalkyl, haloalkoxy, N(R⁸)(R⁹), CON(R⁶)(R⁶), and CH₂N(R⁸)(R⁹), or is dioxolanylphenyl; and X—Y—Z is C(R¹⁴)₂CH₂OCH₂CH₂;

or a pharmaceutically acceptable salt thereof.

3. A compound of claim 1 where R¹ is (Ar¹)alkyl.

4. A compound of claim 1 where R¹ is

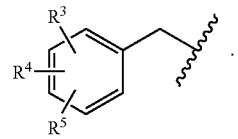

5. A compound of claim 1 where R¹ is

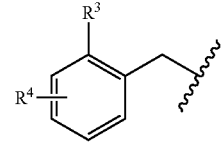

and R³ is other than hydrogen or halo.

6. A compound of claim 5 where R³ is N(R⁸)(R⁹), N(R⁶)COR⁷, OCON(R⁸)(R⁹), CON(R⁸)(R⁹), SOR⁷, SO₂R⁷, SO₂N(R⁶)(R⁶), PO(OR⁶)₂, R¹³, or Ar².

7. A compound of claim 5 where R³ is R¹³.

8. A compound of claim 5 where R³ is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl, and is substituted with 0-2 substituents selected from the group consisting of halo and alkyl.

9. A compound of claim 1 where R² is hydrogen.

10. A compound of claim 1 selected from the group consisting of

N-((4-Fluorophenyl)methyl)-3-hydroxy-10,10-dimethyl-4-oxo-6,7,9,10-tetrahydro-4H-pyrimido[1,2-d][1,4]oxazepine-2-carboxamide;

N-((4-Fluoro-2-(1H-1,2,4-triazol-1-yl)phenyl)methyl)-3-hydroxy-10,10-dimethyl-4-oxo-6,7,9,10-tetrahydro-4H-pyrimido[1,2-d][1,4]oxazepine-2-carboxamide;

N-((4-Fluoro-2-(methylsulfonyl)phenyl)methyl)-3-hydroxy-10,10-dimethyl-4-oxo-6,7,9,10-tetrahydro-4H-pyrimido[1,2-d][1,4]oxazepine-2-carboxamide;

N-((4-Fluoro-2-(5-methyl-1H-1,2,4-triazol-1-yl)phenyl)methyl)-3-hydroxy-10,10-dimethyl-4-oxo-6,7,9,10-tetrahydro-4H-pyrimido[1,2-d][1,4]oxazepine-2-carboxamide;

N-((2-(3,5-dimethyl-1H-1,2,4-triazol-1-yl)-4-fluorophenyl)methyl)-3-hydroxy-10,10-dimethyl-4-oxo-6,7,9,10-tetrahydro-4H-pyrimido[1,2-d][1,4]oxazepine-2-carboxamide;

N-((4-fluoro-2-(3-methyl-1H-1,2,4-triazol-1-yl)phenyl)methyl)-3-hydroxy-10,10-dimethyl-4-oxo-6,7,9,10-tetrahydro-4H-pyrimido[1,2-d][1,4]oxazepine-2-carboxamide;

N-((4-fluoro-2-(2-oxo-1-pyrrolidinyl)phenyl)methyl)-3-hydroxy-10,10-dimethyl-4-oxo-6,7,9,10-tetrahydro-4H-pyrimido[1,2-d][1,4]oxazepine-2-carboxamide;

Dimethyl(5-fluoro-2-(((3-hydroxy-10,10-dimethyl-4-oxo-6,7,9,10-tetrahydro-4H-pyrimido[1,2-d][1,4]oxazepin-2-yl)carbonyl)amino)methyl)phenyl)-phosphonate;

N-(2-(4,5-Dimethyl-1H-1,2,3-triazol-1-yl)-4-fluorobenzyl)-3-hydroxy-10,10-dimethyl-4-oxo-6,7,9,10-tetrahydro-4H-pyrimido[1,2-d][1,4]oxazepine-2-carboxamide; and N-(4-fluoro-2-(5-methyl-1H-1,2,3-triazol-1-yl)benzyl)-3-hydroxy-10,10-dimethyl-4-oxo-6,7,9,10-tetrahydro-4H-pyrimido[1,2-d][1,4]oxazepine-2-carboxamide;

or a pharmaceutically acceptable salt thereof.

11. A compound of claim 1 selected from the group consisting of

N-((4-Fluoro-2-(1H-1,2,4-triazol-1-yl)phenyl)methyl)-3-hydroxy-10,10-dimethyl-4-oxo-6,7,9,10-tetrahydro-4H-pyrimido[1,2-d][1,4]oxazepine-2-carboxamide N-((4-Fluoro-2-(methylsulfonyl)phenyl)methyl)-3-hydroxy-10,10-dimethyl-4-oxo-6,7,9,10-tetrahydro-4H-pyrimido[1,2-d][1,4]oxazepine-2-carboxamide;

N-((4-Fluoro-2-(5-methyl-1H-1,2,4-triazol-1-yl)phenyl)methyl)-3-hydroxy-10,10-dimethyl-4-oxo-6,7,9,10-tetrahydro-4H-pyrimido[1,2-d][1,4]oxazepine-2-carboxamide;

N-((2-(3,5-dimethyl-1H-1,2,4-triazol-1-yl)-4-fluorophenyl)methyl)-3-hydroxy-10,10-dimethyl-4-oxo-6,7,9,10-tetrahydro-4H-pyrimido[1,2-d][1,4]oxazepine-2-carboxamide;

N-((4-fluoro-2-(3-methyl-1H-1,2,4-triazol-1-yl)phenyl)methyl)-3-hydroxy-10,10-dimethyl-4-oxo-6,7,9,10-tetrahydro-4H-pyrimido[1,2-d][1,4]oxazepine-2-carboxamide;

N-((4-fluoro-2-(2-oxo-1-pyrrolidinyl)phenyl)methyl)-3-hydroxy-10,10-dimethyl-4-oxo-6,7,9,10-tetrahydro-4H-pyrimido[1,2-d][1,4]oxazepine-2-carboxamide;

Dimethyl (5-fluoro-2-((((3-hydroxy-10,10-dimethyl-4-oxo-6,7,9,10-tetrahydro-4H-pyrimido[1,2-d][1,4]oxazepin-2-yl)carbonyl)amino)methyl)phenyl)-phosphonate;

N-(2-(4,5-Dimethyl-1H-1,2,3-triazol-1-yl)-4-fluorobenzyl)-3-hydroxy-10,10-dimethyl-4-oxo-6,7,9,10-tetrahydro-4H-pyrimido[1,2-d][1,4]oxazepine-2-carboxamide; and N-(4-fluoro-2-(5-methyl-1H-1,2,3-triazol-1-yl)benzyl)-3-hydroxy-10,10-dimethyl-4-oxo-6,7,9,10-tetrahydro-4H-pyrimido[1,2-d][1,4]oxazepine-2-carboxamide;

or a pharmaceutically acceptable salt thereof.

12. A compound of claim 1 selected from the group consisting of

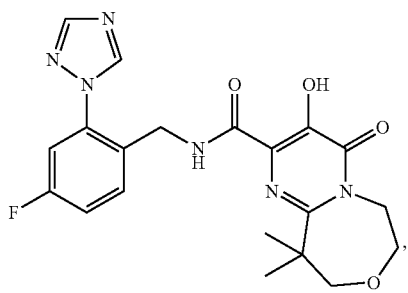

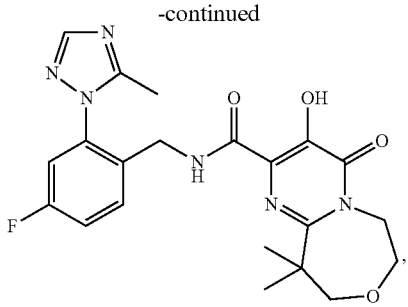

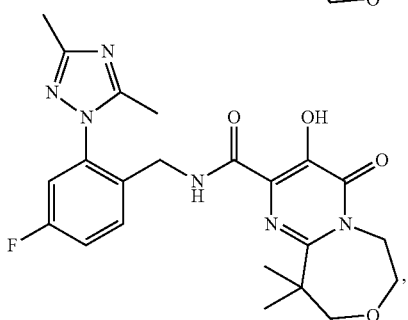

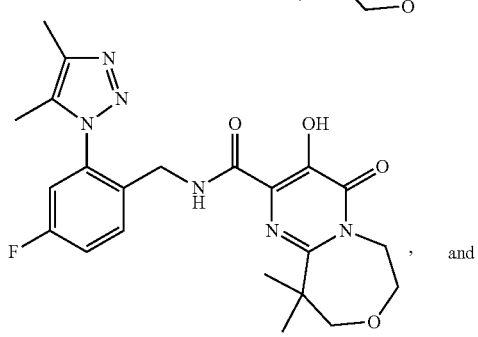

, and

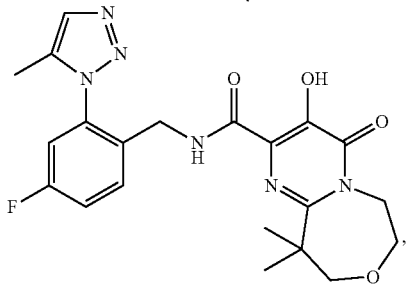

, or a pharmaceutically acceptable salt thereof.

13. A composition comprising a therapeutic amount of a compound of claim 1 and a pharmaceutically acceptable carrier.

14. A method for treating HIV infection comprising administering a therapeutically effective amount of a compound of claim 1, or a pharmaceutically acceptable salt thereof, to a patient in need thereof.

* * * * *

UNITED STATES PATENT AND TRADEMARK OFFICE
CERTIFICATE OF CORRECTION

PATENT NO. : 8,039,458 B2
APPLICATION NO. : 11/590637
DATED : October 18, 2011
INVENTOR(S) : B. Narasimhulu Naidu et al.

It is certified that error appears in the above-identified patent and that said Letters Patent is hereby corrected as shown below:

On the Title Page:

Item (75), Inventors:

Change "Francis Beaulieu, Laprairie (CA)" to -- Francis Beaulieu, Québec (CA) --.

Column 75, lines 28 to 36, change structure for Intermediate 146 from

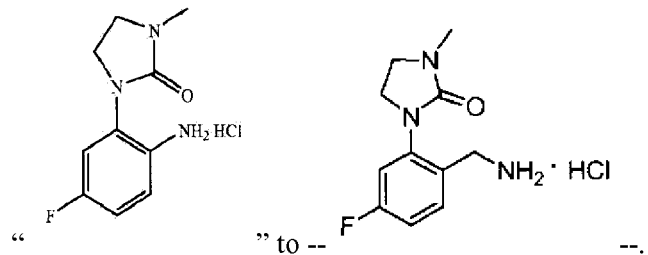

" to -- -- --.

Claim 1:

Column 113, line 57, change "cyclolkyl" to -- cycloalkyl --.

Claim 2:

Column 114, line 56, after "SOR$^7$," insert -- S(=NR$^7$), --.

Column 114, line 59, after "cyano," insert -- C$_{1-6}$alkyl, --.

Column 114, line 60, change "C$_{3-6}$haloalkoxy" to -- C$_{1-6}$haloalkoxy --.

Column 115, line 18, after "R$^{14}$ is", delete "dependency hydrogen or".

Column 115, line 64, change "CH$_7$" to -- CH$_2$ --.

Claim 10:

Column 116, line 60, change "(((3" to -- ((((3 --.

Claim 11:

Column 117, line 9, after "carboxamide", insert -- ; --.

Signed and Sealed this
Fourth Day of September, 2012

David J. Kappos
*Director of the United States Patent and Trademark Office*